US007704967B2

(12) United States Patent
Gnatt

(10) Patent No.: US 7,704,967 B2
(45) Date of Patent: Apr. 27, 2010

(54) TFIIS AND GDOWN1 AS TARGETS FOR CANCER THERAPY

(75) Inventor: Averall Gnatt, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 11/683,172

(22) Filed: Mar. 7, 2007

(65) Prior Publication Data
US 2007/0225241 A1 Sep. 27, 2007

Related U.S. Application Data

(60) Provisional application No. 60/782,203, filed on Mar. 14, 2006.

(51) Int. Cl.
*A61K 48/00* (2006.01)
*A61K 35/12* (2006.01)
*C07H 21/02* (2006.01)
*C07H 21/04* (2006.01)
*C12Q 1/68* (2006.01)

(52) U.S. Cl. .................. 514/44; 536/23.1; 536/24.5; 424/277.1; 435/6

(58) Field of Classification Search .............. None
See application file for complete search history.

(56) References Cited

U.S. PATENT DOCUMENTS 5,596,091 A * 1/1997 Switzer .............. 536/24.5
2005/0287128 A1* 12/2005 Guerciolini et al. ...... 424/93.21

FOREIGN PATENT DOCUMENTS

| WO | WO-98/41648 | 9/1998 |
| WO | WO-01/72777 | 10/2001 |
| WO | WO-02/22660 | 3/2002 |

OTHER PUBLICATIONS

Scherer et al., Approaches for the sequence-specific knockdown of mRNA, 2003, Nat. Biotechnol., 21(12), pp. 1457-1465.*
Mahato et al., Modulation of gene expression by antisense and antigene oligodeoxynucleotides and small interfering RNA, Jan. 2005, Expert Opinion on Drug Delivery, vol. 2, No. 1, pp. 3-28.*
Zhang et al., Targeted Gene Silencing by Small Interfering RNA-Based Knock-Down Technology, 2004, Current Pharmaceutical Biotechnology, vol. 5, p. 1-7.*
Astrom et al., Conserved Mechanism of PLAG1 Activation in Salivary Gland Tumors with and without Chromosome 8q12 Abnormalities: Identification of SII as a New Fusion Partner Gene, 1999, Cancer Research, 59, pp. 918-923.*
Yoo et al., Cloning, expression and characterization of the human transcription elongation factor, TFIIS, 1991, Nucleic Acids Research, vol. 19, No. 5, pp. 1073-1079.*
Bertrand et al., Comparison of antisense oligonucleotides and siRNAs in cell culture and in vivo, 2002, Biochemical and Biophysical Research Communications, 296, pp. 1000-1004.*
Keene et al., Transcriptional pause, arrest and termination sites for RNA polymerase II in mammalian N- and c-myc genes, 1999, Nucleic Acids Research, vol. 27, No. 15, pp. 3173-3182.*
Watson et al., Inhibition of c-myc Expression by Phosphorothioate Antisense Oligonucleotide Identifies a Critical Role for c-myc in the Growth of Human Breast Cancer, 1991, Cancer Research, 51, pp. 3996-4000.*
Lima et al., Specific downregulation of bcl-2 and xIAP by RNAi enhances the effects of chemotherapeutic agents in MCF-1 human breast cancer cells, 2004, Cancer Gene Therapy, 11, pp. 309-316.*
Lingor et al., Targeting neurological disease with RNAi, 2007, Mol. BioSyst., 3, pp. 773-780.*
Astrom et al., "Conserved mechanism of PLAG1 activation in salivary gland tumors with and without chromosome 8q12 abnormalities: identification of SII as a new fusion partner gene"; Cancer Res: 1999; p. 918-23.; vol. 59(4).
Bains et al., "Distribution and configuration of c-myc RNA during transcriptional attenuation in differentiating cells in-situ"; Histochem Cell Biol; 1997; p. 259-63, vol. 107(3).
Keene et al., "Transcriptional pause, arrest and termination sites for RNA polymerase II in mammalian N- and c-myc genes"; Nucleic Acids Res; 1999; p. 3173-82; vol. 27(15).
Kerppola et al., "Analysis of the signals for transcription termination by purified RNA polymerase II"; Biochemistry; 1990; p. 269-78; vol. 29(1).
Kerppola, et al., "Intrinsic sites of transcription termination and pausing in the c-myc gene"; Mol Cell Biol; 1988; p. 4389-94; 8(10).
Hubbard, Kyle, Catalano, Jennifer, Puri, Raj K., Gnatt, Averell. Knockdown of TFIIS by RNA silencing inhibits cancer cell proliferation and induces apoptosis. BCM Cancer, May 12, 2008, 8:133.
Asp et al., "CHCHD7-PLAG1 and TCEA1-PLAG1 gene fusions resulting from cryptic, intrachromosomal 8q rearrangements in pleomorphic salivary gland adenomas", Genes Chromosomes Cancer. Sep. 2006;45(9):820-8.
Astrom et al., "Evidence of involvement of the PLAG1 gene in lipoblastomas"; Int J Oncol. Jun. 2000;16(6):1107-10.
DeClercq "Salivary gland tumors in transgenic mice with targeted PLAG1 proto-oncogene overexpression", Cancer research, 2005, 65(11), pp. 4544-4553.
Enlund et al., "Expression of PLAG1 and HMGIC proteins and fusion transcripts in radiation-associated pleomorphic adenomas", Int J Oncol. Apr. 2002;20(4):713-6.
Zatkova et al., "Amplification and overexpression of the IGF2 regulator PLAG1 in hepatoblastoma", Genes Chromosomes Cancer. Feb. 2004;39(2):126-37.
Zhao et al., "Wnt pathway is involved in pleomorphic adenomas induced by overexpression of PLAG1 in transgenic mice", International Journal of Cancer, 118 (3), 643-648, Published Online: Aug. 17, 2005.

* cited by examiner

Primary Examiner—Amy Bowman
(74) Attorney, Agent, or Firm—Fulbright & Jaworski LLP

(57) ABSTRACT

The present invention concerns cancer therapy related to the targeting of at least one core transcription factor. In particular, the compositions and methods of the invention concern targeting TFIIS, GDOWN1, or both for cancer therapy. In specific aspects, TFIIS and/or GDOWN1 inhibitors are employed for breast, prostate, pancreatic, and/or lung cancer.

5 Claims, 18 Drawing Sheets

| Temp0(+) Temp0(−) | AAAAAGAAGGGGCTTTGCGGAACGAGCGACCACAA-5' (SEQ ID NO:1) |
| --- | --- |
| | TTTTTCTTCCCCGAAACGCCTTGCTCGCTGGTGTTCCCCCCCCCCCC-3' (SEQ ID NO:2) |
| TempT5(+) TempT5(−) | GAAGGGGCGAGGCGGG<u>GTTTT</u>TCGACCACAA-5' (SEQ ID NO:3) |
| | CTTCCCCGCTCCGCCCAAAAAGCTGGTGTTCCCCCCCCCCCC-3' (SEQ ID NO:4) |

| | | | | |
|---|---|---|---|---|
| Gdown 1 | 57 | KLKAAIAECEEVRRKSELFNPVSLD (SEQ ID NO:54) | 337 | NIKMRSYNPEGESSG (SEQ ID NO:55) |
| Gdown 2 | 57 | KLKAAIAECEEVGRKSELFNPVSLD (SEQ ID NO:56) | 337 | LSLAAAAKDTRGSKS (SEQ ID NO:57) |
| Gdown6 | 41 | ------------------------------------------- | 180 | NIKMRSYNPEGESSG (SEQ ID NO:58) |
| Gcom1 | 124 | EMRQKIRQLTQELSVSHAQQEYLEN (SEQ ID NO:59) | 519 | NIKMRSYNPEGESSG (SEQ ID NO:60) |
| Peptide | A | .........AAIAEREEVRGRSELFYPV....... (SEQ ID NO:61) | B | ......MQXYNPEGE...... (SEQ ID NO:62) |

B

| | | | | |
|---|---|---|---|---|
| Human | 57 | KLKAAIAECEEVRRKSELFNPVSLD (SEQ ID NO:63) | 337 | NIKMRSYNPEGESSG (SEQ ID NO:64) |
| Orangutan | 57 | KLKAAIAECEEVRRKSELCHPVSLD (SEQ ID NO:65) | 336 | NIKMRSYNPEGESSG (SEQ ID NO:66) |
| Mouse | 57 | KLKAAISEREEVRGRSELFHPVSVD (SEQ ID NO:67) | 335 | NIKMQSYNPEGESSG (SEQ ID NO:68) |
| Frog | 57 | KLKAAISEREEVRGRSELFHPVSVD (SEQ ID NO:69) | 335 | NIKMQSYNPEGESSG (SEQ ID NO:70) |
| Rat | 57 | KLKAAISEREEVRGRTELFHPVSVD (SEQ ID NO:71) | 333 | NIKMQSFNPEGESSG (SEQ ID NO:72) |
| Bovine | 57 | KLKAAIAEREEVRGRSELFYPVSLD (SEQ ID NO:73) | 338 | NIKMQSYNPEGESSR (SEQ ID NO:74) |
| Peptide | A | .........AAIAEREEVRGRSELFYPV....... (SEQ ID NO:75) | B | ......MQXYNPEGE...... (SEQ ID NO:76) |

FIG. 11

```
Gdown1      1 ------------------------MCSLPRGFEPQAPEDLAQRSLVELREMLKRQER
Gdown2      1 ------------------------MCSLPRGFEPQAPEDLAQRSLVELREMLKRQER
Gdown6      1 ------------------------MCSLPRGFEPQAPEDLAQRSLVELREMLKRQER
Gcom1       1 MLRSTSTVTLLSGGAARTPGAPSRRANVCRLRLTVPPESPVPEQCEKKIERKEQLLDLSN Gdown1     34 LLRNEKFIC-----------------------------------KLPDKGKRIFD
Gdown2     34 LLRNEKFIC-----------------------------------KLPDKGKKIFD
Gdown6     34 LLRNE-------------------------------------------------
Gcom1      61 GEPTRKLPQGVVYGVVRRSDQNQQKEMVVYGWSTSQLKEEMNYIKDVRATLEKVRKRMYG Gdown1     54 SFAKLKAAIAECEEVRRKSELFNPVSLDCKLRQKAIAEVDVGTDKAQNSDPILDTSSLVP
Gdown2     54 SFAKLKAAIAECEEVGRKSELFNPVSLDCKLRQKAIAEVDVGTDKAQNSDPILDTSSLVP
Gdown6     38 --------------------------------------------------------
Gcom1     121 DYDEMRQKIRQLTQELSVSHAQQEYLENHIQTQSSALDRFNAMNSALASDSIGLQKTLVD
PeptideA   54 ................AAIAEREEVRGRSELYPV Gdown1    114 GCSSVDNIKSSQT-----------------------SQNQGLGRPTLEGDEETSEVEYT
Gdown2    114 GCSSVDNIKSSQT-----------------------SQNQGLGRPTLEGDEETSEVEYT
Gdown6     38 --------------------------------------------------------
Gcom1     181 VTLENSNIKDQIRNLQQTYEASMDKLREKQRQLEVAQVENQLLKMKVESSQEANAEVMRE Gdown1    150 VNKGPASSNRDRVPPSS-----------------------EASEHHPRHRVSSQAEDTSSS
Gdown2    150 VNKGPASSNRDRVPPSS-----------------------EASEHHPRHRVSSQAEDTSSS
Gdown6     38 --------------------------------------------------------
Gcom1     241 MTKKLYSQYEEKLQEEQRKHSAEKEALLEETNSFLKAIEEANKKMQAAEISLEEKDQRIG Gdown1    188 FDNLFIDRLQRITIADQGEQQSEENASTKNLTG-----------LSSGTEKKPHYMEVL
Gdown2    188 FDNLFIDRLQRITIADQGEQQSEENASTKNLTG-----------LSSGTEKKPHYMEVL
Gdown6     38 --------LQRITIADQGEQQSEENASTKNLTG-----------LSSGTEKKPHYMEVL
Gcom1     301 ELDRLIERMEKERHQLQLQLLEHETEMSGELTDSDKERYQQLEEASASLRERIRHLDDMV Gdown1    236 EMRAKNPVPQLRKFKTN---------------------------------
Gdown2    236 EMRAKNPVPQLRKFKTN---------------------------------
Gdown6     79 EMRAKNPVPQLRKFKTN---------------------------------
Gcom1     361 HCQQKKVKQMVEEIESLKKKLQQKQLLILQLLEKISFLEGENNELQSRLDYLTETQAKTE Gdown1    253 --------------VLPFRQNDSSSHCQKSGSPISSEERRRRDKQHLDDITAARLLPLHH
Gdown2    253 --------------VLPFRQNDSSSHCQKSGSPISSEERRRRDKQHLDDITAARLLPLHH
Gdown6     96 --------------VLPFRQNDSSSHCQKSGSPISSEERRRRDKQHLDDITAARLLPLHH
Gcom1     421 VETREIGVGCDLLPRLPFRQNDSSSHCQKSGSPISSEERRRRDKQHLDDITAARLLPLHH Gdown1    299 MPTQLLSIEESLALQKQQKQNYEEMQAKLAAQKLAERLNIKMRSYNPEGESSGRYREVRD
Gdown2    299 MPTQLLSIEESLALQKQQKQNYEERPFYSPQYRSSMNLLSLAAAAKDTRGKSGKMGSLA
Gdown6    142 MPTQLLSIEESLALQKQQKQNYEEMQAKLAAQKLAERLNIKMRSYNPEGESSGRYREVRD
Gcom1     481 MPTQLLSIEESLALQKQQKQNYEEMQAKLAAQKLAERLNIKMRSYNPEGESSGRYREVRD
PeptideB  481 ................................MQYNPEGE Gdown1    359 EDDDWSSDEF (SEQ ID NO:35)
Gdown2    359 LLTKL----- (SEQ ID NO:37)
Gdown6    202 EDDDWSSDEF (SEQ ID NO:39)
Gcom1     541 EDDDWSSDEF (SEQ ID NO:41)
```

FIG. 15

```
Human      1 MCSLPRGFEPQAPEDLAQRSLVELREMLKRQERLLRNEKFICKLPDKGKKIEDSEAKLKA
Orangutan  1 MCSLPRGFEPQVPEDLERRSLAELREMLKRQERLLRNEKFICKLPDKGKKIEDSEAKLKA
Mouse      1 MESLPRGFEPPAPEDLGRQSSAELRERLRRQERLLRNEKFICKLPDKGKKISDTVAKLKA
Frog       1 MESLPRGFEPPAPEDLGRQSSAELRERLRRQERLLRNEKFICKLPDKGKKISDTVAKLKA
Rat        1 MCSLPRGFEPPAPEDLGRQSSAELRERLRRQERLLRNEKFICKLPDKGKKISDTIAKLKA
Bovine     1 MSSLPRGFEPQTPEDLGQRSLAELREMLKRQERLLRNVKFICKLPDKGKKISDAVTKLKA
PeptideA   ............................................................A Human     61 AIAECEEVRRKSELFNPVSLDCKLRQKAIAEVDVGTDKAQNSDPILDTSSLVPGCSSVDN
Orangutan 61 AIAECEEVRRKSELCHPVSLDCKLRQKAIAEVDVGTDKAQNSDPILDTSSLVPGCSSVDN
Mouse     61 AISEREEVRGRSELFHPVSVDCKLRQKATTRADIDVDKAQSSDLMLDTSSLVPDCSSIDI
Frog      61 AISEREEVRGRSELFHPVSVDCKLRQKATTRADIDVDKAQSSDLMLDTSSLDPDCSSIDI
Rat       61 AISEREEVRGRTELFHPVSVDCKLRHKATTRVDIDIDKAQNSDLMLDTSSLVPECSSVDI
Bovine    61 AIAEREEVRGRSELFYPVSLDCKERQKAIAVVDGDRDKAQNSDQILDTSSEVPGCSSVAN
PeptideA     AIAEREEVRGRSELFYPV (SEQ ID NO:52)

Human    121 IKSSQ-TSQNQGLGRPILEGDEETSEVEYTVNKGPASSNRDRVPPSS-EASEHHPRHRVSS
Orangutan 121 IKSSQ-TSQNQGLGRPILEGDEETSEVEYSVNKGPASSNRDRVPPSS-EASEYHLQHRVSS
Mouse    121 KSS-KSTSEIQGPTHLTHRGNEETLEAGYTVNSSPAAHIRARAPSS-EVKEHLPQHSVSS
Frog     121 KSS-KSTSEIQGPTHLTHRGNEETLEAGYTVNSSPAAHIRARAPSS-EVKEHLPQHSVSS
Rat      121 ESS-KTTSEIQGPTHLTHKGNEETIATGCTVNTCPSARITQDPSS-EVNEHLPQH--SS
Bovine   121 ITSSQTTSRQQGLAHPTRGGDAEAAEAEHTVSEHPTSSSGAPAPSSSQASE-GLPQHCALR Human    180 QAEDTSSSFDNLFIDRLQRITIADQGFQQSEENASTKNLIGLSSGIEKKPHYMEVLEMRA
Orangutan 180 QAEDTSSSFDNLFIDRLQRITIADQGFQQSE-NASTKNLIGLSSGIQKKPHYMEVLEMRA
Mouse    179 QEEEISSSIDSLFITKLQKITIADQSEPSEE-NISTENFPELQSEIPKKPHYMKVLEMRA
Frog     179 QEEEISSSIDSLFITKLQKITIADQSEPSEE-NISTENFPELQSEIPKKPHYMKVLEMRA
Rat      177 QVEEISSSVDSLFITKLQKITIADQIEPSEE-NISTENFPGLQSEIPKKPHYMKVLEMRA
Bovine   181 QVEDHPGSSDNLFIDRLQRITSADPTEHHSFGNRNPENLAGIWSGPQKKPHYMEVLEMRA Human    240 KNPVPQIRKFKTNVLPFRQNDSSSHCQKSGSPISSEERRRRDKQHLDDITAARLIPLHHM
Orangutan 239 KNPVPQIHKFKTNVLPFRQNDSSSHCQKSRSPISSEERRRRDKQHLDDITAARLIPLHHM
Mouse    238 RNPVPPPHKFKTNVLPTQQSDSPSHCQRGQSPASSEERRRRARQHLDDITAARLIPLHHL
Frog     238 RNPVPPPHKFKTNVLPTQQSDSPSHCQRGQSPASSEEQRRRARQHLDDITAARLIPLHHL
Rat      236 KNPVPPPHKFKTNVLPTQQSDSSSHCHKGQSPASSEEHRRRARQHLDDVTAARLIPLHHL
Bovine   241 KNPMPPPHKFKTNVLPSQPRDSSACQRRGSPISSEERRRRDRKHLDDITAARLIPLHHL Human    300 PTQLLSIEESLAIQKQQKQNYEEMQAKLAAQKLAERINIKMRSYNPEGESSGRYREVRDE
Orangutan 299 PTQLLSIEESLAIQKQRKQKYEEMQAKLAAQKLAERINIKMRSYNPEGESSGRYREVRDE
Mouse    298 PAQLLSIEESLAIQREQKQNYEEMQAKLAAQKLAERINIKMQSYNPEGESSGRYREVRDE
Frog     298 PAQLLSIEESLAIQREQKQNYEEMQAKLAAQKLAERINIKMQSYNPEGESSGRYREVRDE
Rat      296 PAQLLSIEESLAIQKEQKQNYEEMQAKLAAQKLAERINIKMQSENPEGESSGRYREVRDE
Bovine   301 PTQLLSIEESLAIQRQQKQSYEEIQAKLAAQKLAERINIKMQSYNPEGESSRKYREVRDE
PeptideB     ....................................MQXYNPEGE(SEQ ID NO:53)

Human    360 DDDWSS-DEF  (SEQ ID NO:42)
Orangutan 359 DDDWSS-DEF  (SEQ ID NO:43)
Mouse    358 ADAQSS-DEC  (SEQ ID NO:44)
Frog     358 ADAQSS-DEC  (SEQ ID NO:47)
Rat      356 DDAQSS-DEC  (SEQ ID NO:45)
Bovine   361 DDDQSSEDEF  (SEQ ID NO:51)
```

FIG. 16

| PCR reaction | B-actin Cycle Threshold | | Gdown Cycle Threshold | | Gdown1 mRNA expression |
|---|---|---|---|---|---|
| | Vehicle | siRNA 5nM | Vehicle | siRNA 5 NM | |
| Reaction 1 | 15.9 | 16.4 | 22.4 | 23.8 | |
| | 15.7 | 15.8 | 22.7 | 23.4 | |
| | 15.8 | 16.0 | 22.7 | 23.4 | |
| Average | 15.8 | 16.0 | 22.6 | 23.5 | 60% |
| Reaction 2 | 16.1 | 16.0 | 23.0 | 24.0 | |
| | 16.0 | 16.4 | 22.9 | 23.8 | |
| | 16.2 | 15.9 | 22.7 | 23.7 | |
| Average | 16.1 | 16.1 | 22.8 | 23.8 | 48% |
| Reaction 3 | 15.8 | 15.8 | 22.8 | 23.4 | |
| | 15.9 | 15.7 | 22.8 | 23.7 | |
| | 15.7 | 15.8 | 22.9 | 23.7 | |
| Average | 15.8 | 15.7 | 22.8 | 23.6 | 51% |
| | | | | | |
| Average | | | | | 53% |
| S.D. | | | | | 6.2 |

FIG. 17

SEQUENCE LISTING

```
<160> NUMBER OF SEQ ID NOS: 76

<210> SEQ ID NO 1
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 1
aacaccagcg agcaaggcgt tcggggaag aaaaa                              35

<210> SEQ ID NO 2
```

```
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 2
tttttcttcc ccgaaacgcc ttgctcgctg gtgttccccc cccccc           47

<210> SEQ ID NO 3
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 3
aacaccagct ttttgggcgg agcggggaag                             30

<210> SEQ ID NO 4
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 4
cttccccgct ccgcccaaaa agctggtgtt cccccccccc cc               42

<210> SEQ ID NO 5
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 5
aaugcuauuc gcaagcagag u                                      21

<210> SEQ ID NO 6
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 6
aatgctattc gcaagcagag tcctgtctc                              29

<210> SEQ ID NO 7
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 7
aaactctgct tgcgaatagc acctgtctc                              29

<210> SEQ ID NO 8
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 8
```
aacaggggau gacuacauug c    21

<210> SEQ ID NO 9
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 9
aacaggggat gactacattg ccctgtctc    29

<210> SEQ ID NO 10
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 10
aagcaatgta gtcatcccct gcctgtctc    29

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11
gctatccagg ctgtgctatc    20

<210> SEQ ID NO 12
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 12
tgtcacgcac gatttcc    17

<210> SEQ ID NO 13
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 13
cttctgcctc ctcctctc    18

<210> SEQ ID NO 14
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 14
ctccatagtc cttgtaatca tc    22

<210> SEQ ID NO 15
<211> LENGTH: 2634
<212> TYPE: DNA

<213> ORGANISM: Human

<400> SEQUENCE: 15

```
gccgccgccg ccgccgccgc cgcgggcttc gttcgtaagg aaggggcct aggccgggcc      60
tgcggtggtg ggggttgctg cgcgccgggg gtcgctcctg ctgtgtcttc cgctccagct    120
tcgcccactt cccttacca gcggggtggg cgcggagaag acctgccgga gccatggagg     180
acgaagtggt ccgctttgcc aagaagatgg acaagatggt gcagaagaag aacgcggctg    240
gagcattgga tttgctaaag gagcttaaga atattcctat gaccctggaa ttactgcagt    300
ccacaagaat cggaatgtca gttaatgcta ttcgcaagca gagtacagat gaggaagtta    360
catctttggc aaagtctctc atcaaatcct ggaaaaaatt attagatggg ccatcaactg    420
agaaagacct tgacgaaaag aagaaagaac ctgcaattac atcgcagaac agccctgagg    480
caagagaaga aagtacttcc agcggcaatg taagcaacag aaaggatgag acaaatgctc    540
gagatactta tctttcatcc tttcctcggg caccaagcac ttctgattct gtgcggttga    600
agtgtaggga gatgcttgct gcagctcttc gaacagggga tgactacatt gcaattggag    660
ctgatgagga agaattagga tctcaaattg aagaagctat atatcaagaa ataaggaata    720
cagacatgaa atacaaaaat agagtacgaa gtaggatatc aaatcttaaa gatgcaaaaa    780
atccaaattt aaggaaaaat gtcctctgtg ggaatattcc tcctgactta tttgctagaa    840
tgacagcaga ggaaatggct agtgatgagc tgaaagagat gcggaaaaac ttgaccaaag    900
aagccatcag agagcatcag atggccaaga ctggtgggac ccagactgac ttgttcacat    960
gtggcaaatg taaaaagaag aattgcactt acacacaggt acaaacccgt agtgctgatg   1020
aaccaatgac aacatttgtt gtctgtaatg aatgtggaaa tcgatggaag ttctgttgag   1080
ttggaagaat tggcaaaata tctggaccat taagaaaacg gattttgtaa ctagctttaa   1140
actaggccaa gcaactagtt ttcctgcaaa tcaaattttt aaagcaactt gggttagact   1200
ttgttttga cctaacatcc cttccttaaa tgccttctgt agtttcagat cagtagggag     1260
accatataat aattgtatgg tacctgtttc aaaacatatt ttttctgttt ttataagtaa    1320
gttgatatta attaaactct tggcaatatt tcttctttct taaaggaaaa tataccttaa    1380
ctttttttct tttacactgt gaaacataca cagtagaaat tctgttactc tctgttatta    1440
atacataaat gaaatacat ttttttccat attggcatgt agctacaaat attaaaggag    1500
gagaaaggt aatataattt taggtttacc aaatatggtg tgtattcaaa taatacttga    1560
ccagcttatc taaaatgtac ataattttga ggtagcttat gaatttgatt ttaattatta    1620
tgttcacaag cttggaatat tagatattat tttgcatctg taactaaccg tgatcatcat    1680
ttcttgtaat ttcttgtaca tgtatattac ttgttcttaa tagattttg gaaacaagac     1740
tttattgaga tcagtttggt tttcctgtta atttacctgt ttgactttat aatgtgtttt    1800
agttttgcag aagaacactg ttgtagttta gaaggctttt cataaatccc ctcataggca    1860
aagatgaaaa cttcccacta tttttttccc ctcttaggaa gacatactgg aaagaaaatg    1920
tttagcatct tagtgtagta tagctattgt aaacagttca tgactagatt ttgattcgga    1980
aatctatact gaccaaggat taatcttaag gattgtataa ttcattaaag ctgtggtctt    2040
tccatgtgga gactgataga aaataatttt gtcccaagtc ttatttgctg acttttctg    2100
tcatgagtga gattgttgaa caaactgaat atatgggcta tagcaagtag ctttacagta    2160
cagatcttac aattaagttt tgcttttgtt aaagtgtgta ccattttttc tgtttggagt    2220
aagacaaaaa ttgttttgac ataggttccc tagggtacac ttgctctagc atactttaaa   2280
```

```
ggccactgtt gcaaagtcta cattttatgc tgaatctgca ttctgtcagg cacccataga    2340
aagacctcag tacatgcttt gcactctcct ttgctcccct tttccaattt cttattgcat    2400
atcattttgt tgtaatacag aaagcagcat ttttaaatgt ccgtgttaag aattggcccg    2460
ctggtaccaa ctcacctcta ttttgtcagt tcatagttga agattttgtt ttatttcaaa    2520
aagaaagtac attttgaaa taatgtttca gaataaaata atctcacttt taagtgatcc     2580
attttaaaat ttgtaattca ataaagtttt ttttgttgtt aaacataaaa aaaa          2634
```

<210> SEQ ID NO 16
<211> LENGTH: 301
<212> TYPE: PRT
<213> ORGANISM: Human

<400> SEQUENCE: 16

```
Met Glu Asp Glu Val Val Arg Phe Ala Lys Lys Met Asp Lys Met Val
1               5                   10                  15

Gln Lys Lys Asn Ala Ala Gly Ala Leu Asp Leu Leu Lys Glu Leu Lys
                20                  25                  30

Asn Ile Pro Met Thr Leu Glu Leu Leu Gln Ser Thr Arg Ile Gly Met
            35                  40                  45

Ser Val Asn Ala Ile Arg Lys Gln Ser Thr Asp Glu Glu Val Thr Ser
50                  55                  60

Leu Ala Lys Ser Leu Ile Lys Ser Trp Lys Lys Leu Leu Asp Gly Pro
65                  70                  75                  80

Ser Thr Glu Lys Asp Leu Asp Glu Lys Lys Lys Glu Pro Ala Ile Thr
                85                  90                  95

Ser Gln Asn Ser Pro Glu Ala Arg Glu Glu Ser Thr Ser Ser Gly Asn
            100                 105                 110

Val Ser Asn Arg Lys Asp Glu Thr Asn Ala Arg Asp Thr Tyr Leu Ser
        115                 120                 125

Ser Phe Pro Arg Ala Pro Ser Thr Ser Asp Ser Val Arg Leu Lys Cys
    130                 135                 140

Arg Glu Met Leu Ala Ala Ala Leu Arg Thr Gly Asp Asp Tyr Ile Ala
145                 150                 155                 160

Ile Gly Ala Asp Glu Glu Glu Leu Gly Ser Gln Ile Glu Glu Ala Ile
                165                 170                 175

Tyr Gln Glu Ile Arg Asn Thr Asp Met Lys Tyr Lys Asn Arg Val Arg
            180                 185                 190

Ser Arg Ile Ser Asn Leu Lys Asp Ala Lys Asn Pro Asn Leu Arg Lys
        195                 200                 205

Asn Val Leu Cys Gly Asn Ile Pro Pro Asp Leu Phe Ala Arg Met Thr
    210                 215                 220

Ala Glu Glu Met Ala Ser Asp Glu Leu Lys Glu Met Arg Lys Asn Leu
225                 230                 235                 240

Thr Lys Glu Ala Ile Arg Glu His Gln Met Ala Lys Thr Gly Gly Thr
                245                 250                 255

Gln Thr Asp Leu Phe Thr Cys Gly Lys Cys Lys Lys Asn Cys Thr
            260                 265                 270

Tyr Thr Gln Val Gln Thr Arg Ser Ala Asp Glu Pro Met Thr Thr Phe
        275                 280                 285

Val Val Cys Asn Glu Cys Gly Asn Arg Trp Lys Phe Cys
    290                 295                 300
```

```
<210> SEQ ID NO 17
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 17
caccatgtgc tcgctgcccc gcggcttcga gc                                32

<210> SEQ ID NO 18
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 18
tcagaattca tcagaggacc aatcgtcatc                                   30

<210> SEQ ID NO 19
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 19
tttttcttcc ccgaaacgcc ttgctcgctg gtgttccccc ccccccc                47

<210> SEQ ID NO 20
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 20
aacaccagcg agcaaggcgt ttcggggaag aaaaa                             35

<210> SEQ ID NO 21
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 21
aagucaucuc aaaccucaca a                                            21

<210> SEQ ID NO 22
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 22
aauuaugagg agaugcaagc a                                            21

<210> SEQ ID NO 23
<211> LENGTH: 24
<212> TYPE: DNA
<213> ORGANISM: Artificial Sequence
<220> FEATURE:
<223> OTHER INFORMATION: Synthetic Oligonucleotide
```

<400> SEQUENCE: 23
cattgcggac caaggtgaac aaca                                         24

<210> SEQ ID NO 24
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 24
agacccactc ttctggcaat gact                                         24

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 25
gctatccagg ctgtgctatc                                              20

<210> SEQ ID NO 26
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 26
tgtcacgcac gatttcc                                                 17

<210> SEQ ID NO 27
<211> LENGTH: 1119
<212> TYPE: DNA
<213> ORGANISM: Human

<400> SEQUENCE: 27
agcccgcgca gaatgtgctc gctgccccgc ggcttcgagc cccaagctcc cgaggacttg    60
gcgcagcgga gtttggtgga gctgcgggaa atgttgaagc gccaggagag acttttgcgc   120
aacgaaaaat tcatttgcaa attgcccgac aaaggtaaaa agatctttga ctcttttgcc   180
aaactgaaag ctgccattgc agaatgtgaa gaagttagaa gaaaaagtga actgtttaac   240
cctgttagtt tagactgtaa gctaaggcaa aaagcaattg cagaagttga tgtgggtaca   300
gataaggccc agaattctga cccgatactt gatacttcat cactagttcc tggatgttcc   360
tctgtagata acatcaagtc atctcaaacc tcacaaaacc agggacttgg acgtcctact   420
cttgaaggtg atgaagagac ttcagaggtt gagtacacag tgaataaggg cccagcttcc   480
agcaatagag acagggtacc accttcatct gaagctagtg agcatcaccc gcggcatcgt   540
gtttcaagtc aagcggaaga tacttccagc agctttgaca acctgtttat tgacaggtta   600
cagaggatca ccattgcgga ccaaggtgaa caacagtcag aagaaacgc aagtactaag   660 aacttgacag gccttttccag tgggactgag aagaaacctc attacatgga agtgctagaa   720
atgcgagcca aaaacccagt gccccagctg cgtaaattta aaaccaatgt gttacctttt   780
cgacaaaatg attcatctag tcattgccag aagagtgggt ctcctatttc ctcagaagag   840
cggcggcgca gggataagca gcatcttgat gacatcacag cagctcggct tctaccactt   900
caccatatgc ccacgcagct gctctccata gaagaatcct ggcacttca gaaacagcag   960

```
aaacagaatt atgaggagat gcaagcaaag ctcgcagcgc aaaaattagc tgaaagactg    1020
aatattaaaa tgcggagtta taatccagaa ggggagtctt cagggagata ccgagaagta    1080
agggatgaag atgacgattg gtcctctgat gaattctga                           1119

<210> SEQ ID NO 28
<211> LENGTH: 368
<212> TYPE: PRT
<213> ORGANISM: Human

<400> SEQUENCE: 28

Met Cys Ser Leu Pro Arg Gly Phe Glu Pro Gln Ala Pro Glu Asp Leu
1               5                   10                  15

Ala Gln Arg Ser Leu Val Glu Leu Arg Glu Met Leu Lys Arg Gln Glu
            20                  25                  30

Arg Leu Leu Arg Asn Glu Lys Phe Ile Cys Lys Leu Pro Asp Lys Gly
        35                  40                  45

Lys Lys Ile Phe Asp Ser Phe Ala Lys Leu Lys Ala Ala Ile Ala Glu
    50                  55                  60

Cys Glu Glu Val Arg Arg Lys Ser Glu Leu Phe Asn Pro Val Ser Leu
65                  70                  75                  80

Asp Cys Lys Leu Arg Gln Lys Ala Ile Ala Glu Val Asp Val Gly Thr
                85                  90                  95

Asp Lys Ala Gln Asn Ser Asp Pro Ile Leu Asp Thr Ser Ser Leu Val
            100                 105                 110

Pro Gly Cys Ser Ser Val Asp Asn Ile Lys Ser Ser Gln Thr Ser Gln
        115                 120                 125

Asn Gln Gly Leu Gly Arg Pro Thr Leu Glu Gly Asp Glu Glu Thr Ser
    130                 135                 140

Glu Val Glu Tyr Thr Val Asn Lys Gly Pro Ala Ser Ser Asn Arg Asp
145                 150                 155                 160

Arg Val Pro Pro Ser Ser Glu Ala Ser Glu His His Pro Arg His Arg
                165                 170                 175

Val Ser Ser Gln Ala Glu Asp Thr Ser Ser Phe Asp Asn Leu Phe
            180                 185                 190

Ile Asp Arg Leu Gln Arg Ile Thr Ile Ala Asp Gln Gly Glu Gln Gln
        195                 200                 205

Ser Glu Glu Asn Ala Ser Thr Lys Asn Leu Thr Gly Leu Ser Ser Gly
    210                 215                 220

Thr Glu Lys Lys Pro His Tyr Met Glu Val Leu Glu Met Arg Ala Lys
225                 230                 235                 240

Asn Pro Val Pro Gln Leu Arg Lys Phe Lys Thr Asn Val Leu Pro Phe
                245                 250                 255

Arg Gln Asn Asp Ser Ser His Cys Gln Lys Ser Gly Ser Pro Ile
            260                 265                 270

Ser Ser Glu Glu Arg Arg Arg Asp Lys Gln His Leu Asp Asp Ile
        275                 280                 285

Thr Ala Arg Leu Leu Pro Leu His His Met Pro Thr Gln Leu Leu
    290                 295                 300

Ser Ile Glu Glu Ser Leu Ala Leu Gln Lys Gln Lys Gln Asn Tyr
305                 310                 315                 320

Glu Glu Met Gln Ala Lys Leu Ala Ala Gln Lys Leu Ala Glu Arg Leu
                325                 330                 335

Asn Ile Lys Met Arg Ser Tyr Asn Pro Glu Gly Glu Ser Ser Gly Arg
```

340                 345                 350
Tyr Arg Glu Val Arg Asp Glu Asp Asp Trp Ser Ser Asp Glu Phe
        355                 360                 365

<210> SEQ ID NO 29
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 29

Ala Ala Ile Ala Glu Arg Glu Glu Val Arg Gly Arg Ser Glu Leu Phe
1               5                   10                  15

Tyr Pro Val Ser
            20

<210> SEQ ID NO 30
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 30

Met Tyr Ala Gln Xaa Tyr Asn Pro Glu Gly Glu
1               5                   10

<210> SEQ ID NO 31
<211> LENGTH: 21
<212> TYPE: RNA
<213> ORGANISM: Artificial Sequence
<220> FEATURE:
<223> OTHER INFORMATION: Synthetic Primer

<400> SEQUENCE: 31
aacgaaaaau ucauuugcaa a                                           21

<210> SEQ ID NO 32
<211> LENGTH: 21
<212> TYPE: RNA
<213> ORGANISM: Artificial Sequence
<220> FEATURE:
<223> OTHER INFORMATION: Synthetic Primer

<400> SEQUENCE: 32
aaguuagaag aaaaagugaa c                                           21

<210> SEQ ID NO 33
<211> LENGTH: 21
<212> TYPE: RNA
<213> ORGANISM: Artificial Sequence
<220> FEATURE:
<223> OTHER INFORMATION: Synthetic Primer

<400> SEQUENCE: 33
aagucaucuc aaaccucaca a                                           21

<210> SEQ ID NO 34
<211> LENGTH: 1119
<212> TYPE: DNA
<213> ORGANISM: Human

<400> SEQUENCE: 34

```
agcccgcgca gaatgtgctc gctgccccgc ggcttcgagc cccaagctcc cgaggacttg      60
gcgcagcgga gtttggtgga gctgcgggaa atgttgaagc gccaggagag acttttgcgc     120
aacgaaaaat tcatttgcaa attgcccgac aaaggtaaaa agatctttga ctcttttgcc     180
aaactgaaag ctgccattgc agaatgtgaa gaagttagaa gaaaaagtga actgtttaac     240
cctgttagtt tagactgtaa gctaaggcaa aaagcaattg cagaagttga tgtgggtaca     300
gataaggccc agaattctga cccgatactt gatacttcat cactagttcc tgatgttcc      360
tctgtagata acatcaagtc atctcaaacc tcacaaaacc agggacttgg acgtcctact     420
cttgaaggtg atgaagagac ttcagaggtt gagtacacag tgaataaggg cccagcttcc     480
agcaatagag acagggtacc accttcatct gaagctagtg agcatcaccc gcggcatcgt     540
gtttcaagtc aagcggaaga tacttccagc agctttgaca acctgtttat tgacaggtta     600
cagaggatca ccattgcgga ccaaggtgaa caacagtcag aagaaacgc aagtactaag      660
aacttgacag gccttttccag tgggactgag aagaaacctc attacatgga agtgctagaa    720
atgcgagcca aaaacccagt gccccagctg cgtaaattta aaccaatgt gttacctttt      780
cgacaaaatg attcatctag tcattgccag aagagtgggt ctcctatttc ctcagaagag     840
cggcggcgca gggataagca gcatcttgat gacatcacac cagctcggct tctaccactt     900
caccatatgc ccacgcagct gctctccata gaagaatcct tggcacttca gaaacagcag     960
aaacagaatt atgaggagat gcaagcaaag ctcgcagcgc aaaaattagc tgaaagactg    1020
aatattaaaa tgcggagtta taatccagaa ggggagtctt cagggagata ccgagaagta    1080
agggatgaag atgacgattg gtcctctgat gaattctga                            1119
```

<210> SEQ ID NO 35
<211> LENGTH: 368
<212> TYPE: PRT
<213> ORGANISM: Human

<400> SEQUENCE: 35

```
Met Cys Ser Leu Pro Arg Gly Phe Glu Pro Gln Ala Pro Glu Asp Leu
1               5                   10                  15

Ala Gln Arg Ser Leu Val Glu Leu Arg Glu Met Leu Lys Arg Gln Glu
            20                  25                  30

Arg Leu Leu Arg Asn Glu Lys Phe Ile Cys Lys Leu Pro Asp Lys Gly
        35                  40                  45

Lys Lys Ile Phe Asp Ser Phe Ala Lys Leu Lys Ala Ala Ile Ala Glu
    50                  55                  60

Cys Glu Glu Val Arg Arg Lys Ser Glu Leu Phe Asn Pro Val Ser Leu
65                  70                  75                  80

Asp Cys Lys Leu Arg Gln Lys Ala Ile Ala Glu Val Asp Val Gly Thr
                85                  90                  95

Asp Lys Ala Gln Asn Ser Asp Pro Ile Leu Asp Thr Ser Ser Leu Val
            100                 105                 110

Pro Gly Cys Ser Ser Val Asp Asn Ile Lys Ser Ser Gln Thr Ser Gln
        115                 120                 125

Asn Gln Gly Leu Gly Arg Pro Thr Leu Glu Gly Asp Glu Glu Thr Ser
    130                 135                 140

Glu Val Glu Tyr Thr Val Asn Lys Gly Pro Ala Ser Ser Asn Arg Asp
145                 150                 155                 160
```

Arg Val Pro Pro Ser Ser Glu Ala Ser Glu His His Pro Arg His Arg
                165                 170                 175

Val Ser Ser Gln Ala Glu Asp Thr Ser Ser Phe Asp Asn Leu Phe
            180                 185                 190

Ile Asp Arg Leu Gln Arg Ile Thr Ile Ala Asp Gln Gly Glu Gln Gln
                195                 200                 205

Ser Glu Glu Asn Ala Ser Thr Lys Asn Leu Thr Gly Leu Ser Ser Gly
    210                 215                 220

Thr Glu Lys Lys Pro His Tyr Met Glu Val Leu Glu Met Arg Ala Lys
225                 230                 235                 240

Asn Pro Val Pro Gln Leu Arg Lys Phe Lys Thr Asn Val Leu Pro Phe
                245                 250                 255

Arg Gln Asn Asp Ser Ser Ser His Cys Gln Lys Ser Gly Ser Pro Ile
                260                 265                 270

Ser Ser Glu Glu Arg Arg Arg Asp Lys Gln His Leu Asp Asp Ile
    275                 280                 285

Thr Ala Ala Arg Leu Leu Pro Leu His His Met Pro Thr Gln Leu Leu
    290                 295                 300

Ser Ile Glu Glu Ser Leu Ala Leu Gln Lys Gln Lys Gln Asn Tyr
305                 310                 315                 320

Glu Glu Met Gln Ala Lys Leu Ala Ala Gln Lys Leu Ala Glu Arg Leu
                325                 330                 335

Asn Ile Lys Met Arg Ser Tyr Asn Pro Glu Gly Glu Ser Ser Gly Arg
                340                 345                 350

Tyr Arg Glu Val Arg Asp Glu Asp Asp Trp Ser Ser Asp Glu Phe
    355                 360                 365

<210> SEQ ID NO 36
<211> LENGTH: 2922
<212> TYPE: DNA
<213> ORGANISM: Human

<400> SEQUENCE: 36
ccgttcttcc gggaaaatgg cgactcccgc tcgtgccccg gagtcaccgc cgtccgcgga      60
tccggcgcta gtagcggggc ctgccgagga agccgagtgc ccgccgccgc gccagcctca     120
gcccgcgcag aatgtgctcg ctgccccgcg gcttcgagcc ccaagctccc gaggacttgg     180
cgcagcggag tttggtggag ctgcgggaaa tgttgaagcg ccaggagaga cttttgcgca     240
acgaaaaatt catttgcaaa ttgcccgaca aaggtaaaaa gatctttgac tcttttgcca     300
aactgaaagc tgctattgca gaatgtgaag aagttggaag aaaaagtgaa ctgtttaacc     360
ctgttagttt agactgtaag ctaaggcaaa agcaattgc agaagttgat gtgggtacag     420
ataaggccca gaattctgac ccgatacttg atacttcatc actagttcct ggatgttcct     480
ctgtagataa catcaagtca tctcaaacct cacaaaacca gggacttgga cgtcctactc     540
ttgaaggtga tgaagagact tcagaggttg agtacacagt gaataagggc ccagcttcca     600
gcaatagaga cagggtacca ccttcatctg aagctagtga gcatcacccg cggcatcgtg     660
tttcaagtca agcggaagat acttccagca gctttgacaa cctgtttatt gacaggttac     720
agaggatcac cattgcggac caaggtgaac aacagtcaga agaaacgca agtactaaga     780 acttgacagg ccttccagt gggactgaga agaaacctca ttacatggaa gtgctagaaa     840
tgcgagccaa aaacccagtg ccccagctgc gtaaatttaa aaccaatgtg ttacctttc     900 gacaaaatga ttcatctagt cattgccaga agagtgggtc tcctatttcc tcagaagagc     960

-continued

```
ggcggcgcag ggataagcag catcttgatg acatcacagc agctcggctt ctaccacttc    1020
accatatgcc cacgcagctg ctctccatag aagaatcctt ggcacttcag aaacagcaga    1080
aacagaatta tgaggaaaga ccgttttaca gccctcagta ccgcagttcc atgaacttgc    1140
tcagcttggc agccgcagct aaggacaccc gtggtagtaa aagcgggaag atgggctccc    1200
tggctcttct taccaaactc tgattgtttg gagcagtttg accatcattt agccaggaag    1260
acaccagaag gatggcgtgc tgagagtgct agaagggaga ctgctgtccc cacaatggct    1320
gcagccccat tccttttttcc aagctgcctg ggtgaacatt ccaggatcct gacattctgt    1380
ggaaattgat gagtgcttgc tcaaaggtcg atgatgtgct acagatggca tcacctgtta    1440
gagacagagc tttctcaaga ggagctttga tttcctttac ttcccgaact gctatttcac    1500
agtctctcag tagatgtcag cagcacagca aacatctcac tgcccatcat ggaagcagga    1560
aaccgaggct ccagagagct gggtatcttt ccaaggcctt gacactggga ggtgatgagt    1620
cacggttggc tctaaagccc aagctctttt cttcacacct tgatgccgtc tagcctgtcc    1680
atggaccaat tagagccagt gaccaacagg tatatcaaaa tgacatccct cctggatggc    1740
acatcctccc cagacagcct gcccattccc tggctctgac aggctagcaa atccctgata    1800
acctcggaat gcctcaagtt gtgtcaatga agggcattga actttgatg ttggacagat    1860
gccccatgat ggatgggcac tggctgatac agtttcccac ggtgactcag aagtgcgaag    1920
gagaaaggag ggctgaggtg ccagctccag gcaggccagg caccccagat gtcagcacct    1980
gcccgactgc ctctgacata ccctcagaca tacccttttgg catgtggagc cccaggtgcc    2040
tttcttcatg tccagatagg aagactcatc ttaaggggtg tggcagcaac tgagcatgtg    2100
taccaccacc tgagctgtag ttcttgtttc tgtaagagaa aatgctccca cattatccta    2160
ctacactcta gacctcaaag gtgaggcaga gcgtgagtca agggatctga atgaaagca    2220
gttgtagtga aaagcccatg aaatatagcg ctcaagggta gctgagtctt gcaggctgta    2280
atttatgctg tttcctgctt tgagaatgta tcccaacctt ttggttacta gaaagcctca    2340
atttgaatag taaagacct gaattctggg tcctctaact tctcttcatg tgtggctcag    2400
tctaacctgt agtttaagac tcagacacca tgccttccag gaagccttcc ttgatgtctc    2460
taattctaca ttaattcctc cagtatgagc ttccacagta acttaatctt accctgaggt    2520
gtctatatca aactgcttcc tcacttgagg gaaggcacca ggtcttgttt acattttgc    2580
tctatatcac tacaacacaa gagagaatgt gataaaggtt gtaacagacc cagaaaaacc    2640
actctaggag ctctgagaag ggtagttcat gtaaatacac acacatatac atatagttca    2700
tgtaaaatata tgtatgtata cacacacaca cgcacacaca cacacacaca cacacacaca    2760
cacacagcct tcatcaagga agagattgct cttaggatgt tttcagattc aagatgctgt    2820
aaaatttgta ttgatgattg ctttctttc tatcccttgt aatttctaca cttacagctc    2880
attgattgtt cttctcatag cattaaagtc ttcagcatct gg                       2922
```

<210> SEQ ID NO 37
<211> LENGTH: 363
<212> TYPE: PRT
<213> ORGANISM: Human

<400> SEQUENCE: 37

Met Cys Ser Leu Pro Arg Gly Phe Glu Pro Gln Ala Pro Glu Asp Leu
1               5                   10                  15

Ala Gln Arg Ser Leu Val Glu Leu Arg Glu Met Leu Lys Arg Gln Glu
            20                  25                  30

```
Arg Leu Leu Arg Asn Glu Lys Phe Ile Cys Lys Leu Pro Asp Lys Gly
         35                  40                  45
Lys Lys Ile Phe Asp Ser Phe Ala Lys Leu Lys Ala Ala Ile Ala Glu
 50                  55                  60
Cys Glu Glu Val Gly Arg Lys Ser Glu Leu Phe Asn Pro Val Ser Leu
 65                  70                  75                  80
Asp Cys Lys Leu Arg Gln Lys Ala Ile Ala Glu Val Asp Val Gly Thr
                 85                  90                  95
Asp Lys Ala Gln Asn Ser Asp Pro Ile Leu Asp Thr Ser Ser Leu Val
                100                 105                 110
Pro Gly Cys Ser Ser Val Asp Asn Ile Lys Ser Ser Gln Thr Ser Gln
            115                 120                 125
Asn Gln Gly Leu Gly Arg Pro Thr Leu Glu Gly Asp Glu Glu Thr Ser
        130                 135                 140
Glu Val Glu Tyr Thr Val Asn Lys Gly Pro Ala Ser Ser Asn Arg Asp
145                 150                 155                 160
Arg Val Pro Pro Ser Ser Glu Ala Ser Glu His His Pro Arg His Arg
                165                 170                 175
Val Ser Ser Gln Ala Glu Asp Thr Ser Ser Ser Phe Asp Asn Leu Phe
            180                 185                 190
Ile Asp Arg Leu Gln Arg Ile Thr Ile Ala Asp Gln Gly Glu Gln Gln
        195                 200                 205
Ser Glu Glu Asn Ala Ser Thr Lys Asn Leu Thr Gly Leu Ser Ser Gly
210                 215                 220
Thr Glu Lys Lys Pro His Tyr Met Glu Val Leu Glu Met Arg Ala Lys
225                 230                 235                 240
Asn Pro Val Pro Gln Leu Arg Lys Phe Lys Thr Asn Val Leu Pro Phe
                245                 250                 255
Arg Gln Asn Asp Ser Ser Ser His Cys Gln Lys Ser Gly Ser Pro Ile
            260                 265                 270
Ser Ser Glu Glu Arg Arg Arg Asp Lys Gln His Leu Asp Asp Ile
        275                 280                 285
Thr Ala Ala Arg Leu Leu Pro Leu His His Met Pro Thr Gln Leu Leu
290                 295                 300
Ser Ile Glu Glu Ser Leu Ala Leu Gln Lys Gln Lys Gln Asn Tyr
305                 310                 315                 320
Glu Glu Arg Pro Phe Tyr Ser Pro Gln Tyr Arg Ser Ser Met Asn Leu
                325                 330                 335
Leu Ser Leu Ala Ala Ala Lys Asp Thr Arg Gly Ser Lys Ser Gly
            340                 345                 350
Lys Met Gly Ser Leu Ala Leu Leu Thr Lys Leu
        355                 360

<210> SEQ ID NO 38
<211> LENGTH: 753
<212> TYPE: DNA
<213> ORGANISM: Human

<400> SEQUENCE: 38
ctgccgagga agccgagtgc ccgccgccgc gccagcctca gcccgcgcag aatgtgctcg      60
ctgccccgcg gcttcgagcc ccaagctccc gaggacttgg cgcagcggag tttggtggag     120
ctgcgggaaa tgttgaagcg ccaggagaga cttttgcgca cgagttacag gaggatcacc     180
attgcggacc aaggtgaaca acagtcagaa gaaaacgcaa gtactaagaa cttgacaggc     240
```

```
cttccagtg ggactgagaa gaaacctcat tacatggaag tgctagaaat gcgagccaaa    300
aacccagtgc cccagctgcg taaatttaaa accaatgtgt taccttttcg acaaaatgat    360
tcatctagtc attgccagaa gagtgggtct cctatttcct cagaagagcg gcggcgcagg    420
gataagcagc atcttgatga catcacagca gctcggcttc taccacttca ccatatgccc    480
acgcagctgc tctccataga agaatccttg gcacttcaga aacagcagaa acagaattat    540
gaggagatgc aagcaaagct cgcagcgcaa aaattagctg aaagactgaa tattaaaatg    600
cggagttata atccagaagg ggagtcttca gggagatacc gagaagtaag ggatgaagat    660
gacgattggt cctctgatga attctgaaga taatctccta aatcactgac gttgagatgt    720
catcatctta catcagactt tctaactagt atc                                 753
```

<210> SEQ ID NO 39
<211> LENGTH: 211
<212> TYPE: PRT
<213> ORGANISM: Human

<400> SEQUENCE: 39

```
Met Cys Ser Leu Pro Arg Gly Phe Glu Pro Gln Ala Pro Glu Asp Leu
1               5                   10                  15

Ala Gln Arg Ser Leu Val Glu Leu Arg Glu Met Leu Lys Arg Gln Glu
            20                  25                  30

Arg Leu Leu Arg Asn Glu Leu Gln Arg Ile Thr Ile Ala Asp Gln Gly
        35                  40                  45

Glu Gln Gln Ser Glu Glu Asn Ala Ser Thr Lys Asn Leu Thr Gly Leu
    50                  55                  60

Ser Ser Gly Thr Glu Lys Lys Pro His Tyr Met Glu Val Leu Glu Met
65                  70                  75                  80

Arg Ala Lys Asn Pro Val Pro Gln Leu Arg Lys Phe Lys Thr Asn Val
                85                  90                  95

Leu Pro Phe Arg Gln Asn Asp Ser Ser His Cys Gln Lys Ser Gly
            100                 105                 110

Ser Pro Ile Ser Ser Glu Glu Arg Arg Arg Asp Lys Gln His Leu
        115                 120                 125

Asp Asp Ile Thr Ala Ala Arg Leu Leu Pro Leu His His Met Pro Thr
130                 135                 140

Gln Leu Leu Ser Ile Glu Glu Ser Leu Ala Leu Gln Lys Gln Lys
145                 150                 155                 160

Gln Asn Tyr Glu Glu Met Gln Ala Lys Leu Ala Ala Gln Lys Leu Ala
                165                 170                 175

Glu Arg Leu Asn Ile Lys Met Arg Ser Tyr Asn Pro Glu Gly Glu Ser
            180                 185                 190

Ser Gly Arg Tyr Arg Glu Val Arg Asp Glu Asp Asp Trp Ser Ser
        195                 200                 205

Asp Glu Phe
    210
```

<210> SEQ ID NO 40
<211> LENGTH: 1721
<212> TYPE: DNA
<213> ORGANISM: Human

<400> SEQUENCE: 40

```
ggatgctgcg ctccacgtcc acggtcaccc tgctctcggg cggcgccgcc aggacgcccg    60
```

-continued

```
gggcgcccag caggagggca aatgtttgca gactacggct gaccgtacct cctgagagtc      120
cagttcctga gcaatgtgaa aagaagattg agagaaaaga gcagcttctt gacctgagca      180
atggagaacc taccaggaaa cttcctcagg gtgttgttta tggtgtggtg cgaagatcag      240
atcaaaatca gcagaaagaa atggtggtgt atgggtggtc caccagtcag ctgaaagaag      300
agatgaacta catcaaagat gtgagagcca ctttggaaaa ggtgagaaag cgaatgtatg      360
gagactatga tgagatgaga cagaagattc gacagctcac ccaggaacta tcagtttccc      420
atgctcagca ggagtatctg gagaatcaca tccaaaccca gtcgtctgcc ctggatcgtt      480
ttaatgccat gaactcagcc ttggcgtcag attccattgg cctgcagaaa accctcgtgg      540
atgtgacttt ggaaaacagc aacattaagg atcaaatcag aaatctgcag cagacgtatg      600
aagcatccat ggacaagctg agggaaaagc agaggcagtt ggaggtagcg caagttgaaa      660
accagctgct aaaaatgaag gtggaatcgt cccaagaagc caatgctgag gtgatgcgag      720
agatgaccaa gaagctgtac agccagtatg aggagaagct gcaggaagaa cagaggaagc      780
acagtgctga aaggaggct cttttggaag aaaccaatag ttttctgaaa gcgattgaag      840
aagccaataa aaagatgcaa gcagcagaga tcagcctaga ggagaaagac cagaggatcg      900
gggagctgga caggctgatt gagcgcatgg aaaaggaacg tcatcaactg caacttcaac      960
tcctagaaca tgaaacagaa atgtctgggg agttaactga ttctgacaag gaaaggtatc     1020
agcagttgga ggaggcatca gccagcctcc gtgagcggat cagacaccta gatgacatgg     1080
tgcattgcca gcagaagaaa gtcaagcaga tggtcgagga gattgaatca ttaaagaaaa     1140
agttgcaaca gaaacagctc ttaatactgc agcttttaga aaagatatct ttcttagaag     1200
gagagaataa tgaactacaa agcaggttgg actatttaac agaaacccag gccaagactg     1260
aagtggaaac cagagagata ggagtgggct gtgatcttct acccaggtta ccttttcgac     1320
aaaatgattc atctagtcat tgccagaaga gtgggtctcc tatttcctca gaagagcggc     1380
ggcgcaggga taagcagcat cttgatgaca tcacagcagc tcggcttcta ccacttcacc     1440
atatgcccac gcagctgctc tccatagaag aatccttggc acttcagaaa cagcagaaac     1500
agaattatga ggagatgcaa gcaaagctcg cagcgcaaaa attagctgaa agactgaata     1560
ttaaaatgcg gagttataat ccagaagggg agtcttcagg gagataccga gaagtaaggg     1620
atgaagatga cgattggtcc tctgatgaat tctgaagata atctcctaaa tcactgacgt     1680
tgagatgtca tcatcttaca tcagactttc taactagtat c                         1721
```

<210> SEQ ID NO 41
<211> LENGTH: 550
<212> TYPE: PRT
<213> ORGANISM: Human

<400> SEQUENCE: 41

```
Met Leu Arg Ser Thr Ser Thr Val Thr Leu Leu Ser Gly Gly Ala Ala
1               5                   10                  15

Arg Thr Pro Gly Ala Pro Ser Arg Arg Ala Asn Val Cys Arg Leu Arg
            20                  25                  30

Leu Thr Val Pro Pro Glu Ser Pro Val Pro Glu Gln Cys Glu Lys Lys
        35                  40                  45

Ile Glu Arg Lys Glu Gln Leu Leu Asp Leu Ser Asn Gly Glu Pro Thr
    50                  55                  60

Arg Lys Leu Pro Gln Gly Val Val Tyr Gly Val Val Arg Arg Ser Asp
65                  70                  75                  80
```

```
Gln Asn Gln Gln Lys Glu Met Val Val Tyr Gly Trp Ser Thr Ser Gln
                85                  90                  95

Leu Lys Glu Glu Met Asn Tyr Ile Lys Asp Val Arg Ala Thr Leu Glu
                100                 105                 110

Lys Val Arg Lys Arg Met Tyr Gly Asp Tyr Asp Glu Met Arg Gln Lys
                115                 120                 125

Ile Arg Gln Leu Thr Gln Glu Leu Ser Val Ser His Ala Gln Gln Glu
        130                 135                 140

Tyr Leu Glu Asn His Ile Gln Thr Gln Ser Ser Ala Leu Asp Arg Phe
145                 150                 155                 160

Asn Ala Met Asn Ser Ala Leu Ala Ser Asp Ser Ile Gly Leu Gln Lys
                165                 170                 175

Thr Leu Val Asp Val Thr Leu Glu Asn Ser Asn Ile Lys Asp Gln Ile
                180                 185                 190

Arg Asn Leu Gln Gln Thr Tyr Glu Ala Ser Met Asp Lys Leu Arg Glu
        195                 200                 205

Lys Gln Arg Gln Leu Glu Val Ala Gln Val Glu Asn Gln Leu Leu Lys
        210                 215                 220

Met Lys Val Glu Ser Ser Gln Glu Ala Asn Ala Glu Val Met Arg Glu
225                 230                 235                 240

Met Thr Lys Lys Leu Tyr Ser Gln Tyr Glu Glu Lys Leu Gln Glu Glu
                245                 250                 255

Gln Arg Lys His Ser Ala Glu Lys Glu Ala Leu Leu Glu Glu Thr Asn
                260                 265                 270

Ser Phe Leu Lys Ala Ile Glu Ala Asn Lys Lys Met Gln Ala Ala
                275                 280                 285

Glu Ile Ser Leu Glu Glu Lys Asp Gln Arg Ile Gly Glu Leu Asp Arg
290                 295                 300

Leu Ile Glu Arg Met Glu Lys Glu Arg His Gln Leu Gln Leu Gln Leu
305                 310                 315                 320

Leu Glu His Glu Thr Glu Met Ser Gly Glu Leu Thr Asp Ser Asp Lys
                325                 330                 335

Glu Arg Tyr Gln Gln Leu Glu Glu Ala Ser Ala Ser Leu Arg Glu Arg
                340                 345                 350

Ile Arg His Leu Asp Asp Met Val His Cys Gln Gln Lys Lys Val Lys
                355                 360                 365

Gln Met Val Glu Glu Ile Glu Ser Leu Lys Lys Lys Leu Gln Gln Lys
        370                 375                 380

Gln Leu Leu Ile Leu Gln Leu Leu Lys Ile Ser Phe Leu Glu Gly
385                 390                 395                 400

Glu Asn Asn Glu Leu Gln Ser Arg Leu Asp Tyr Leu Thr Glu Thr Gln
                405                 410                 415

Ala Lys Thr Glu Val Glu Thr Arg Glu Ile Gly Val Gly Cys Asp Leu
                420                 425                 430

Leu Pro Arg Leu Pro Phe Arg Gln Asn Asp Ser Ser Ser His Cys Gln
                435                 440                 445

Lys Ser Gly Ser Pro Ile Ser Ser Glu Glu Arg Arg Arg Asp Lys
                450                 455                 460

Gln His Leu Asp Asp Ile Thr Ala Ala Arg Leu Leu Pro Leu His His
465                 470                 475                 480

Met Pro Thr Gln Leu Leu Ser Ile Glu Glu Ser Leu Ala Leu Gln Lys
                485                 490                 495

Gln Gln Lys Gln Asn Tyr Glu Glu Met Gln Ala Lys Leu Ala Ala Gln
```

```
                500              505              510
Lys Leu Ala Glu Arg Leu Asn Ile Lys Met Arg Ser Tyr Asn Pro Glu
            515                 520                 525
Gly Glu Ser Ser Gly Arg Tyr Arg Glu Val Arg Asp Glu Asp Asp
            530                 535             540
Trp Ser Ser Asp Glu Phe
545                 550

<210> SEQ ID NO 42
<211> LENGTH: 368
<212> TYPE: PRT
<213> ORGANISM: Human

<400> SEQUENCE: 42

Met Cys Ser Leu Pro Arg Gly Phe Glu Pro Gln Ala Pro Glu Asp Leu
1               5                   10                  15
Ala Gln Arg Ser Leu Val Glu Leu Arg Glu Met Leu Lys Arg Gln Glu
            20                  25                  30
Arg Leu Leu Arg Asn Glu Lys Phe Ile Cys Lys Leu Pro Asp Lys Gly
        35                  40                  45
Lys Lys Ile Phe Asp Ser Phe Ala Lys Leu Lys Ala Ile Ala Glu
    50                  55                  60
Cys Glu Glu Val Arg Arg Lys Ser Glu Leu Phe Asn Pro Val Ser Leu
65                  70                  75                  80
Asp Cys Lys Leu Arg Gln Lys Ala Ile Ala Glu Val Asp Val Gly Thr
                85                  90                  95
Asp Lys Ala Gln Asn Ser Asp Pro Ile Leu Asp Thr Ser Ser Leu Val
            100                 105                 110
Pro Gly Cys Ser Ser Val Asp Asn Ile Lys Ser Ser Gln Thr Ser Gln
        115                 120                 125
Asn Gln Gly Leu Gly Arg Pro Thr Leu Glu Gly Asp Glu Glu Thr Ser
    130                 135                 140
Glu Val Glu Tyr Thr Val Asn Lys Gly Pro Ala Ser Ser Asn Arg Asp
145                 150                 155                 160
Arg Val Pro Pro Ser Ser Glu Ala Ser Glu His His Pro Arg His Arg
                165                 170                 175
Val Ser Ser Gln Ala Glu Asp Thr Ser Ser Phe Asp Asn Leu Phe
            180                 185                 190
Ile Asp Arg Leu Gln Arg Ile Thr Ile Ala Asp Gln Gly Glu Gln Gln
        195                 200                 205
Ser Glu Glu Asn Ala Ser Thr Lys Asn Leu Thr Gly Leu Ser Ser Gly
    210                 215                 220
Thr Glu Lys Lys Pro His Tyr Met Glu Val Leu Glu Met Arg Ala Lys
225                 230                 235                 240
Asn Pro Val Pro Gln Leu Arg Lys Phe Lys Thr Asn Val Leu Pro Phe
                245                 250                 255
Arg Gln Asn Asp Ser Ser Ser His Cys Gln Lys Ser Gly Ser Pro Ile
            260                 265                 270
Ser Ser Glu Glu Arg Arg Arg Asp Lys Gln His Leu Asp Asp Ile
        275                 280                 285
Thr Ala Ala Arg Leu Leu Pro Leu His His Met Pro Thr Gln Leu Leu
    290                 295                 300
Ser Ile Glu Glu Ser Leu Ala Leu Gln Lys Gln Gln Lys Gln Asn Tyr
305                 310                 315                 320
```

```
Glu Glu Met Gln Ala Lys Leu Ala Ala Gln Lys Leu Ala Glu Arg Leu
                325                 330                 335

Asn Ile Lys Met Arg Ser Tyr Asn Pro Glu Gly Glu Ser Ser Gly Arg
                340                 345                 350

Tyr Arg Glu Val Arg Asp Glu Asp Asp Trp Ser Ser Asp Glu Phe
                355                 360                 365

<210> SEQ ID NO 43
<211> LENGTH: 367
<212> TYPE: PRT
<213> ORGANISM: Orangutan

<400> SEQUENCE: 43

Met Cys Ser Leu Pro Arg Gly Phe Glu Pro Gln Val Pro Glu Asp Leu
1               5                   10                  15

Glu Arg Arg Ser Leu Ala Glu Leu Arg Glu Met Leu Lys Arg Gln Glu
                20                  25                  30

Arg Leu Leu Arg Asn Glu Lys Phe Ile Cys Lys Leu Pro Asp Lys Gly
                35                  40                  45

Lys Lys Ile Phe Asp Ser Phe Ala Lys Leu Lys Ala Ala Ile Ala Glu
            50                  55                  60

Cys Glu Glu Val Arg Arg Lys Ser Glu Leu Cys His Pro Val Ser Leu
65                  70                  75                  80

Asp Cys Lys Leu Arg Gln Lys Ala Ile Ala Glu Val Asp Val Gly Thr
                85                  90                  95

Asp Lys Ala Gln Asn Ser Asp Pro Ile Leu Asp Thr Ser Ser Leu Val
                100                 105                 110

Pro Gly Cys Ser Ser Val Asp Asn Ile Lys Ser Ser Gln Thr Ser Gln
                115                 120                 125

Asn Gln Gly Leu Gly Arg Pro Thr Leu Glu Gly Asp Glu Glu Thr Ser
    130                 135                 140

Glu Val Glu Tyr Ser Val Asn Lys Gly Pro Ala Ser Ser Asn Arg Asp
145                 150                 155                 160

Arg Val Pro Pro Ser Ser Glu Ala Ser Glu Tyr His Leu Gln His Arg
                165                 170                 175

Val Ser Ser Gln Ala Glu Asp Thr Ser Ser Ser Phe Asp Asn Leu Phe
                180                 185                 190

Ile Asp Arg Leu Gln Arg Ile Thr Ile Ala Asp Gln Gly Glu Gln Gln
                195                 200                 205

Ser Glu Asn Ala Ser Thr Lys Asn Leu Thr Gly Leu Ser Ser Gly Thr
    210                 215                 220

Gln Lys Lys Pro His Tyr Met Glu Val Leu Glu Met Arg Ala Lys Asn
225                 230                 235                 240

Pro Val Pro Gln Leu His Lys Phe Lys Thr Asn Val Leu Pro Phe Arg
                245                 250                 255

Gln Asn Asp Ser Ser His Cys Gln Lys Ser Arg Ser Pro Ile Ser
                260                 265                 270

Ser Glu Glu Arg Arg Arg Arg Asp Lys Gln His Leu Asp Asp Ile Thr
                275                 280                 285

Ala Ala Arg Leu Leu Pro Leu His His Met Pro Thr Gln Leu Leu Ser
                290                 295                 300

Ile Glu Glu Ser Leu Ala Leu Gln Lys Gln Arg Lys Gln Lys Tyr Glu
305                 310                 315                 320

Glu Met Gln Ala Lys Leu Ala Ala Gln Lys Leu Ala Glu Arg Leu Asn
                325                 330                 335
```

```
Ile Lys Met Arg Ser Tyr Asn Pro Glu Gly Glu Ser Ser Gly Arg Tyr
            340                 345                 350

Arg Glu Val Arg Asp Glu Asp Asp Trp Ser Ser Asp Glu Phe
            355                 360                 365

<210> SEQ ID NO 44
<211> LENGTH: 366
<212> TYPE: PRT
<213> ORGANISM: Mouse

<400> SEQUENCE: 44

Met Phe Ser Leu Pro Arg Gly Phe Glu Pro Ala Pro Glu Asp Leu
 1               5                  10                  15

Gly Arg Gln Ser Ser Ala Glu Leu Arg Glu Arg Leu Arg Arg Gln Glu
            20                  25                  30

Arg Leu Leu Arg Asn Glu Lys Phe Ile Cys Lys Leu Pro Asp Lys Gly
            35                  40                  45

Lys Lys Ile Ser Asp Thr Val Ala Lys Leu Lys Ala Ala Ile Ser Glu
 50                  55                  60

Arg Glu Glu Val Arg Gly Arg Ser Glu Leu Phe His Pro Val Ser Val
 65                  70                  75                  80

Asp Cys Lys Leu Arg Gln Lys Ala Thr Thr Arg Ala Asp Thr Asp Val
                85                  90                  95

Asp Lys Ala Gln Ser Ser Asp Leu Met Leu Asp Thr Ser Ser Leu Val
                100                 105                 110

Pro Asp Cys Ser Ser Ile Asp Ile Lys Ser Ser Lys Ser Thr Ser Glu
                115                 120                 125

Thr Gln Gly Pro Thr His Leu Thr His Arg Gly Asn Glu Glu Thr Leu
            130                 135                 140

Glu Ala Gly Tyr Thr Val Asn Ser Ser Pro Ala Ala His Ile Arg Ala
 145                 150                 155                 160

Arg Ala Pro Ser Ser Glu Val Lys Glu His Leu Pro Gln His Ser Val
                165                 170                 175

Ser Ser Gln Glu Glu Ile Ser Ser Ile Asp Ser Leu Phe Ile
                180                 185                 190

Thr Lys Leu Gln Lys Ile Thr Ile Ala Asp Gln Ser Glu Pro Ser Glu
            195                 200                 205

Glu Asn Thr Ser Thr Glu Asn Phe Pro Glu Leu Gln Ser Glu Thr Pro
 210                 215                 220

Lys Lys Pro His Tyr Met Lys Val Leu Glu Met Arg Ala Arg Asn Pro
 225                 230                 235                 240

Val Pro Pro His Lys Phe Lys Thr Asn Val Leu Pro Thr Gln Gln
                245                 250                 255

Ser Asp Ser Pro Ser His Cys Gln Arg Gly Gln Ser Pro Ala Ser Ser
            260                 265                 270

Glu Glu Arg Arg Arg Arg Ala Arg Gln His Leu Asp Asp Ile Thr Ala
            275                 280                 285

Ala Arg Leu Leu Pro Leu His Leu Pro Ala Gln Leu Leu Ser Ile
            290                 295                 300

Glu Glu Ser Leu Ala Leu Gln Arg Glu Gln Lys Gln Asn Tyr Glu Glu
 305                 310                 315                 320

Met Gln Ala Lys Leu Ala Ala Gln Lys Leu Ala Glu Arg Leu Asn Ile
                325                 330                 335

Lys Met Gln Ser Tyr Asn Pro Glu Gly Glu Ser Ser Gly Arg Tyr Arg
```

```
                    340                 345                 350
Glu Val Arg Asp Glu Ala Asp Ala Gln Ser Ser Asp Glu Cys
            355                 360                 365

<210> SEQ ID NO 45
<211> LENGTH: 364
<212> TYPE: PRT
<213> ORGANISM: Rat

<400> SEQUENCE: 45

Met Cys Ser Leu Pro Arg Gly Phe Glu Pro Ala Pro Glu Asp Leu
1               5                   10                  15

Gly Arg Gln Ser Ser Ala Glu Leu Arg Glu Arg Leu Arg Gln Glu
                20                  25                  30

Arg Leu Leu Arg Asn Glu Lys Phe Ile Cys Lys Leu Pro Asp Lys Gly
            35                  40                  45

Lys Lys Ile Ser Asp Thr Ile Ala Lys Leu Lys Ala Ala Ile Ser Glu
        50                  55                  60

Arg Glu Glu Val Arg Gly Arg Thr Glu Leu Phe His Pro Val Ser Val
65                  70                  75                  80

Asp Cys Lys Leu Arg His Lys Ala Thr Thr Arg Val Asp Thr Asp Ile
                85                  90                  95

Asp Lys Ala Gln Asn Ser Asp Leu Met Leu Asp Thr Ser Ser Leu Val
            100                 105                 110

Pro Glu Cys Ser Ser Val Asp Ile Glu Ser Ser Lys Thr Thr Ser Glu
        115                 120                 125

Thr Gln Gly Pro Thr His Leu Thr His Lys Gly Asn Glu Glu Thr Leu
    130                 135                 140

Ala Thr Gly Cys Thr Val Asn Thr Cys Pro Ser Ala Arg Ile Thr Thr
145                 150                 155                 160

Gln Asp Pro Ser Ser Glu Val Asn Glu His Leu Pro Gln His Ser Ser
                165                 170                 175

Gln Val Glu Glu Ile Ser Ser Ser Val Asp Ser Leu Phe Ile Thr Lys
            180                 185                 190

Leu Gln Lys Ile Thr Ile Ala Asp Gln Thr Glu Pro Ser Glu Glu Asn
        195                 200                 205

Thr Ser Thr Glu Asn Phe Pro Gly Leu Gln Ser Glu Thr Pro Lys Lys
    210                 215                 220

Pro His Tyr Met Lys Val Leu Glu Met Arg Ala Lys Asn Pro Val Pro
225                 230                 235                 240

Pro Pro His Lys Phe Lys Thr Asn Val Leu Pro Thr Gln Gln Ser Asp
                245                 250                 255

Ser Ser Ser His Cys His Lys Gly Gln Ser Pro Ala Ser Ser Glu Glu
            260                 265                 270

His Arg Arg Arg Ala Arg Gln His Leu Asp Asp Val Thr Ala Ala Arg
        275                 280                 285

Leu Leu Pro Leu His His Leu Pro Ala Gln Leu Leu Ser Ile Glu Glu
    290                 295                 300

Ser Leu Ala Leu Gln Lys Glu Gln Lys Gln Asn Tyr Glu Glu Met Gln
305                 310                 315                 320

Ala Lys Leu Ala Ala Gln Lys Leu Ala Glu Arg Leu Asn Ile Lys Met
                325                 330                 335

Gln Ser Phe Asn Pro Glu Gly Glu Ser Ser Gly Arg Tyr Arg Glu Val
            340                 345                 350
```

Arg Asp Glu Asp Ala Gln Ser Ser Asp Glu Cys
        355                 360

<210> SEQ ID NO 46
<211> LENGTH: 366
<212> TYPE: PRT
<213> ORGANISM: Mouse

<400> SEQUENCE: 46

Met Phe Ser Leu Pro Arg Gly Phe Glu Pro Ala Pro Glu Asp Leu
1               5                   10                  15

Gly Arg Gln Ser Ser Ala Glu Leu Arg Glu Arg Leu Arg Arg Gln Glu
        20                  25                  30

Arg Leu Leu Arg Asn Glu Lys Phe Ile Cys Lys Leu Pro Asp Lys Gly
        35                  40                  45

Lys Lys Ile Ser Asp Thr Val Ala Lys Leu Lys Ala Ala Ile Ser Glu
    50                  55                  60

Arg Glu Glu Val Arg Gly Arg Ser Glu Leu Phe His Pro Val Ser Val
65                  70                  75                  80

Asp Cys Lys Leu Arg Gln Lys Ala Thr Thr Arg Ala Asp Thr Asp Val
                85                  90                  95

Asp Lys Ala Gln Ser Ser Asp Leu Met Leu Asp Thr Ser Ser Leu Asp
            100                 105                 110

Pro Asp Cys Ser Ser Ile Asp Ile Lys Ser Ser Lys Ser Thr Ser Glu
        115                 120                 125

Thr Gln Gly Pro Thr His Leu Thr His Arg Gly Asn Glu Glu Thr Leu
    130                 135                 140

Glu Ala Gly Tyr Thr Val Asn Ser Ser Pro Ala Ala His Ile Arg Ala
145                 150                 155                 160

Arg Ala Pro Ser Ser Glu Val Lys Glu His Leu Pro Gln His Ser Val
                165                 170                 175

Ser Ser Gln Glu Glu Ile Ser Ser Ile Asp Ser Leu Phe Ile
            180                 185                 190

Thr Lys Leu Gln Lys Ile Thr Ile Ala Asp Gln Ser Glu Pro Ser Glu
        195                 200                 205

Glu Asn Thr Ser Thr Glu Asn Phe Pro Glu Leu Gln Ser Glu Thr Pro
    210                 215                 220

Lys Lys Pro His Tyr Met Lys Val Leu Glu Met Arg Ala Arg Asn Pro
225                 230                 235                 240

Val Pro Pro Pro His Lys Phe Lys Thr Asn Val Leu Pro Thr Gln Gln
                245                 250                 255

Ser Asp Ser Pro Ser His Cys Gln Arg Gly Gln Ser Pro Ala Ser Ser
            260                 265                 270

Glu Glu Gln Arg Arg Arg Ala Arg Gln His Leu Asp Asp Ile Thr Ala
        275                 280                 285

Ala Arg Leu Leu Pro Leu His His Leu Pro Ala Gln Leu Leu Ser Ile
    290                 295                 300

Glu Glu Ser Leu Ala Leu Gln Arg Glu Gln Lys Gln Asn Tyr Glu Glu
305                 310                 315                 320

Met Gln Ala Lys Leu Ala Ala Gln Lys Leu Ala Glu Arg Leu Asn Ile
                325                 330                 335

Lys Met Gln Ser Tyr Asn Pro Glu Gly Glu Ser Ser Gly Arg Tyr Arg
            340                 345                 350

Glu Val Arg Asp Glu Ala Asp Ala Gln Ser Ser Asp Glu Cys
        355                 360                 365

<210> SEQ ID NO 47
<211> LENGTH: 366
<212> TYPE: PRT
<213> ORGANISM: Frog

<400> SEQUENCE: 47

```
Met Phe Ser Leu Pro Arg Gly Phe Glu Pro Ala Pro Glu Asp Leu
1               5                   10                  15

Gly Arg Gln Ser Ser Ala Glu Leu Arg Glu Arg Leu Arg Arg Gln Glu
            20                  25                  30

Arg Leu Leu Arg Asn Glu Lys Phe Ile Cys Lys Leu Pro Asp Lys Gly
            35                  40                  45

Lys Lys Ile Ser Asp Thr Val Ala Lys Leu Lys Ala Ala Ile Ser Glu
50                  55                  60

Arg Glu Glu Val Arg Gly Arg Ser Glu Leu Phe His Pro Val Ser Val
65                  70                  75                  80

Asp Cys Lys Leu Arg Gln Lys Ala Thr Thr Arg Ala Asp Thr Asp Val
                85                  90                  95

Asp Lys Ala Gln Ser Ser Asp Leu Met Leu Asp Thr Ser Ser Leu Asp
            100                 105                 110

Pro Asp Cys Ser Ser Ile Asp Ile Lys Ser Ser Lys Ser Thr Ser Glu
            115                 120                 125

Thr Gln Gly Pro Thr His Leu Thr His Arg Gly Asn Glu Glu Thr Leu
            130                 135                 140

Glu Ala Gly Tyr Thr Val Asn Ser Ser Pro Ala Ala His Ile Arg Ala
145                 150                 155                 160

Arg Ala Pro Ser Ser Glu Val Lys Glu His Leu Pro Gln His Ser Val
                165                 170                 175

Ser Ser Gln Glu Glu Glu Ile Ser Ser Ser Ile Asp Ser Leu Phe Ile
            180                 185                 190

Thr Lys Leu Gln Lys Ile Thr Ile Ala Asp Gln Ser Glu Pro Ser Glu
            195                 200                 205

Glu Asn Thr Ser Thr Glu Asn Phe Pro Glu Leu Gln Ser Glu Thr Pro
210                 215                 220

Lys Lys Pro His Tyr Met Lys Val Leu Glu Met Arg Ala Arg Asn Pro
225                 230                 235                 240

Val Pro Pro Pro His Lys Phe Lys Thr Asn Val Leu Pro Thr Gln Gln
                245                 250                 255

Ser Asp Ser Pro Ser His Cys Gln Arg Gly Gln Ser Pro Ala Ser Ser
            260                 265                 270

Glu Glu Gln Arg Arg Ala Arg Gln His Leu Asp Asp Ile Thr Ala
            275                 280                 285

Ala Arg Leu Leu Pro Leu His His Leu Pro Ala Gln Leu Leu Ser Ile
290                 295                 300

Glu Glu Ser Leu Ala Leu Gln Arg Gly Gln Lys Gln Asn Tyr Glu Glu
305                 310                 315                 320

Met Gln Ala Lys Leu Ala Ala Gln Lys Leu Ala Glu Arg Leu Asn Ile
                325                 330                 335

Lys Met Gln Ser Tyr Asn Pro Glu Gly Glu Ser Ser Gly Arg Tyr Arg
            340                 345                 350

Glu Val Arg Asp Glu Ala Asp Ala Gln Ser Ser Asp Glu Cys
            355                 360                 365
```

<210> SEQ ID NO 48
<211> LENGTH: 320
<212> TYPE: DNA
<213> ORGANISM: Bovine

<400> SEQUENCE: 48

| ttctgatgtt | ggagcgcccg | catttgtttt | tttttttttt | ttttctgaaa | aatcccccccc | 60 |
| ctccccttt | ttcctggttt | aagaagataa | tagtgtatta | tcgctctgaa | gccattagat | 120 |
| ggcagataaa | aagccccctt | tcaatatgtg | ggtttgattt | tttttttttt | aaagcccaca | 180 |
| cgaaaagagg | agggcgcaag | gcaaagctgt | aagagttatt | ccagaacctg | gggaaatcac | 240 |
| ttagggcaat | aaaaaaaaca | cttcagggta | caaaaaagct | cgactacaca | tttccgtttt | 300 |
| cttccttgaa | aacacgacat | | | | | 320 |

<210> SEQ ID NO 49
<211> LENGTH: 741
<212> TYPE: DNA
<213> ORGANISM: Bovine

<400> SEQUENCE: 49

| aaaatggcga | ctcccgctcg | ttcgccggag | tccccgccgg | ccgcggatct | ggcgccagct | 60 |
| acggggctg | ccgaggacgc | cgagtgccca | ccgcctcgcc | agcctcagcc | cctgcagaat | 120 |
| gtcctcgctg | ccccgcggct | tcgagcccca | aactcccgag | gacttggggc | agcggagttt | 180 |
| ggcggagcta | cgggaaatgt | tgaagcgcca | ggagagactt | tgcgcaacg | taaaattcat | 240 |
| ttgcaaattg | cccgacaaag | gtaaaaagat | ctcagacgcg | gtcaccaaac | tgaaagctgc | 300 |
| catcgcagaa | cgtgaagaag | ttagaggaag | aagtgaactc | ttttatcctg | ttagcttaga | 360 |
| ctgtaaggag | aggcaaaaag | cgattgcagt | tgttgatggg | gaccgagata | aggcccagaa | 420 |
| ttctgaccag | atacttgaca | cttcatcacc | cgttcctggc | tgttcctctg | tagctaacat | 480 |
| cacatcatct | cagacaacct | cacgacaaca | gggactggca | catccaactc | gaggaggtga | 540 |
| tgctgaggca | gctgaggctg | aacacacagt | gagcgagcac | ccaacttcta | gcagcggagc | 600 |
| cccagcgcct | tcctcatctc | aagctagtga | gggtctccct | cagcattgtg | ccttacgtca | 660 |
| agtggaggat | catcctggca | gctcagacaa | cctgttcatt | gatagattac | aaaggatcac | 720 |
| aagtgcggat | ccgactgaac | a | | | | 741 |

<210> SEQ ID NO 50
<211> LENGTH: 970
<212> TYPE: DNA
<213> ORGANISM: Bovine

<400> SEQUENCE: 50

| gaaggaaacc | ggaatcctga | gaacttggcc | ggcctctgga | gtgggccgca | gaagaagcct | 60 |
| cattacatgg | aagtgctgga | aatgcgagcc | aaaaatccca | tgcccccgcc | acataaattt | 120 |
| aaaaccaatg | tattaccttc | acagccccgt | gattcatcga | gtgcttgtca | gaggagaggg | 180 |
| tctcccatct | cctcagagga | gaggcggcgc | agggacagga | agcatcttga | tgatatcaca | 240 |
| gcggcccggc | ttctgccgct | gcaccacctg | ccaacccagc | tgctctccat | agaggagtcg | 300 |
| ctggcacttc | agagacagca | gaagcagagt | tatgaggaga | tacaagccaa | gctcgcagca | 360 |
| cagaagctag | ctgaaagact | aaatattaaa | atgcagagct | ataatccaga | aggggagtct | 420 |
| tcaaggaaat | accgagaagt | aagggatgaa | gatgatgatc | agtcctccga | ggatgaattc | 480 |
| tgaagatgga | tgttcagatt | atctcctaaa | tctctgcctg | ttgagatctc | attatcttac | 540 |

```
atcagagtgc ctaacaagta tcaagatcag tgtcagacat tgttgagaga aagaattttg    600
taaagttaca ctaaggaaac tataaaaaga gcccactttc agatgataac tttcatgtgc    660
ttgaaaagtt gaatatttga atattgtgtt taatgacact atattaaatt ttggcagtat    720
gtcctgtgtt ggtctgatat tttagtatat agtaagcaca ttttttttctc aaagccaaat   780 gaaagcaggt gattaaactg ctttttttctt tatacttacc tctaccaaat aatgtttatt   840
acatgtctta gtgaattatt tagtttccca ggcatcacct aaaatgagtt atgaagatat    900
agttccctct ttttttgaag aacaagggaa gaagtctaga gaattttgtg catgtttgca    960
tgggggctgt                                                           970
```

<210> SEQ ID NO 51
<211> LENGTH: 370
<212> TYPE: PRT
<213> ORGANISM: Bovine

<400> SEQUENCE: 51

```
Met Ser Ser Leu Pro Arg Gly Phe Glu Pro Gln Thr Pro Glu Asp Leu
1               5                   10                  15

Gly Gln Arg Ser Leu Ala Glu Leu Arg Glu Met Leu Lys Arg Gln Glu
            20                  25                  30

Arg Leu Leu Arg Asn Val Lys Phe Ile Cys Lys Leu Pro Asp Lys Gly
        35                  40                  45

Lys Lys Ile Ser Asp Ala Val Thr Lys Leu Lys Ala Ala Ile Ala Glu
    50                  55                  60

Arg Glu Glu Val Arg Gly Arg Ser Glu Leu Phe Tyr Pro Val Ser Leu
65                  70                  75                  80

Asp Cys Lys Glu Arg Gln Lys Ala Ile Ala Val Val Asp Gly Asp Arg
                85                  90                  95

Asp Lys Ala Gln Asn Ser Asp Gln Ile Leu Asp Thr Ser Ser Pro Val
            100                 105                 110

Pro Gly Cys Ser Ser Val Ala Asn Ile Thr Ser Ser Gln Thr Thr Ser
        115                 120                 125

Arg Gln Gln Gly Leu Ala His Pro Thr Arg Gly Gly Asp Ala Glu Ala
    130                 135                 140

Ala Glu Ala Glu His Thr Val Ser Glu His Pro Thr Ser Ser Ser Gly
145                 150                 155                 160

Ala Pro Ala Pro Ser Ser Ser Gln Ala Ser Glu Gly Leu Pro Gln His
                165                 170                 175

Cys Ala Leu Arg Gln Val Glu Asp His Pro Gly Ser Ser Asp Asn Leu
            180                 185                 190

Phe Ile Asp Arg Leu Gln Arg Ile Thr Ser Ala Asp Pro Thr Glu His
        195                 200                 205

His Ser Glu Gly Asn Arg Asn Pro Glu Asn Leu Ala Gly Leu Trp Ser
    210                 215                 220

Gly Pro Gln Lys Lys Pro His Tyr Met Glu Val Leu Glu Met Arg Ala
225                 230                 235                 240

Lys Asn Pro Met Pro Pro His Lys Phe Lys Thr Asn Val Leu Pro
                245                 250                 255

Ser Gln Pro Arg Asp Ser Ser Ala Cys Gln Arg Arg Gly Ser Pro
            260                 265                 270

Ile Ser Ser Glu Glu Arg Arg Arg Asp Arg Lys His Leu Asp Asp
        275                 280                 285

Ile Thr Ala Ala Arg Leu Leu Pro Leu His His Leu Pro Thr Gln Leu
```

```
              290                 295                 300
Leu Ser Ile Glu Glu Ser Leu Ala Leu Gln Arg Gln Gln Lys Gln Ser
305                 310                 315                 320

Tyr Glu Glu Ile Gln Ala Lys Leu Ala Ala Gln Lys Leu Ala Glu Arg
                325                 330                 335

Leu Asn Ile Lys Met Gln Ser Tyr Asn Pro Glu Gly Glu Ser Ser Arg
            340                 345                 350

Lys Tyr Arg Glu Val Arg Asp Glu Asp Asp Gln Ser Ser Glu Asp
                355                 360                 365

Glu Phe
    370

<210> SEQ ID NO 52
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 52

Ala Ala Ile Ala Glu Arg Glu Glu Val Arg Gly Arg Ser Glu Leu Phe
1               5                   10                  15

Tyr Pro Val

<210> SEQ ID NO 53
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 53

Met Gln Xaa Tyr Asn Pro Glu Gly Glu
1               5

<210> SEQ ID NO 54
<211> LENGTH: 25
<212> TYPE: PRT
<213> ORGANISM: Artificial Sequence
<220> FEATURE:
<223> OTHER INFORMATION: chemically synthesized

<400> SEQUENCE: 54

Lys Leu Lys Ala Ala Ile Ala Glu Cys Glu Glu Val Arg Arg Lys Ser
1               5                   10                  15

Glu Leu Phe Asn Pro Val Ser Leu Asp
            20                  25

<210> SEQ ID NO 55
<211> LENGTH: 15
<212> TYPE: PRT
<213> ORGANISM: Artificial Sequence
<220> FEATURE:
<223> OTHER INFORMATION: chemically synthesized

<400> SEQUENCE: 55

Asn Ile Lys Met Arg Ser Tyr Asn Pro Glu Gly Glu Ser Ser Gly
1               5                   10                  15
```

```
<210> SEQ ID NO 56
<211> LENGTH: 25
<212> TYPE: PRT
<213> ORGANISM: Artificial Sequence
<220> FEATURE:
<223> OTHER INFORMATION: chemically synthesized

<400> SEQUENCE: 56

Lys Leu Lys Ala Ala Ile Ala Glu Cys Glu Glu Val Gly Arg Lys Ser
1               5                   10                  15

Glu Leu Phe Asn Pro Val Ser Leu Asp
            20                  25

<210> SEQ ID NO 57
<211> LENGTH: 15
<212> TYPE: PRT
<213> ORGANISM: Artificial Sequence
<220> FEATURE:
<223> OTHER INFORMATION: chemically synthesized

<400> SEQUENCE: 57

Leu Ser Leu Ala Ala Ala Ala Lys Asp Thr Arg Gly Ser Lys Ser
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: chemically synthesized

<400> SEQUENCE: 58

Asn Ile Lys Met Arg Ser Tyr Asn Pro Glu Gly Glu Ser Ser Gly
1               5                   10                  15

<210> SEQ ID NO 59
<211> LENGTH: 25
<212> TYPE: PRT
<213> ORGANISM: Artificial Sequence
<220> FEATURE:
<223> OTHER INFORMATION: chemically synthesized

<400> SEQUENCE: 59

Glu Met Arg Gln Lys Ile Arg Gln Leu Thr Gln Glu Leu Ser Val Ser
1               5                   10                  15

His Ala Gln Gln Glu Tyr Leu Glu Asn
            20                  25

<210> SEQ ID NO 60
<211> LENGTH: 15
<212> TYPE: PRT
<213> ORGANISM: Artificial Sequence
<220> FEATURE:
<223> OTHER INFORMATION: chemically synthesized

<400> SEQUENCE: 60

Asn Ile Lys Met Arg Ser Tyr Asn Pro Glu Gly Glu Ser Ser Gly
1               5                   10                  15

<210> SEQ ID NO 61
<211> LENGTH: 19
<212> TYPE: PRT
<213> ORGANISM: Artificial Sequence
<220> FEATURE:
<223> OTHER INFORMATION: chemically synthesized

<400> SEQUENCE: 61
```

```
Ala Ala Ile Ala Glu Arg Glu Glu Val Arg Gly Arg Ser Glu Leu Phe
1               5                   10                  15

Tyr Pro Val

<210> SEQ ID NO 62
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: misc_feature
<222> LOCATION: (3)..(3)
<223> OTHER INFORMATION: Xaa can be any naturally occurring amino acid

<400> SEQUENCE: 62

Met Gln Xaa Tyr Asn Pro Glu Gly Glu
1               5

<210> SEQ ID NO 63
<211> LENGTH: 25
<212> TYPE: PRT
<213> ORGANISM: Human

<400> SEQUENCE: 63

Lys Leu Lys Ala Ala Ile Ala Glu Cys Glu Glu Val Arg Arg Lys Ser
1               5                   10                  15

Glu Leu Phe Asn Pro Val Ser Leu Asp
            20                  25

<210> SEQ ID NO 64
<211> LENGTH: 15
<212> TYPE: PRT
<213> ORGANISM: Human

<400> SEQUENCE: 64

Asn Ile Lys Met Arg Ser Tyr Asn Pro Glu Gly Glu Ser Ser Gly
1               5                   10                  15

<210> SEQ ID NO 65
<211> LENGTH: 25
<212> TYPE: PRT
<213> ORGANISM: Orangutan

<400> SEQUENCE: 65

Lys Leu Lys Ala Ala Ile Ala Glu Cys Glu Glu Val Arg Arg Lys Ser
1               5                   10                  15

Glu Leu Cys His Pro Val Ser Leu Asp
            20                  25

<210> SEQ ID NO 66
<211> LENGTH: 15
<212> TYPE: PRT
<213> ORGANISM: Orangutan

<400> SEQUENCE: 66

Asn Ile Lys Met Arg Ser Tyr Asn Pro Glu Gly Glu Ser Ser Gly
1               5                   10                  15

<210> SEQ ID NO 67
<211> LENGTH: 25
<212> TYPE: PRT
<213> ORGANISM: Mouse
```

-continued

```
<400> SEQUENCE: 67

Lys Leu Lys Ala Ala Ile Ser Glu Arg Glu Glu Val Arg Gly Arg Ser
1               5                   10                  15

Glu Leu Phe His Pro Val Ser Val Asp
            20                  25

<210> SEQ ID NO 68
<211> LENGTH: 15
<212> TYPE: PRT
<213> ORGANISM: Mouse

<400> SEQUENCE: 68

Asn Ile Lys Met Gln Ser Tyr Asn Pro Glu Gly Glu Ser Ser Gly
1               5                   10                  15

<210> SEQ ID NO 69
<211> LENGTH: 25
<212> TYPE: PRT
<213> ORGANISM: Frog

<400> SEQUENCE: 69

Lys Leu Lys Ala Ala Ile Ser Glu Arg Glu Glu Val Arg Gly Arg Ser
1               5                   10                  15

Glu Leu Phe His Pro Val Ser Val Asp
            20                  25

<210> SEQ ID NO 70
<211> LENGTH: 15
<212> TYPE: PRT
<213> ORGANISM: Frog

<400> SEQUENCE: 70

Asn Ile Lys Met Gln Ser Tyr Asn Pro Glu Gly Glu Ser Ser Gly
1               5                   10                  15

<210> SEQ ID NO 71
<211> LENGTH: 25
<212> TYPE: PRT
<213> ORGANISM: Rat

<400> SEQUENCE: 71

Lys Leu Lys Ala Ala Ile Ser Glu Arg Glu Glu Val Arg Gly Arg Thr
1               5                   10                  15

Glu Leu Phe His Pro Val Ser Val Asp
            20                  25

<210> SEQ ID NO 72
<211> LENGTH: 15
<212> TYPE: PRT
<213> ORGANISM: Rat

<400> SEQUENCE: 72

Asn Ile Lys Met Gln Ser Phe Asn Pro Glu Gly Glu Ser Ser Gly
1               5                   10                  15

<210> SEQ ID NO 73
<211> LENGTH: 25
<212> TYPE: PRT
<213> ORGANISM: Bovine

<400> SEQUENCE: 73

Lys Leu Lys Ala Ala Ile Ala Glu Arg Glu Glu Val Arg Gly Arg Ser
1               5                   10                  15
```

-continued

```
Glu Leu Phe Tyr Pro Val Ser Leu Asp
            20                  25

<210> SEQ ID NO 74
<211> LENGTH: 15
<212> TYPE: PRT
<213> ORGANISM: Bovine

<400> SEQUENCE: 74

Asn Ile Lys Met Gln Ser Tyr Asn Pro Glu Gly Glu Ser Ser Arg
1               5                   10                  15

<210> SEQ ID NO 75
<211> LENGTH: 19
<212> TYPE: PRT
<213> ORGANISM: Artificial Sequence
<220> FEATURE:
<223> OTHER INFORMATION: Peptide

<400> SEQUENCE: 75

Ala Ala Ile Ala Glu Arg Glu Glu Val Arg Gly Arg Ser Glu Leu Phe
1               5                   10                  15

Tyr Pro Val

<210> SEQ ID NO 76
<211> LENGTH: 9
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 76

Met Gln Xaa Tyr Asn Pro Glu Gly Glu
1               5
```

TFIIS AND GDOWN1 AS TARGETS FOR CANCER THERAPY

This application claims priority to U.S. Provisional Patent Application Ser. No. 60/782,203, filed Mar. 14, 2006, which is incorporated by reference herein in its entirety.

STATEMENT REGARDING FEDERALLY SPONSORED RESEARCH OR DEVELOPMENT

The present invention was developed at least in part with funds from National Institutes of Health Grant GM64474-01. The United States Government may have certain rights in the invention.

FIELD OF THE INVENTION

The present invention generally concerns the fields of molecular biology, cell biology, cancer therapy, and medicine. In specific embodiments, the field of the invention concerns inhibition of transcription for the therapy of cancer.

BACKGROUND OF THE INVENTION

Cancer presents a major public health issue concerning the significant number of affected individuals and the relatively high mortality rates, including for many diseases of origin. Breast and prostate cancers rank among the cancers with the highest incidence and morbidity (Weir et al, 2003). Both cancers are initially hormone-dependent with prostate cancer cells activated by androgen, which binds the androgen receptor (AR), and breast cancer cells activated by estrogen, which binds the Estrogen receptor (ER). Both forms of cancer respond to anti-hormone therapy. In time, though, hormone-independent cancers develop and remain a serious challenge to therapy. Clearly, a key underlying mechanism of breast and prostate cancer, including the switch of breast and prostate cancer to hormone independence, is improper control of transcription. This results in increased levels of c-myc in both prostate and breast cancers (Chrzan et al., 2001; Ellwood-Yen et al., 2003). Numerous other genes are also upregulated or downregulated (Gelmann and Semmes, 2004).

Considering the key function of transcription, it is no surprise that several best-selling drugs approved in the United States target transcription regulatory circuits (Emery et al., 2001). However, methods for directed targeting of core transcription components by therapeutic agents have yet to be established. The challenge thereof is in the complexity of the machinery, and in purification of large amounts of high-quality RNA mammalian Polymerase II (RNAP). To date RNAP, the eukaryotic motor of transcription involved in generating all mRNA, has been produced with low yields and in a relatively impure state (Thompson et al., 1990). However, assay development involving RNAP and its interacting factors require high yields and highly pure proteins.

Mammalian RNAP comprises 12 polypeptides with a mass of over 500 kD. Regulation of this complex can occur during initiation, elongation of the RNA transcript, or termination of the process. In addition, gene expression is dependent upon the structure of DNA, such as the positioning of nucleosomes, which is a basic structural unit comprised of DNA and histones (Belotserkovskaya et al., 2004; Khorasanizadeh, 2004). DNA-binding transcription factors are also involved in effectuating an increase or decrease in gene expression.

One such DNA-binding transcription factor over-expressed in breast and prostate cancers is the c-myc oncogene (Jenkins et al., 1997). Myc is a major player in prostate cancer, as evidenced by transgenic mice expressing human c-Myc in the mouse prostate. All transgenic mice developed murine prostatic intraepithelial neoplasia followed by invasive adenocarcinoma (Ellwood-Yen et al., 2003). Indeed, growth of human androgen-independent prostate cancer (AIPC) cells, androgen recepter (AR)-positive or -negative, requires c-myc expression (Bernard et al., 2003). In breast cancer c-myc plays an equally important role and is also amplified and overexpressed (Blancato et al., 2004).

C-myc may have its effect by altering downstream cellular processes. For example, it was suggested that up-regulation of telomerase activity observed in prostate tumors might be conferred through stimulation of telomerase catalytic subunit expression by c-myc. (Latil et al., 2000). It was also shown that the involvement of myc may be directly on the androgen receptor gene, as a Myc consensus site in the AR coding region is involved in androgen-mediated up-regulation of AR messenger RNA (Grad et al, 1999).

Since over-expression of c-myc exists in uncontrolled breast and prostate cancer proliferation, gene therapy strategies that employ expression of c-myc antisense have been attempted. In one such case, a single direct injection of MMTV-antisense c-myc viral media into established DU145 tumors in nude mice resulted in a 94.5% reduction in tumor size compared to controls, with two animals having complete regression. The mechanism for the anti-tumor effects was suppression of c-myc mRNA resulting in down-regulation of the bcl-2 protein. (Steiner et al., 1998). Other efforts include the use of antisense phosphorodiamidate morpholino oligomers directed against c-myc in a PC-3 androgen-independent human prostate cancer xenograft murine model and testing for safety in a Phase I human clinical study. A 75-80% reduction in tumor size was observed in treated animals compared with control groups. Safety trials in humans showed no toxicity or serious adverse events, and phase II trials are underway (Iversen et al., 2003).

TFIIS: A Putative Transcription Factor Target Upstream of c-myc

C-myc is overexpressed in breast and prostate cancer and is targeted for therapy. Interestingly, regulation of c-myc expression can occur during elongation of the growing RNA strand (Keene et al., 1999). During transcription of the Myc gene, RNAP must traverse polyT stretches in the DNA, which are known to cause arresting of transcription. This arresting is regulated by the transcription factor TFIIS, which directly binds RNAP allowing for read through of the PolyT stretch. Arresting of c-myc during transcription elongation has been shown, and poly T sequences that are TFIIS responsive in c-myc are the key intrinsic factor in arresting (Keene et al., 1999; Bains et al., 1997; Kerppola and Kane, 1988; Kerppola and Kane, 1990; Astrom et al., 1999). In addition, TFIIS is considered a candidate gene for human malignancies involving deletions in the chromosomal region, 3p21.3→3p22 TFIIS (Astrom et al., 1999). TFIIS is therefore a good target for cancer drug development, including breast and prostate cancer drug development.

Another overexpressed breast cancer-related protein is c-fos. c-fos is critical for MCF7 breast cancer cell growth and is an effective target for a breast cancer vaccine (Lu et al., 2005; Luo et al., 2003). c-fos is reported to contain a poly T arrest site similar to that of c-myc (Plet et al., 1995). TFIIS allows for readthrough of poly T tracts and, as a result, its inhibition may reduce c-fos expression.

Targeting Transcription and Potential Toxicology of Non-cancerous Cells

A fair question concerning toxicological effects of inhibiting higher order transcription factors is in place. By inhibiting transcription factors, both normal and cancer cells may be affected. Insight from clinical trials involving the inhibition of higher order transcription factors sheds light on this issue.

One such case involves the HDAC (histone deacetylase) inhibitors. As mentioned above, nucleosome positioning is a key part of chromosomal structure, and acetylation or de-acetylation of the histone component of nucleosomes affects transcription. Inhibitors to HDACs cause cell cycle arrest, differentiation and/or apoptosis of many tumors, which may be useful for chemotherapy (Yoshida et al., 2003), and they are in clinical trials (Leone et al., 2003). Apparently, HDAC inhibitors have shown impressive antitumor activity in vivo with remarkably little toxicity in preclinical studies (Vigushin and Coombes, 2002). Other chromatin-remodeling transcription factors may therefore also be valid targets for cancer therapy, such as the SWI/SNF chromatin remodeling complex (Reyes et al., 1997). As such, a global regulator is shown to present clinically with little toxicity despite affecting transcription of numerous genes.

A second case is Flavopiridol, a kinase and higher order transcription inhibitor (Kelly et al., 2002). One of its targets, pTEFb, like TFIIS, is a transcription elongation factor that directly interacts and phosphorlyates RNAP. Flavopirodol inhibits transcript elongation, effectively eliminating transcription, yet it is well tolerated in clinical trials as an anti-cancer agent (Aklilu et al., 2003). Flavopiridol, though, inhibits several cell cycle kinases, and a search for drugs that specifically affect transcription elongation alone is in need. Interestingly, even siRNA inhibition of RNAP itself is tolerated in animal models (Fluiter et al., 2003).

One reason why transcription inhibition may be tolerated is that normal cells can maintain homeostasis after transcription factor inhibition for some period of time, whereas cancer cells may require the state of aberrant transcription to survive. Disrupted transcriptional homeostasis or reduced amounts of oncogenic proteins may cause either differentiation or apoptosis as it has in the case of a conditional Myc model (Jain et al., 2002). In addition, inhibiting specific transcription factors may shut down only a subset of genes. For example, yeast cells with TFIIS deletions are viable (Nakanishi et al., 1995).

WO 98/41648 concerns methods of inhibiting growth of a cell by administering inhibitors active on an allele of a gene that is vital for cell growth and viability, and the reference provides a list of potential genes, including some transcription factors.

WO 01/72777 relates to methods for treating disease associated with decreased or increased expression of a transcription factor by administering an antagonist or agonist to a particular polypeptide, including transcription factors.

WO 02/22660 is directed to methods to treat individuals by administering an antibody to particular gene products, including transcription factors.

The present invention satisfies a need to provide novel targets in the challenging field of cancer therapeutics.

BRIEF SUMMARY OF THE INVENTION

The present invention is directed to a system, method, and/or compositions that are useful for cancer therapy and/or prevention. In particular embodiments of the invention, core transcription factors are targeted for effective cancer treatment. In specific embodiments, altering a key regulatory control system in cells with one or more inhibitors to at least one component of the system allows for treatment of any cancer, including breast, prostate, lung, and pancreatic cancer, for example.

In particular, the present invention concerns the core transcription factors of TFIIS and GDOWN1. TFIIS is a known transcription factor, and GDOWN1 has been identified by the inventors as a thirteenth subunit of RNA polymerase (RNAP); cancer cells die when either are depleted.

In certain embodiments, the present invention is based on TFIIS and/or GDOWN1 as cancer targets, including targets for breast cancer, prostate cancer, lung cancer and/or pancreatic cancer, for example. TFIIS is a transcription elongation factor required for efficient expression, such as of the c-myc gene, for example. It is demonstrated herein that inhibition of TFIIS, such as by using siRNA, for example, results in cancer cell death, such as via apoptosis. Furthermore, the ability to produce large amounts of ultrapure mammalian RNAP and the availability of other transcription factors facilitate high throughput assay development and analysis. More specifically, biochemical assays in hand for TFIIS provide a convenient way to design a specific high throughput screen for small molecule inhibitors.

In particular aspects of the invention, the therapy may be utilized for any cancer, but in specific embodiments it is for breast, lung, pancreatic and/or prostate cancer. Other examples of cancers that the inventive therapy may be utilized for include brain, liver, stomach, colon, ovarian, cervical, spleen, testical, esophageal, bone, blood, kidney, thyroid, skin, and/or gall bladder cancer. The cancer may comprise solid tumors or may not comprise solid tumors, such as with leukemia or lymphoma, for example.

The present invention provides that cancer cells die when the transcription factor TFIIS is not functioning, although non-cancerous cells are not deleteriously affected. Therefore, TFIIS is employed as a cancer target. This is in contrast to conventional wisdom, which would assume that with targeting of a core transcription factor and binding to RNAP, transcription would be rendered ineffective and kill every cell indiscriminately. However, it is known that two drugs that affect core transcription, flavopiridol and HDAC (human deacetylase enzymes), have few side effects in clinical trials. In particular, depleting cells of TFIIS and/or GDOWN1, such as by siRNA, for example, results in killing of at least some of breast, prostate, lung and pancreatic cells, and in some cases the vast majority of the cancer cells are killed.

The present invention also provides an assay to identify TFIIS and/or GDOWN1 inhibitors. In particular aspects, the assay is a high throughput assay and may utilize one or more activities and/or characteristics of TFIIS and/or GDOWN1 as the focus of the assay. For example, the assay may be interpreted using readout of RNAP-mediated transcription, expression of TFIIS and/or GDOWN1, respectively, and/or activity of TFIIS and/or GDOWN1, respectively, for example.

In an embodiment of the invention, there is a method of inhibiting proliferation of at least one cancer cell, comprising delivering to the cell an effective amount of a composition comprising an agent that inhibits TFIIS and/or GDOWN1. In specific embodiments, the agent is further defined as an agent that inhibits proliferation of the cancer cell but does not inhibit proliferation of a non-cancerous cell. The agent may comprise nucleic acid, such as siRNA, for example, including wherein the siRNA comprises SEQ ID NO:7, SEQ ID NO:10, or a mixture thereof, for example. The agent may comprise a polypeptide or peptide or a small molecule. In specific embodiments, the cancer cell is a breast cancer cell, a prostate cancer cell, a lung cancer cell, or a pancreatic cancer cell. In further specific embodiments, the cell is in a human. In some aspects of the invention, the human is further provided one or more additional anti-cancer therapies, such as chemotherapy, radiotherapy, immunotherapy, gene therapy, surgery, or a combination thereof, for example. In particular aspects, the agent inhibits TFIIS expression, TFIIS activity, or both, or GDOWN1 expression, GDOWN1 activity, or both.

In another embodiment, there is a method of manufacturing a TFIIS inhibitor or a GDOWN1 inhibitor comprising: (a) providing a candidate substance suspected of decreasing TFIIS expression or activity or GDOWN1 expression or activity, respectfully; (b) selecting the respective TFIIS inhibitor or GDOWN1 inhibitor by assessing the ability of the candidate substance to decrease TFIIS expression or activity or GDOWN1 expression or activity, respectively; and (c) manufacturing the selected respective TFIIS inhibitor or GDOWN1 inhibitor. In a specific embodiment, the candidate substance comprises a small molecule, a polypeptide, a peptide, or a nucleic acid molecule. In some embodiments, the providing step is further defined as providing in a cell or a cell-free system a TFIIS polypeptide and the TFIIS polypeptide is contacted with the candidate substance. In particular aspects, the providing step is further defined as providing a nucleic acid molecule that encodes the TFIIS polypeptide. The candidate substance may be a small molecule, a protein, such as an antibody that binds immunologically to TFIIS, a peptide, a nucleic acid molecule, such as an antisense molecule, including an siRNA molecule (for example SEQ ID NO:7, SEQ ID NO:10, or a mixture thereof). In further embodiments, the method further comprises administering the inhibitor to an individual with cancer or an individual at high risk for developing cancer.

In other embodiments of the invention, there is a kit for cancer treatment, said kit housed in a suitable container and comprising: a first anti-cancer agent that inhibits TFIIS expression and/or activity; and a second anti-cancer agent. In a specific embodiment, the first agent comprises siRNA, such as SEQ ID NO:7, SEQ ID NO:10, or a mixture thereof, for example. In additional embodiments, the second agent comprises one or more chemotherapeutic agents, such as one or more chemotherapeutic agents effective against breast cancer, lung cancer, prostate cancer, or pancreatic cancer, for example. Chemotherapeutic agent effective against breast cancer comprises paclitaxel, Tamoxifen, trastuzumab, or a combination thereof, for example. Chemotherapeutic agent effective against lung cancer comprises gefitinib, erlotinib, cisplatin, carboplatin, gemcitabine, paclitaxel, docetaxel, etoposide, vinorelbine, cyclophosphamide, doxorubicin, vincristine, topotecan, or a combination thereof, for example. Chemotherapeutic agent effective against prostate cancer comprises mitoxantrone, prednisone, paclitaxel, docetaxel, estramustine, adriamycin, or a combination thereof, for example. Chemotherapeutic agent effective against pancreatic cancer comprises gemcitabine, 5-fluorouracil, cisplatin, irinotecan, paclitaxel, capecitabine, oxaliplatin, streptozocin, or a combination thereof, for example. In a specific embodiment, the second agent comprises one or more radioisotopes.

In an additional embodiment, there is a method of screening for an agent that inhibits TFIIS or GDOWN1, comprising the steps of: (a) providing a candidate modulator; (b) admixing the candidate modulator with a respective TFIIS or GDOWN1 polynucleotide or polypeptide; and (c) assaying association of the candidate modulator with the respective polynucleotide or polypeptide, wherein when the candidate modulator associates with the respective polynucleotide or polypeptide, said candidate modulator is the agent. In a specific embodiment, the association is further defined as binding. In additional embodiments, the method further comprises manufacturing the agent. In specific embodiments, the method further comprises delivering the agent to an individual that has cancer or that is suspected of having cancer or that is at high risk for developing cancer.

In an additional embodiment of the invention, there is a method of treating an individual with cancer, comprising delivering to the individual an effective amount of a composition comprising an agent that inhibits TFIIS or GDOWN1.

In an embodiment of the invention, there is a method of inhibiting proliferation of at least one cancer cell, comprising delivering to the cell an effective amount of a composition comprising one or both of the following: an agent that inhibits TFIIS; and an agent that inhibits GDOWN1. In a specific embodiment, one or both of the agents are further defined as being an agent that inhibits proliferation of the cancer cell but does not inhibit proliferation of a non-cancerous cell, such as a non-cancerous cell from the same tissue, for example. In further specific embodiments, the agent comprises nucleic acid, such as DNA, RNA, or a mixture thereof. RNA molecules include antisense RNA or siRNA. In particular embodiments, the siRNA can be one or more sequences selected from the group consisting of SEQ ID NO:7, SEQ ID NO:10, or a mixture thereof.

An agent that inhibits TFIIS, GDOWN1, or both may inhibit its expression, may inhibit its activity, may increase its rate of degradation, or a combination thereof. In specific embodiments, the agent acts directly on TFIIS or GDOWN1, respectively, or the agent may act indirectly through affecting at least one other molecule.

In particular embodiments, the cell for which proliferation is inhibited may be any cell, although in specific embodiments the cell is a cancer cell. Although the cancer cell may be any kind of cancer cell, in specific embodiments it is a breast cancer cell, a prostate cancer cell, a lung cancer cell, or a pancreatic cancer cell. The proliferation may be inhibited completely, or the proliferation may be reduced at least in part.

In another embodiment of the invention, there is a method for identifying an agent that inhibits TFIIS. In particular, the method may comprise providing a candidate inhibitor; and admixing the candidate inhibitor with TFIIS, wherein when said candidate inhibitor inhibits the activity of TFIIS, said candidate inhibitor is an agent that inhibits TFIIS. In specific embodiments, the agent is manufactured. In additional specific embodiments, an effective amount of the agent is administered to an individual, such as an individual that has cancer, that is suspected of having cancer, or that is at risk for developing cancer.

In an additional embodiment of the invention, there is a method of manufacturing a TFIIS inhibitor comprising: (a) providing a candidate substance suspected of decreasing TFIIS expression or activity; (b) selecting the TFIIS inhibitor by assessing the ability of the candidate substance to decrease TFIIS expression or activity; and (c) manufacturing the selected TFIIS inhibitor. In a specific embodiment, the candidate substance is a small molecule, a protein, or a nucleic acid molecule. The providing step may be further defined as providing in a cell or a cell-free system a TFIIS polypeptide and the TFIIS polypeptide is contacted with the candidate substance. When the candidate substance is a protein, it may be an antibody that binds immunologically to TFIIS, for example. The providing step may be further defined as providing a nucleic acid molecule that encodes the TFIIS polypeptide. The nucleic acid molecule may be an antisense molecule. The nucleic acid may be an siRNA molecule. The siRNA molecule may comprise SEQ ID NO. 7, SEQ ID NO:10, or a mixture thereof.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

In FIG. 3A, pure calf thymus RNAP is purified employing a previously published protocol with some modifications (Thompson et al., 1990); subunits one through three of the twelve-subunit enzyme are indicated. In FIG. 3B, purified 6Xhistidine-tagged TFIIS appears as a single protein band.

FIG. 4 provides exemplary templates and sequences for transcription. Templates employed in assays below are listed as two oligonucleotide homologous pairs with a 3' single stranded region in the template strand. An early arrest site that exists in tailed templates is shown in bold, and poly T sequences, which are thought to enhance arresting of transcription, are underlined.

In FIG. 5A, tailed DNA templates comprise a single stranded 3' region where initiation occurs. The template strand is depicted fixed to a plate. The non-template strand has a green star, if demonstrated in a color representation, which represents a fluorescent label. In FIG. 8B, RNAP is depicted transcribing a short red RNA strand. The enzyme is unable to readthrough the early arrest site without TFIIS. The nontemplate strand remains hybridized to the template strand. FIG. 8C shows that in the presence of TFIIS the nontemplate strand is displaced into the supernatant by RNA, and fluorescence of the nontemplate strand in the supernatant is an indication of readthrough.

In FIG. 9A, 96-well plates are depicted with a robotic arm that can dispense reagents. Five to ten µl of the small molecule library stock is added to a 96 well plate containing the assay mix depicted in the plate in 9B. In FIG. 9B, the assay plate is green in a color representation, since the nontemplate strand is fluorescent. TFIIS and RNAP are then added to begin the assay as depicted in FIG. 9C. In FIG. 9C, after completion of the assay the reaction mix is transferred to the plate in FIG. 9D, and fluorescence is determined by a fluorescent plate reader as depicted in FIG. 9E. Note that white wells in 9D represent a lack of TFIIS function. Since TFIIS in these wells is inhibited, the nontemplate strand in those wells will not be displaced, and no fluorescence will be detected.

FIGS. 10A-10D show that two forms of RNAPII differ in subunit content. In FIG. 10A, FI and FII RNAPII separated by UNO Q-1 HPLC are resolved on a 4-20% SDS PAGE (NuPAGE). Rpb1-3 represent RNAPII subunits 1-3. An additional stoichiometric 41 kD polypeptide is present in FI. M represents protein marker sizes of 185, 98, 52, 31, 19/17, 11, 6 and 3 kD. In FIG. 10B, both RNAPII FI and FII were assayed using a tailed template. Both early-arrest and readthrough transcripts are indicated. In FIG. 10C, 10 µg of a mixture of FI and FII purified RNAPII was subjected to 6% SDS PAGE. Lanes 1 and 4: untreated RNAPII with major amounts of IIA and minor amounts of IIO, lanes 2 and 3: RNAPII after phosphorylation with 5 or 10 µg of human p42 MAPK2 respectively. Lane 5: RNAPII after dephosphorylation. Lane 6: 193 kD myosin marker. In FIG. 10D, there is western blot analysis of FI and FII with various antibodies as indicated in materials and methods.

FIGS. 11A-11B show peptide A and B from Edman degradation compared with Gdown1. In FIG. 11A, peptide sequences A and B determined by Edman degradation are aligned with GRINL1A CTU polypeptide sequences sharing common domains. Sequences were predicted from human cDNAs with GenBank® accession numbers as follows: Gdown1 AF326773; Gdown2 AK074767 translated from frame3; Gdown6 AY353061 translated from frame 1; and Gcom1 AY207007. In FIG. 11B, Gdown1 sequences from various species were aligned. Protein sequences were from the PIR database as follows; Q96JB7-human; Q5REC6-orangutan; Q6P6I6-mouse; Q91XQ4-rat; Q9CXJ7-mouse; and Q5U282-frog. The bovine sequence was deduced from partial cDNA sequences from PIR BF042463 and TIGR sequences TC281745 and TC266399.

FIG. 15 shows sequences of human Gdown1 and other predicted polypeptides from the GRINL1A CTU-Shared domains were aligned employing GeneBee (64). Protein sequences were predicted from human cDNA sequences with accession numbers as follows: Gdown1 AF326773 (SEQ ID NO:34) (polypeptide is SEQ ID NO:35), Gdown2 AK074767 (SEQ ID NO:36) translated from frame3 (polypeptide is SEQ ID NO:37), Gdown6 AY353061 (SEQ ID NO:38) translated from frame 1 (polypeptide is SEQ ID NO:39), and Gcom1 AY207007 (SEQ ID NO:40) (polypeptide is SEQ ID NO:41). Sequences determined by Edman degradation are listed as PeptideA or PeptideB. Amino acids in shaded blocks represent non-identical sequences.

FIG. 16 illustrates protein sequence alignment of Gdown1, now identified as RNAPII subunit 13, Rpb13-Rpb13 protein sequences from various species were aligned employing GeneBee (64). Protein sequences were from the PIR database as follows; Q96JB7-human (SEQ ID NO:42), Q5REC6-orangutan (SEQ ID NO:43), Q6P6I6-mouse (SEQ ID NO:44), Q91XQ4-rat (SEQ ID NO:45), Q9CXJ7-mouse (SEQ ID NO:46), and Q5U282-frog (SEQ ID NO:47) and PeptideA (SEQ ID NO:52) or B (SEQ ID NO:53) for peptide sequences determined by Edman degradation. The predicted bovine sequence (SEQ ID NO:51) was deduced from partial cDNA sequences from PIR BF042463 (SEQ ID NO:48) and TIGR sequences TC281745 (SEQ ID NO:49) and TC266399 (SEQ ID NO:50). Shaded boxes represent amino acid differences between sequences. Underlined sequences are sequence tag homologies identified by mass spectrometry. Peptide sequences are listed as peptide A or peptide B.

FIG. 17 demonstrates relative expression of Gdown1 compared to β-actin in siRNA treated MCF7 cells—SiRNA treated MCF7 cells are shown to contain only 53% (+/−6.2) Gdown1 mRNA. with β-actin as control. The control consisted of transfection agent without siRNA. Two separate experiments were performed with n=3 and the cycle threshold was determined. The PCR efficiency for β-Actin and TFIIS was 2.042 and 2.171 respectively.

DETAILED DESCRIPTION OF THE INVENTION

I. Definitions

Figure 1:
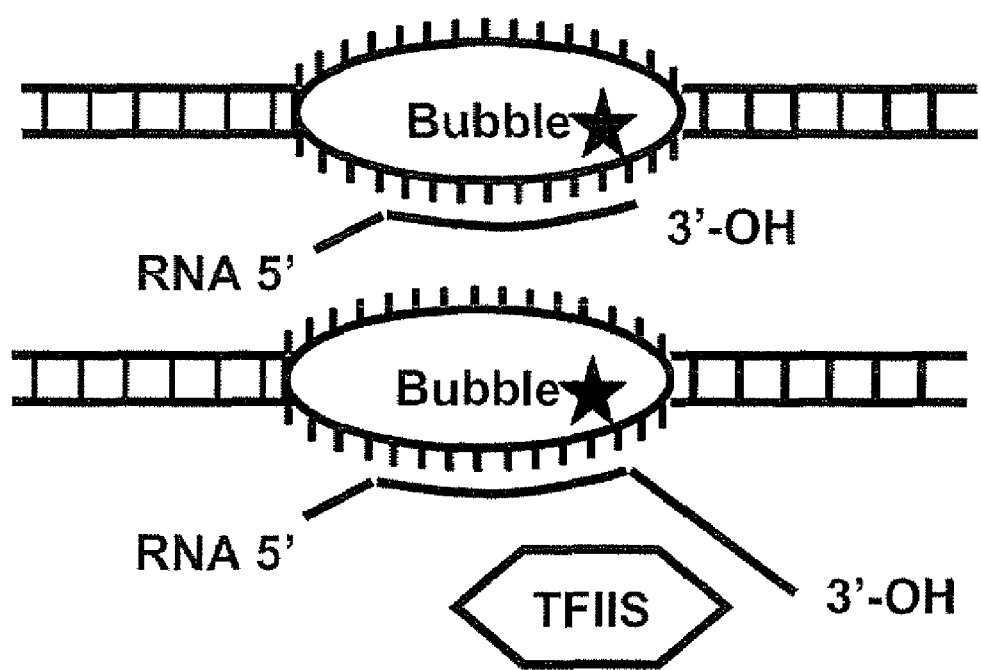
FIG. 1 demonstrates a mechanism of TFIIS function. Double stranded DNA is depicted as "railroad tracks", the unwound DNA shown as a "bubble," and the active site RNAP magnesium is depicted as a star. In the top image, the 3'-hydroxyl of the RNA is adjacent to the active site, whereas in the arrested elongation complex on the bottom image the 3'-hydroxyl is no longer aligned with the active site magnesium. TFIIS interacts with RNAP and allows it to cut about 7-9 bases of the protruding RNA. Transcription then resumes.

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

II. The Present Invention

Transcription is the process entailing the "reading" of the genome and results in the generation of mRNA. One of the underlying mechanisms of cancers, including breast, lung, pancreatic, and prostate cancers, is improper control of transcription. This includes modulated levels of gene expression, such as for c-myc, in at least prostate and breast cancers as well as numerous other genes, which are upregulated or downregulated. TFIIS, which directly interacts with the transcription "motor", RNA Polymerase II (RNAP), is a transcription elongation factor that allows for the effective production of the myc oncogene among others. In additional embodiments, the present invention concerns a thirteenth subunit of RNAP named GDOWN1 that upon decrease in expression and/or activity facilitates death of a cancer cell. In some aspects of the following description, TFIIS is employed as an exemplary embodiment, although the disclosure similarly applies to GDOWN1 alone or in conjunction with TFIIS.

Methods of the present invention particularly concern inhibiting proliferation of deleterious cells, such as cancer cells, although in alternative cases the proliferation of other types of cells is inhibited, such as cells involved in restenosis, for example. The proliferation of the cell is inhibited at least in part by the inhibition of the expression and/or activity and/or by increasing the degradation or rate of degradation of TFIIS, GDOWN1, or both. The inhibition of these targets may be by any means, including by targeting polynucleotides that encode TFIIS, for example, by targeting polypeptides encoded thereby, or by targeting both.

In particular cases, one or more specific agents are employed to inhibit TFIIS. The agent may be of any suitable kind so long as it is effective in inhibiting TFIIS at least partially. The agent may include a polynucleotide, which may be referred to as nucleic acid; a polypeptide, which may be a protein, in some cases; a peptide; a small molecule; or a mixture thereof. The agent may be a natural agent, a synthetic agent, or a mixture thereof. The present invention encompasses methods of identifying such an agent, including by assaying libraries of small molecules, by assaying inhibitory nucleic acids, or both, for example. Any assay to identify one or more agents is suitable for the invention so long as a TFIIS inhibitory agent is identifiable.

In specific embodiments, the agent that inhibits TFIIS includes nucleic acid, such as DNA, RNA, or a mixture thereof. The RNA may be of any kind, such as RNA suitable for RNA interference. In particular cases, siRNA is employed as the inhibitory agent, and the skilled artisan may employ the exemplary siRNA molecules provided herein or may similarly generate other suitable siRNAs to inhibited TFIIS.

III. TFIIS

RNA Polymerase II (RNAP) comprises the transcription motor in eukaryotic cells. It comprises at least 12 subunits and may comprise at least 13 subunits. RNAP has numerous polypeptides that assist it in reading through DNA unhindered. One such example is transcription factor S-II (also referred to as TFIIS and Transcription Elongation Factor A (TCEA)). In particular, TFIIS is important for efficient RNA polymerase II transcription elongation past template-encoded arresting sites. A certain fraction of elongating RNA polymerases are trapped at arresting sites in DNA resulting in locked ternary complexes. TFIIS cleaves the nascent transcript, thereby allowing elongation to resume from the new 3'terminus.

Three different isoforms of TFIIS exist and are referred to as TCEA1, TCEA2, and TCEA3. In particular aspects of the invention, one or more of the isoforms is targeted by the methods and compositions of the present invention.

IV. RNAi and siRNA Embodiments

RNA interference (also referred to as "RNA-mediated interference"; RNAi) is a mechanism by which gene expression can be reduced or eliminated. Double stranded RNA (dsRNA) or single stranded RNA has been observed to mediate the reduction, which is a multi-step process (for details of single stranded RNA methods and compositions see Martinez et al., 2002, for example). dsRNA activates post-transcriptional gene expression surveillance mechanisms that appear to function to defend cells from virus infection and transposon activity (Fire et al., 1998; Grishok et al., 2000; Ketting et al., 1999; Lin et al, 1999; Montgomery et al., 1998; Sharp et al., 2000; Tabara et al., 1999). Activation of these mechanisms targets mature, dsRNA-complementary mRNA for destruction. RNAi offers major experimental advantages for study of gene function. These advantages include a very high specificity, ease of movement across cell membranes, and prolonged down-regulation of the targeted gene. (Fire et al., 1998; Grishok et al., 2000; Ketting et al, 1999; Lin et al., 1999; Montgomery et al., 1998; Sharp, 1999; Sharp et al., 2000; Tabara et al., 1999). Moreover, dsRNA has been shown to silence genes in a wide range of systems, including plants, protozoans, fungi, *C. elegans, Trypanasoma, Drosophila*, and mammals (Grishok et al., 2000; Sharp, 1999; Sharp et al, 2000; Elbashir et al., 2001).

SiRNAs are small RNAs that do not significantly induce the antiviral response common among vertebrate cells but that do induce target mRNA degradation via the RNAi pathway. The term siRNA refers to RNA molecules that have either at least one double stranded region or at least one single stranded region and possess the ability to effect RNAi. It is specifically contemplated that siRNA may refer to RNA molecules that have at least one double stranded region and possess the ability to effect RNAi. Mixtures or pools of dsRNAs (siRNAs) may be generated by various methods including chemical synthesis, enzymatic synthesis of multiple templates, digestion of long dsRNAs by a nuclease with RNAse III domains, and the like. A "pool" or "cocktail" refers to a composition that contains at least two siRNA molecules that have different selectivity with respect to each other, but are directed to the same target gene. Two or more siRNA molecules that have different selectivity with respect to each other, but are directed to the same or different target gene(s) are defined as different siRNAs. Different siRNAs may overlap in sequence, contain two sequences that are contiguous or non-contiguous in the target gene. In some embodiments, a pool contains at least or at most 3, 4, 5, 6, 7, 8, 9, 10 or more siRNA molecules. An "siRNA directed to" a particular region or target gene means that a particular siRNA includes sequences that results in the reduction or elimination of expression of the target gene, i.e., the siRNA is targeted to the region or gene. The pool in some embodiments includes one or more control siRNA molecules. In other embodiments a control siRNA molecule is not included in the pool. A pool of siRNA molecules may also contain various candidate siRNA molecules that do not reduce or eliminate expression of a target gene.

Some of the uses for RNAi include implementing therapeutics and diagnostics, identifying genes that are essential for a particular biological pathway, identifying disease-causing genes, and studying structure function relationships. As with other types of gene inhibitory compounds, such as antisense and triplex forming oligonucleotides, tracking these potential drugs in vivo and in vitro is important for drug development, pharmacokinetics, biodistribution, macro and microimaging metabolism and for gaining a basic understanding of how these compounds behave and function. siRNAs have high specificity and may be used to knock out the expression of a single allele of a dominantly mutated diseased gene.

In certain embodiments of the invention, TFIIS is targeted with one or more siRNA molecules. Thus, in specific embodiments a cancer cell or a cell suspected of being or becoming cancerous is provided with one or more siRNAs directed against TFIIS. In particular embodiments, an individual with cancer, suspected of having cancer, at a high risk for cancer, or susceptible to cancer is administered one or more siRNA molecules directed against TFIIS.

The present invention includes methods and compositions for introducing multiple siRNAs targeting different regions of a gene that typically can greatly improve the likelihood that the expression of the target gene will be reduced. The inventors have found that the different candidate siRNAs or siRNAs do not interfere with the activities of others in the mixture and that in fact, there appears to be some synergy between the siRNAs. This is applicable not only to siRNAs but to DNA constructs designed to express siRNAs (Brummelkamp, 2002). Certain embodiments of the invention alleviate the need to screen or optimize candidate siRNAs. To determine the functionality of a candidate siRNA, it must be screened, verified, and/or optimized. As used herein, a "candidate siRNA" is an siRNA that has not been tested for its functionality as an siRNA. It is also contemplated that siRNAs may be single or double stranded RNA molecules.

In some embodiments of the invention, methods are employed wherein multiple therapeutic RNAs are employed, each of which reduce the expression of a target gene to some degree, as well as the presence of some dsRNAs, which do not effect target gene expression, may be administered as a pool without interference between members of the pool and may result in an additive or synergistic reduction in target gene expression. Thus, the present invention is directed to compositions and methods involving generation and utilization of pools or mixtures of small, double-stranded RNA molecules that effect, trigger, or induce RNAi more effectively. RNAi is mediated by an RNA-induced silencing complex (RISC), which associates (specifically binds one or more RISC components) with dsRNA pools of the invention and guides the dsRNA to its target mRNA through base-pairing interactions. Once the dsRNA is base-paired with its mRNA target, nucleases cleave the mRNA.

In certain embodiments of the invention, one or more siRNAs or dsRNAs can be introduced into a cell to activate the RNAi pathway. In other embodiments, various individual siRNAs or dsRNAs with different sequences may be co-transfected simultaneously to effectively produce a pool or mixture of dsRNAs within a transfected cell(s). The effects of multiple siRNAs are typically additive and may be synergistic in some cases.

In some embodiments, the invention concerns a siRNA or dsRNA that is capable of triggering RNA interference, a process by which a particular RNA sequence is destroyed (also referred to as gene silencing). siRNA are dsRNA molecules that are 100 bases or fewer in length (or have 100 basepairs or fewer in its complementarity region). A dsRNA may be 15, 16, 17, 18, 19, 20, 21, 22, 23, 24, 25, 26, 27, 28, 29, 30, 40, 50, 60, 70, 80, 90, 100 110, 120, 130, 140, 150, 160, 170, 180, 190, 200, 225, 250, 275, 300, 325, 350. 375, 400, 450, 500, 550, 600, 650, 700, 750, 800, 850, 900, 950, or 1000 nucleotides or more in length. In certain embodiments, siRNA may be approximately 21 to 25 nucleotides in length. In some cases, it has about a two nucleotide 3' overhang and a 5' phosphate. The particular RNA sequence is targeted as a result of the complementarity between the dsRNA and the particular RNA sequence. It will be understood that siRNA or dsRNA of the invention can effect at least about a 20, 30, 40, 50, 60, 70, 80, 90 percent or more reduction of expression of a targeted RNA in a cell. dsRNA of the invention (the term "dsRNA" will be understood to include "siRNA" and/or "candidate siRNA") is distinct and distinguishable from antisense and ribozyme molecules by virtue of the ability to trigger RNAi. Structurally, dsRNA molecules for RNAi comprise at least one region of complementarity within the RNA molecule. The complementary (also referred to as "complementarity") region comprises at least or at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 contiguous bases. In some embodiments, long dsRNA are employed in which "long" refers to dsRNA that are 1000 bases or longer (or 1000 basepairs or longer in complementarity region). The term "dsRNA" includes "long dsRNA", "intermediate dsRNA" or "small dsRNA" (lengths of 2 to 100 bases or basepairs in complementarity region) unless otherwise indicated.

It is specifically contemplated that a dsRNA may be a molecule comprising two separate RNA strands in which one strand has at least one region complementary to a region on the other strand. Alternatively, a dsRNA includes a molecule that is single stranded yet has at least one complementarity region as described above (see Sui et al., 2002 and Brummelkamp et al., 2002 in which a single strand with a hairpin loop is used as a dsRNA for RNAi). For convenience, lengths of dsRNA may be referred to in terms of bases, which simply refers to the length of a single strand or in terms of basepairs, which refers to the length of the complementarity region. It is specifically contemplated that embodiments discussed herein with respect to a dsRNA comprised of two strands are contemplated for use with respect to a dsRNA comprising a single strand, and vice versa. In a two-stranded dsRNA molecule, the strand that has a sequence that is complementary to the targeted mRNA is referred to as the "antisense strand" and the strand with a sequence identical to the targeted mRNA is referred to as the "sense strand." Similarly, with a dsRNA comprising only a single strand, it is contemplated that the "antisense region" has the sequence complementary to the targeted mRNA, while the "sense region" has the sequence identical to the targeted mRNA. Furthermore, it will be understood that sense and antisense region, like sense and antisense strands, are complementary (i.e., can specifically hybridize) to each other.

Strands or regions that are complementary may or may not be 100% complementary ("completely or fully complementary"). It is contemplated that sequences that are "complementary" include sequences that are at least about 50% complementary, and may be at least about 50%, 60%, 70%, 80%, or 90% complementary. In the range of about 50% to 70% complementarity, such sequences may be referred to as "very complementary," while the range of greater than about 70% to less than complete complementarity can be referred to as "highly complementary." Unless otherwise specified, sequences that are "complementary" include sequences that are "very complementary," "highly complementary," and "fully complementary." It is also contemplated that any embodiment discussed herein with respect to "complementary" strands or region can be employed with specifically "fully complementary," "highly complementary," and/or "very complementary" strands or regions, and vice versa. Thus, it is contemplated that in some instances, as demonstrated in the Examples, that siRNA generated from sequence based on one organism may be used in a different organism to achieve RNAi of the cognate target gene. In other words, siRNA generated from a dsRNA that corresponds to a human gene may be used in a mouse cell if there is the requisite complementarity, as described above. Ultimately, the requisite threshold level of complementarity to achieve RNAi is dictated by functional capability.

It is specifically contemplated that there may be mismatches in the complementary strands or regions. Mismatches may number at most or at least 1, 2, 3, 4, 5, 6, 7, 8, 9, 10, 11, 12, 13, 14, 15, 16, 17, 18, 19, 20, 21, 22, 23, 24, 25 residues or more, depending on the length of the complementarity region.

The single RNA strand or each of two complementary double strands of a dsRNA molecule may be of at least or at most the following lengths: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 31, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 or more (including the full-length of a particular's gene's mRNA without the poly-A tail) bases or basepairs. If the dsRNA is comprised of two separate strands, the two strands may be the same length or different lengths. If the dsRNA is a single strand, in addition to the complementarity region, the strand may have 1, 2, 3, 4, 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more bases on either or both ends (5' and/or 3') or as forming a hairpin loop between the complementarity regions.

Furthermore, it is contemplated that siRNA or the longer dsRNA template may be labeled. The label may be fluorescent, radioactive, enzymatic, or calorimetric, for example. It is contemplated that a dsRNA may have one label attached to it or it may have more than one label attached to it. When more than one label is attached to a dsRNA, the labels may be the same or be different. If the labels are different, they may appear as different colors when visualized. The label may be on at least one end and/or it may be internal. Furthermore, there may be a label on each end of a single stranded molecule or on each end of a dsRNA made of two separate strands. The end may be the 3' and/or the 5' end of the nucleic acid. A label may be on the sense strand or the sense end of a single strand (end that is closer to sense region as opposed to antisense region), or it may be on the antisense strand or antisense end of a single strand (end that is closer to antisense region as opposed to sense region). In some cases, a strand is labeled on a particular nucleotide (G, A, U, or C). When two or more differentially colored labels are employed, fluorescent resonance energy transfer (FRET) techniques may be employed to characterize the dsRNA.

Labels contemplated for use in several embodiments may be non-radioactive. In many embodiments of the invention, the labels are fluorescent, though they may be enzymatic, radioactive, or positron emitters. Fluorescent labels that may be used include, but are not limited to, BODIPY, Alexa Fluor, fluorescein, Oregon Green, tetramethylrhodamine, Texas Red, rhodamine, cyanine dye, or derivatives thereof, for example. The labels may also more specifically be Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, DAPI, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, TET, Tetramethylrhodamine, and/or Texas Red, for example. A labeling reagent is a composition that comprises a label and that can be incubated with the nucleic acid to effect labeling of the nucleic acid under appropriate conditions. In some embodiments, the labeling reagent comprises an alkylating agent and a dye, such as a fluorescent dye. In some embodiments, a labeling reagent comprises an alkylating agent and a fluorescent dye such as Cy3, Cy5, or fluorescein (FAM). In still further embodiments, the labeling reagent is also incubated with a labeling buffer, which may be any buffer compatible with physiological function (i.e., buffers that is not toxic or harmful to a cell or cell component) (termed "physiological buffer").

In some embodiments of the invention, a dsRNA has one or more non-natural nucleotides, such as a modified residue or a derivative or analog of a natural nucleotide. Any modified residue, derivative or analog may be used to the extent that it does not eliminate or substantially reduce (by at least 50%) RNAi activity of the dsRNA.

A person of ordinary skill in the art is well aware of achieving hybridization of complementary regions or molecules. Such methods typically involve heat and slow cooling of temperature during incubation.

Any cell that undergoes RNAi can be employed in methods of the invention. The cell may be a eukaryotic cell, mammalian cell such as a primate, rodent, rabbit, canine, feline, equine, or human cell, for example.

In some embodiments of the invention, there are methods of reducing the expression of a target gene in a cell. Such methods involve the compositions described above, including the embodiments described for RNase III, dsRNA, and siRNA. In various embodiments of the invention, reduction or elimination of expression of one or more target genes may be accomplished by the a) obtaining one or more siRNA or dsRNA molecules corresponding one or more target genes and b) transfecting the respective siRNA or dsRNA molecules corresponding to the one or more target genes into a cell.

In some methods of the invention, siRNA and/or candidate siRNA molecules or template nucleic acids may be isolated or purified prior to their being used in a subsequent step. siRNA and/or candidate siRNA molecules may be isolated or purified prior to introduction into a cell. "Introduction" into a cell includes known methods of transfection, transduction, infection and other methods for introducing an expression vector or a heterologous nucleic acid into a cell. A template nucleic acid or amplification primer may be isolated or purified prior to it being transcribed or amplified. Isolation or purification can be performed by a number of methods known to those of skill in the art with respect to nucleic acids. In some embodiments, a gel, such as an agarose or acrylamide gel, is employed to isolate the siRNA and/or candidate siRNA.

In some methods of the invention dsRNA is obtained by transcribing each strand of the dsRNA from one or more cDNA (or DNA or RNA) encoding the strands in vitro. It is contemplated that a single template nucleic acid molecule may be used to transcribe a single RNA strand that has at least one region of complementarity (and is thus double-stranded under conditions of hybridization) or it may be used to transcribe two separate complementary RNA molecules. Alternatively, more than one template nucleic acid molecule may be transcribed to generate two separate RNA strands that are complementary to one another and capable of forming a dsRNA.

Additional methods involve isolating the transcribed strand(s) and/or incubating the strand(s) under conditions that allow the strand(s) to hybridize to their complementary strands (or regions if a single strand is employed).

Nucleic acid templates may be generated by a number of methods well known to those of skill in the art. In some embodiments the template, such as a cDNA, is synthesized through amplification or it may be a nucleic acid segment in or from a plasmid that harbors the template.

In various embodiments, siRNAs are encoded by expression constructs. The expression constructs may be obtained and introduced into a cell. Once introduced into the cell the expression construct is transcribed to produce various siR- NAs. Expression constructs include nucleic acids that provide for the transcription of a particular nucleic acid. Expression constructs include plasmid DNA, linear expression elements, circular expression elements, viral expression constructs, and the like, all of which are contemplated as being used in the compositions and methods of the present invention. In certain embodiments at least about 2, 3, 4, 5, 6, 7, 8, 9, 10 or more siRNA molecules are encoded by a single expression construct. Expression of the siRNA molecules may be independently controlled by at least about 2, 3, 4, 5, 6, 7, 8, 9, 10 or more promoter elements. In certain embodiments, at least about 2, 3, 4, 5, 6, 7, 8, 9, 10 or more expression constructs may introduced into the cell. Each expression construct may encode 1, 2, 3, 4, 5, 6, 7, 8, 9, 10 or more siRNA molecules. In certain embodiments siRNA molecules may be encoded as expression domains. Expression domains include a transcription control element, which may or may not be independent of other control or promoter elements; a nucleic acid encoding an siRNA; and optionally a transcriptional termination element. In other words, an siRNA cocktail or pool may be encoded by a single or multiple expression constructs. In particular embodiments the expression construct is a plasmid expression construct.

Other methods of the invention also concern transcribing a strand or strands of a dsRNA using a promoter that can be employed in vitro or outside a cell, such as a prokaryotic promoter. In some embodiments, the prokaryotic promoter is a bacterial promoter or a bacteriophage promoter. It is specifically contemplated that dsRNA strands are transcribed with SP6, T3, or T7 polymerase.

V. Nucleic Acids of the Invention

Certain embodiments of the present invention concern nucleic acids, including TFIIS or GDOWN1 nucleic acids and siRNAs that inhibit TFIIS nucleic acids and GDOWN1 nucleic acids, respectively. The following description will employ TFIIS as an exemplary embodiment, although the disclosure similarly applies to GDOWN1. In certain aspects, a TFIIS nucleic acid comprises a wild-type or a mutant TFIIS nucleic acid. An exemplary TFIIS nucleic acid sequence is comprised in SEQ ID NO:15 (GenBank® Accession Number M81601.1; GI:339442 from the world wide web internet site of the National Center for Biotechnology Information) and is provided for any application, including to facilitate identifying a suitable siRNA sequence for the invention, for example. In particular aspects, a TFIIS nucleic acid encodes for or comprises a transcribed nucleic acid, although in other cases the nucleic acid comprises a fragment of a TFIIS nucleic acid that encodes a polypeptide or comprises a siRNA sequence. In other aspects, a TFIIS nucleic acid comprises a nucleic acid segment of SEQ ID NO:15, or a biologically functional equivalent thereof. In particular aspects, a TFIIS nucleic acid encodes a protein, polypeptide, peptide, although in embodiments such as with siRNA the molecule may be too short to effectively encode a gene product. An exemplary GDOWN1 nucleic acid sequence is comprised in SEQ ID NO:27 (Accession number AF326773 of GenBank®), which may encode SEQ ID NO:28 (Accession number AAK92284 of GenBank®).

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C).

The term "nucleic acid" encompass the terms "oligonucleotide" and "polynucleotide," each as a subgenus of the term "nucleic acid." In some embodiments, the term "oligonucleotide" refers to a molecule of between about 3 and about 100 nucleobases in length. In some embodiments, the term "polynucleotide" refers to at least one molecule of greater than about 100 nucleobases in length.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss," a double stranded nucleic acid by the prefix "ds," and a triple stranded nucleic acid by the prefix "ts."

A. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moeity. Preferred alkyl (e.g., alkyl, caboxyalkyl, etc.) moeities comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. A nucleobase may be comprised in a nucleoside or nucleotide, using any chemical or natural synthesis method described herein or known to one of ordinary skill in the art.

B. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

C. Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

D. Nucleic Acid Analogs

A nucleic acid may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in U.S. Pat. No. 5,681,947 which describes oligonucleotides comprising purine derivatives that form triple helixes with and/or prevent expression of dsDNA; U.S. Pat. Nos. 5,652,099 and 5,763,167 which describe nucleic acids incorporating fluorescent analogs of nucleosides found in DNA or RNA, particularly for use as flourescent nucleic acids probes; U.S. Pat. No. 5,614,617 which describes oligonucleotide analogs with substitutions on pyrimidine rings that possess enhanced nuclease stability; U.S. Pat. Nos. 5,670,663, 5,872,232 and 5,859,221 which describe oligonucleotide analogs with modified 5-carbon sugars (i.e., modified 2'-deoxyfuranosyl moieties) used in nucleic acid detection; U.S. Pat. No. 5,446, 137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' internucleotide linkages and ribonucleotides with 2'-5' internucleotide linkages; U.S. Pat. No. 5,714,606 which describes a modified internucleotide linkage wherein a 3'-position oxygen of the internucleotide linkage is replaced by a carbon to enhance the nuclease resistance of nucleic acids; U.S. Pat. No. 5,672,697 which describes oligonucleotides containing one or more 5' methylene phosphonate internucleotide linkages that enhance nuclease resistance; U.S. Pat. Nos. 5,466, 786 and 5,792,847 which describe the linkage of a substituent moiety which may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967 which describes oligonucleotides comprising at least one sulfamate or sulfamide internucleotide linkage that are useful as nucleic acid hybridization probe; U.S. Pat. Nos. 5,378,825, 5,777,092, 5,623, 070, 5,610,289 and 5,602,240 which describe oligonucleotides with three or four atom linker moeity replacing phosphodiester backbone moeity used for improved nuclease resistance, cellular uptake and regulating RNA expression; U.S. Pat. No. 5,858,988 which describes hydrophobic carrier agent attached to the 2'-O position of oligonucleotides to enhanced their membrane permeability and stability; U.S. Pat. No. 5,214,136 which describes oligonucleotides conjugaged to anthraquinone at the 5' terminus that possess enhanced hybridization to DNA or RNA; enhanced stability to nucleases; U.S. Pat. No. 5,700,922 which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154 which describes RNA linked to a DNA to form a DNA-RNA hybrid.

E. Polyether and Peptide Nucleic Acids

In certain embodiments, it is contemplated that a nucleic acid comprising a derivative or analog of a nucleoside or nucleotide may be used in the methods and compositions of the invention. A non-limiting example is a "polyether nucleic acid", described in U.S. Pat. No. 5,908,845, incorporated herein by reference. In a polyether nucleic acid, one or more nucleobases are linked to chiral carbon atoms in a polyether backbone.

Another non-limiting example is a "peptide nucleic acid", also known as a "PNA", "peptide-based nucleic acid analog" or "PENAM", described in U.S. Pat. Nos. 5,786,461, 5,891, 625, 5,773,571, 5,766,855, 5,736,336, 5,719,262, 5,714,331, 5,539,082, and WO 92/20702, each of which is incorporated herein by reference. Peptide nucleic acids generally have enhanced sequence specificity, binding properties, and resistance to enzymatic degradation in comparison to molecules such as DNA and RNA (Egholm et al., 1993; PCT/EP/01219). A peptide nucleic acid generally comprises one or more nucleotides or nucleosides that comprise a nucleobase moiety, a nucleobase linker moeity that is not a 5-carbon sugar, and/or a backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

In certain embodiments, a nucleic acid analogue such as a peptide nucleic acid may be used to inhibit nucleic acid amplification, such as in PCR, to reduce false positives and discriminate between single base mutants, as described in U.S. Pat. No. 5,891,625. Other modifications and uses of nucleic acid analogs are known in the art, and are encompassed by the invention. In a non-limiting example, U.S. Pat. No. 5,786,461 describes PNAs with amino acid side chains attached to the PNA backbone to enhance solubility of the molecule. In another example, the cellular uptake property of PNAs is increased by attachment of a lipophilic group. U.S. application Ser. No. 117,363 describes several alkylamino moeities used to enhance cellular uptake of a PNA. Another example is described in U.S. Pat. Nos. 5,766,855, 5,719,262, 5,714,331 and 5,736,336, which describe PNAs comprising naturally and non-naturally occurring nucleobases and alkylamine side chains that provide improvements in sequence specificity, solubility and/or binding affinity relative to a naturally occurring nucleic acid.

F. Preparation of Nucleic Acids

The present invention concerns various nucleic acids in different embodiments of the invention. For example, there are a variety of ways to generate a dsRNA that can function as an siRNA or can be used as a substrate for a polypeptide with RNase III activity to generate siRNAs. In some embodiments, dsRNA is created by transcribing a DNA template. The DNA template may be comprised in a vector or it may be a non-vector template. Alternatively, a dsRNA may be created by hybridizing two synthetic, complementary RNA molecules or hybridizing a single synthetic RNA molecule with at least one intramolecular complementarity region. Such nucleic acids may be made by any technique known to one of ordinary skill in the art, such as for example, chemical synthesis, enzymatic production or biological production.

G. Purification of Nucleic Acids

A nucleic acid may be purified on polyacrylamide gels, cesium chloride centrifugation gradients, or by any other means known to one of ordinary skill in the art (see for example, Sambrook et al., 1989, incorporated herein by reference).

In certain aspect, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

H. Nucleic Acid Segments

In certain embodiments, the nucleic acid is a nucleic acid segment. As used herein, the term "nucleic acid segment," are smaller fragments of a nucleic acid, such as for non-limiting example, those that encode only part of the TFIIS peptide or polypeptide sequence. Thus, a "nucleic acid segment" may comprise any part of a gene sequence, of from about 2 nucleotides to the full length of the TFIIS peptide or polypeptide encoding region.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10 mer, the nucleic acid segments correspond to bases 1 to 10, 2 to 11, 3 to 12 . . . and so on. For a 15-mer, the nucleic acid segments correspond to bases 1 to 15, 2 to 16, 3 to 17 . . . and so on. For a 20-mer, the nucleic segments correspond to bases 1 to 20, 2 to 21, 3 to 22 . . . and so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

I. Nucleic Acid Complements

The present invention also encompasses a nucleic acid that is complementary at least in part to a TFIIS nucleic acid. In particular embodiments the invention encompasses a nucleic acid or a nucleic acid segment complementary to part or all of the sequence set forth in SEQ ID NO:15. A nucleic acid is "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule.

As used herein, the term "complementary" or "complement(s)" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

In certain embodiments, a "partly complementary" nucleic acid comprises a sequence that may hybridize in low stringency conditions to a single or double stranded nucleic acid, or contains a sequence in which less than about 70% of the nucleobase sequence is capable of base-pairing with a single or double stranded nucleic acid molecule during hybridization.

J. Hybridization

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

In certain embodiments, the wild-type sequence of TFIIS may be employed for identification of inhibitors of TFIIS, such as siRNAs. As used herein "wild-type" refers to the naturally occurring sequence of a nucleic acid at a genetic locus in the genome of an organism, or a sequence transcribed or translated from such a nucleic acid. Thus, the term "wild-type" also may refer to an amino acid sequence encoded by a nucleic acid. As a genetic locus may have more than one sequence or alleles in a population of individuals, the term "wild-type" encompasses all such naturally occurring allele(s). As used herein the term "polymorphic" means that variation exists (i.e., two or more alleles exist) at a genetic locus in the individuals of a population. As used herein "mutant" refers to a change in the sequence of a nucleic acid or its encoded protein, polypeptide or peptide that is the result of the hand of man.

The present invention also concerns the isolation or creation of a recombinant construct or a recombinant host cell through the application of recombinant nucleic acid technology known to those of skill in the art or as described herein. A recombinant construct or host cell may comprise a TFIIS nucleic acid or inhibitor thereof, and may express a TFIIS protein, polypeptide or peptide, or at least one biologically functional equivalent thereof, although in alternative embodiments the recombinant construct or host cells comprises a nucleic acid that is too short to encode a protein, polypeptide, or peptide.

Herein certain embodiments, a "gene" refers to a nucleic acid that is transcribed. In certain aspects, the gene includes regulatory sequences involved in transcription, or message production or composition. In particular embodiments, the gene comprises transcribed sequences that encode for a protein, polypeptide or peptide. As will be understood by those in the art, this function term "gene" includes both genomic sequences, RNA or cDNA sequences or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like.

"Isolated substantially away from other coding sequences" means that the gene of interest forms the significant part of the coding region of the nucleic acid, or that the nucleic acid does not contain large portions of naturally-occurring coding nucleic acids, such as large chromosomal fragments, other functional genes, RNA or cDNA coding regions. Of course, this refers to the nucleic acid as originally isolated, and does not exclude genes or coding regions later added to the nucleic acid by the hand of man.

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). As used herein, a "nucleic acid construct" is a nucleic acid engineered or altered by the hand of man, and generally comprises one or more nucleic acid sequences organized by the hand of man.

In a non-limiting example, one or more nucleic acid constructs may be prepared that include a contiguous stretch of nucleotides identical to or complementary to part or all of SEQ ID NO:15. A nucleic acid construct may be about 3, about 5, about 8, about 10 to about 14, or about 15, about 20, about 30, about 40, about 50, about 100, about 200, about 500, about 1,000, about 2,000, about 3,000, about 5,000, about 10,000, about 15,000, about 20,000, about 30,000, about 50,000, about 100,000, about 250,000, about 500,000, about 750,000, to about 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges", as used herein, means any length or range including or between the quoted values (i.e., all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, etc.; about 1,001, about 1002, etc,; about 50,001, about 50,002, etc; about 750,001, about 750,002, etc.; about 1,000,001, about 1,000,002, etc. Non-limiting examples of intermediate ranges include about 3 to about 32, about 150 to about 500,001, about 3,032 to about 7,145, about 5,000 to about 15,000, about 20,007 to about 1,000,003, etc.

In certain embodiments, the nucleic acid construct is a recombinant vector. In particular embodiments, the invention concerns one or more recombinant vector(s) comprising nucleic acid sequences that is capable of encoding an TFIIS protein, polypeptide or peptide that includes within its amino acid sequence a contiguous amino acid sequence in accordance with, or essentially as set forth in, SEQ ID NO:16. In particular aspects, the recombinant vectors are DNA vectors, although in alternative embodiments the vectors comprise RNA vectors.

The term "a sequence essentially as set forth in SEQ ID NO:15" encompasses nucleic acids, nucleic acid segments, and genes that comprise part or all of the nucleic acid sequences as set forth in SEQ ID NO:15.

In certain other embodiments, the invention concerns at least one recombinant vector that includes within its sequence a nucleic acid sequence essentially as set forth in SEQ ID NO:15, or a fragment thereof.

It will also be understood that amino acid sequences or nucleic acid sequences may include additional residues, such as additional N or C terminal amino acids or 5' or 3' sequences, or various combinations thereof, and yet still be essentially as set forth in one of the sequences disclosed herein, so long as the sequence meets the criteria set forth above, including the maintenance of biological protein, polypeptide or peptide activity where expression of a proteinaceous composition is concerned. The addition of terminal sequences particularly applies to nucleic acid sequences that may, for example, include various non-coding sequences flanking either of the 5' and/or 3' portions of the coding region or may include various internal sequences, i.e., introns, which are known to occur within genes.

Excepting intronic and flanking regions, and allowing for the degeneracy of the genetic code, nucleic acid sequences that have between about 70% and about 79%; or more preferably, between about 80% and about 89%; or even more particularly, between about 90% and about 99%; of nucleotides that are identical to the nucleotides of SEQ ID NO:15 will be nucleic acid sequences that are "essentially as set forth in SEQ ID NO:15".

It will also be understood that this invention is not limited to the particular nucleic acid or amino acid sequences of SEQ ID NO:15 or SEQ ID NO:16, respectively. Recombinant vectors and isolated nucleic acid segments may therefore variously include these coding regions themselves, coding regions bearing selected alterations or modifications in the basic coding region, and they may encode larger polypeptides or peptides that nevertheless include such coding regions or may encode biologically functional equivalent proteins, polypeptide or peptides that have variant amino acids sequences.

Changes designed by man may be introduced to the nucleic acids of the invention through the application of site-directed mutagenesis techniques, for example.

VI. Nucleic Acid-Based Expression Systems

In certain aspects of the invention, an agent comprising a nucleic acid that inhibits TFIIS is employed. Such an agent may be comprised within an expression system, such as on a vector, although alternatively the agent is not comprised within an expression system. In other aspects of the invention, the TFIIS or GDOWN1 target sequence to which the agent is directed is utilized within an expression system, such as for agent-identifying or agent-generating purposes, for example.

A. Vectors

Nucleic acids of the invention, particularly DNA templates or DNA constructs for siRNA expression, may be produced recombinantly. Protein and polypeptides may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al, 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

B. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β lactamase (penicillinase), lactose and tryptophan (tip) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, http://www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art. Nonlimiting examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), and human platelet endothelial cell adhesion molecule-1 (Almendro et al., 1996).

C. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

D. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

E. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

F. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

G. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

H. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

I. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

J. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™ 11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with β galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

K. Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Non-limiting examples of virus vectors that may be used to deliver a nucleic acid of the present invention are described below.

1. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

2. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

3. Retroviral Vectors

Retroviruses have promise as delivery vectors due to their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid (e.g., one encoding a polynucleotide of interest) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

4. Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

5. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al, 1989).

L. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel et al., 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); by PEG mediated transformation of protoplasts (Omirulleh et al., 1993; U.S. Pat. Nos. 4,684,611 and 4,952,500, each incorporated herein by reference); by desiccation/inhibition mediated DNA uptake (Potrykus et al., 1985), and any combination of such methods. Through the application of techniques such as these, organelle(s), cell(s), tissue(s) or organism(s) may be stably or transiently transformed.

M. Ex Vivo Transformation

Methods for transfecting vascular cells and tissues removed from an organism in an ex vivo setting are known to those of skill in the art. For example, cannine endothelial cells have been genetically altered by retroviral gene transfer in vitro and transplanted into a canine (Wilson et al., 1989). In another example, yucatan minipig endothelial cells were transfected by retrovirus in vitro and transplanted into an artery using a double-balloon catheter (Nabel et al., 1989). Thus, it is contemplated that cells or tissues may be removed and transfected ex vivo using the nucleic acids of the present invention. In particular aspects, the transplanted cells or tissues may be placed into an organism. In preferred facets, a nucleic acid is expressed in the transplanted cells or tissues.

N. Injection

In certain embodiments, a nucleic acid may be delivered to an organelle, a cell, a tissue or an organism via one or more injections (i.e., a needle injection), such as, for example, subcutaneously, intradermally, intramuscularly, intervenously, intraperitoneally, etc. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into *Xenopus* oocytes (Harland and Weintraub, 1985). The amount of agent used may vary upon the nature of the antigen as well as the organelle, cell, tissue or organism used

O. Electroporation

In certain embodiments of the present invention, a nucleic acid is introduced into an organelle, a cell, a tissue or an organism via electroporation. Electroporation involves the exposure of a suspension of cells and DNA to a high voltage electric discharge. In some variants of this method, certain cell wall degrading enzymes, such as pectin degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre B lymphocytes have been transfected with human kappa immunoglobulin genes (Potter et al., 1984), and rat hepatocytes have been transfected with the chloramphenicol acetyltransferase gene (Tur Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

P. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV 1, BHK, NIH3T3 and HeLa cells were transfected with a neomycin marker gene (Chen and Okayama, 1987), and rat hepatocytes were transfected with a variety of marker genes (Rippe et al., 1990).

Q. DEAE Dextran

In another embodiment, a nucleic acid is delivered into a cell using DEAE dextran followed by polyethylene glycol. In this manner, reporter plasmids were introduced into mouse myeloma and erythroleukemia cells (Gopal, 1985).

R. Sonication Loading

Additional embodiments of the present invention include the introduction of a nucleic acid by direct sonic loading. LTK fibroblasts have been transfected with the thymidine kinase gene by sonication loading (Fechheimer et al., 1987).

S. Liposome Mediated Transfection

In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome mediated nucleic acid delivery and expression of foreign DNA in vitro has been very successful (Nicolau and Sene, 1982; Fraley et al., 1979; Nicolau et al., 1987). The feasibility of liposome mediated delivery and expression of foreign DNA in cultured chick embryo, HeLa and hepatoma cells has also been demonstrated (Wong et al., 1980).

In certain embodiments of the invention, a liposome may be complexed with a hemagglutinatin virus (HVJ). This has been shown to facilitate fusion with the cell membrane and promote cell entry of liposome encapsulated DNA (Kaneda et al., 1989). In other embodiments, a liposome may be complexed or employed in conjunction with nuclear non histone chromosomal proteins (HMG 1) (Kato et al., 1991). In yet further embodiments, a liposome may be complexed or employed in conjunction with both HVJ and HMG 1. In other embodiments, a delivery vehicle may comprise a ligand and a liposome.

T. Receptor-Mediated Transfection

Still further, a nucleic acid may be delivered to a target cell via receptor mediated delivery vehicles. These take advantage of the selective uptake of macromolecules by receptor mediated endocytosis that will be occurring in a target cell. In view of the cell type specific distribution of various receptors, this delivery method adds another degree of specificity to the present invention.

Certain receptor mediated gene targeting vehicles comprise a cell receptor specific ligand and a nucleic acid binding agent. Others comprise a cell receptor specific ligand to which the nucleic acid to be delivered has been operatively attached. Several ligands have been used for receptor mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell specific binding. For example, lactosyl ceramide, a galactose terminal asialganglioside, have been incorporated into liposomes and observed an increase in the uptake of the insulin gene by hepatocytes (Nicolau et al., 1987). It is contemplated that the tissue specific transforming constructs of the present invention can be specifically delivered into a target cell in a similar manner.

U. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA coated microprojectiles to a high velocity allowing them to pierce cell membranes and enter cells without killing them (Klein et al., 1987). There are a wide variety of microprojectile bombardment techniques known in the art, many of which are applicable to the invention.

Microprojectile bombardment may be used to transform various cell(s), tissue(s) or organism(s), such as for example any plant species. Examples of species which have been transformed by microprojectile bombardment include monocot species such as maize (PCT Application WO 95/06128), barley (Ritala et al., 1994; Hensgens et al., 1993), wheat (U.S. Pat. No. 5,563,055, incorporated herein by reference), rice (Hensgens et al., 1993), oat (Torbet et al., 1995; Torbet et al., 1998), rye (Hensgens et al., 1993), sugarcane (Bower et al, 1992), and sorghum (Casas et al., 1993; Hagio et al., 1991); as well as a number of dicots including tobacco (Tomes et al, 1990; Buising and Benbow, 1994), soybean (U.S. Pat. No. 5,322,783, incorporated herein by reference), sunflower (Knittel et al 1994), peanut (Singsit et al., 1997), cotton (McCabe and Martinell, 1993), tomato (VanEck et al. 1995), and legumes in general (U.S. Pat. No. 5,563,055, incorporated herein by reference).

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into a cell (e.g., a plant cell) by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

V. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co expressed with other selected RNAs or proteinaceous sequences in the same host cell. Co expression may be achieved by co transfecting the host cell with two or more distinct recombinant vectors. Alternatively, a single recombinant vector may be constructed to include multiple distinct coding regions for RNAs, which could then be expressed in host cells transfected with the single vector.

A tissue may comprise a host cell or cells to be transformed with a TFIIS inhibitor or polynucleotide encoding same. The tissue may be part or separated from an organism. In certain embodiments, a tissue may comprise, but is not limited to, adipocytes, alveolar, ameloblasts, axon, basal cells, blood (e.g., lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, testes, and all cancers thereof.

In certain embodiments, the host cell or tissue may be comprised in at least one organism. In certain embodiments, the organism may be, but is not limited to, a prokayote (e.g., a eubacteria, an archaea) or an eukaryote, as would be understood by one of ordinary skill in the art.

Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F, lambda, prototrophic, ATCC No. 273325), DH5α, JM109, and KC8, bacilli such as *Bacillus subtilis*; and other enterobacteriaceae such as *Salmonella typhimurium, Serratia marcescens*, various *Pseudomonas* specie, as well as a number of commercially available bacterial hosts such as SURE® Competent Cells and SOLOPACK® Gold Cells (STRATAGENE®, La Jolla). In certain embodiments, bacterial cells such as *E. coli* LE392 are particularly contemplated as host cells for phage viruses.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

W. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

It is contemplated that the proteins, polypeptides or peptides produced by the methods of the invention may be "overexpressed", i.e., expressed in increased levels relative to its natural expression in cells. Such overexpression may be assessed by a variety of methods, including radiolabeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g., visible on a gel.

In some embodiments, the expressed proteinaceous sequence forms an inclusion body in the host cell, the host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g. 8M) or chaotropic agents such as guanidine hydrochloride in the presence of reducing agents, such as β mercaptoethanol or DTT (dithiothreitol), and refolded into a more desirable conformation, as would be known to one of ordinary skill in the art.

VII. Screening for Modulators of the Protein Function

The present invention comprises methods for identifying modulators of the function of TFIIS and/or GDOWN1, although the disclosure will refer to TFIIS as merely the exemplary embodiment. These assays may comprise random screening of large libraries of candidate substances; alternatively, the assays may be used to focus on particular classes of compounds selected with an eye towards structural attributes that are believed to make them more likely to modulate the function of TFIIS. Alternatively, both assays may be employed concomitantly or in succession. By function, it is meant that one may assay for the ability to affect transcription, such as to affect RNAP for transcription, for example.

To identify a TFIIS modulator, one generally will determine the function of TFIIS in the presence and absence of the candidate substance, a modulator defined as any substance that alters function of TFIIS. For example, a method generally comprises:

(a) providing a candidate modulator;

(b) admixing the candidate modulator with an isolated compound or cell, or a suitable experimental animal;

(c) measuring one or more characteristics of the compound, cell or animal in step (c); and (d) comparing the characteristic measured in step (c) with the characteristic of the compound, cell or animal in the absence of the candidate modulator, wherein a difference between the measured characteristics indicates that the candidate modulator is, indeed, a modulator of the compound, cell or animal.

Assays may be conducted in cell free systems, in isolated cells, or in organisms including transgenic animals.

It will, of course, be understood that all of the screening methods of the present invention are useful in themselves notwithstanding the fact that effective candidates may not be found. The invention provides methods for screening for such candidates, not solely methods of finding them.

A. Modulators

As used herein the term "candidate substance" refers to any molecule that may potentially inhibit or, alternatively, enhance TFIIS activity. The candidate substance may be a protein or fragment thereof, a small molecule, or even a nucleic acid molecule, for example, such as an siRNA. In some embodiments, a high throughput assay may be employed to identify modulators, such as is described in the Examples.

It may prove to be the case that the most useful pharmacological compounds will be compounds that are structurally related to other inhibitors of transcription factors. Using lead compounds to help develop improved compounds is know as "rational drug design" and includes not only comparisons with known inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, that have different susceptibility to alteration or that may affect the function of various other molecules. In a specific approach, one would generate a three-dimensional structure for a target molecule, or a fragment thereof. This could be accomplished by x-ray crystallography, computer modeling or by a combination of both approaches, for example.

It is also possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially-generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor according to the present invention may be one which exerts its inhibitory or activating effect upstream, downstream or directly on TFIIS. Regardless of the type of inhibitor or activator identified by the present screening methods, the effect of the inhibition or activator by such a compound results in modulation of TFIIS, such as inhibition of the activity of TFIIS, as compared to that observed in the absence of the added candidate substance.

B. In Vitro Assays

A quick, inexpensive and easy assay to run is an in vitro assay. Such assays generally use isolated molecules and can be run quickly and in large numbers, thereby increasing the amount of information obtainable in a short period of time. A variety of vessels may be used to run the assays, including test tubes, plates, dishes and other surfaces, such as dipsticks or beads, for example.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

An exemplary technique for high throughput screening of compounds is described in WO 84/03564. Large numbers of small peptide test compounds are synthesized on a solid substrate, such as plastic pins or some other surface. Bound polypeptide is detected by various methods.

C. In Cyto Assays

The present invention also contemplates the screening of compounds for their ability to modulate TFIIS in cells. Various cell lines can be utilized for such screening assays, including cells specifically engineered for this purpose.

Depending on the assay, culture may be required. The cell is examined using any of a number of different physiologic assays. Alternatively, molecular analysis may be performed, for example, looking at protein expression, mRNA expression (including differential display of whole cell or polyA RNA) and others.

D. In Vivo Assays

In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to the function of a particular compound (e.g., enzyme, receptor, hormone) or cell (e.g., growth, tumorigenicity, survival), or instead a broader indication such as behavior, anemia, immune response, etc.

Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

VIII. Pharmaceutical Preparations

Pharmaceutical compositions of the present invention comprise an effective amount of one or more agents that inhibit TFIIS and/or GDOWN1 and may include one or more additional agents, wherein any of the agents are dissolved or dispersed in or provided with a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that comprises at least one TFIIS modulator (which for illustrative purposes will be referred to as an inhibitor) and, in some embodiments, an additional active ingredient, will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The TFIIS and/or GDOWN1 inhibitor may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The TFIIS and/or GDOWN1 inhibitor may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include the agent that inhibits TFIIS and/or GDOWN1, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the TFIIS inhibitor may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/ kg/body weight, about 200 microgram/kg/body weight, about 350 microgram/kg/body weight, about 500 microgram/ kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, the TFIIS and/or GDOWN1 inhibitor is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629, 001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, TFIIS inhibitor may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641, 515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound TFIIS and/or GDOWN1 inhibitor may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

IX. Combination Treatments

In certain aspects, the therapy of the invention may be combined with other agents that are effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. The compositions of the present invention are considered anti-cancer agents.

More generally, these other compositions or methods would be provided in a combined amount effective to kill or inhibit proliferation of the cell. This process may involve contacting the cells with the TFIIS and/or GDOWN1 inhibitor, which may be referred to as the first agent, and the second agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that the TFIIS and/or GDOWN1 inhibitor therapy could be used similarly in conjunction with chemotherapeutic, radiotherapeutic, or immunotherapeutic intervention, in addition to other pro-apoptotic or cell cycle regulating agents, for example.

Alternatively, the inventive therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, wherein inventive therapy is "A" and the secondary agent, such as radio- or chemotherapy, is "B":

```
A/B/A  B/A/B  B/B/A  A/A/B  A/B/B  B/A/A  A/B/B/B

B/A/B/B  B/B/B/A  B/B/A/B  A/A/B/B  A/B/A/B  A/B/B/A

B/B/A/A  B/A/B/A  B/A/A/B  A/A/A/B  B/A/A/A  A/B/A/A

A/A/B/A
```

Administration of the therapeutic agents of the present invention to a patient will follow general protocols for the administration of chemotherapeutics, taking into account the toxicity, if any, of the composition. It is expected that the treatment cycles would be repeated as necessary. It also is contemplated that various standard therapies, as well as surgical intervention, may be applied in combination with the described hyperproliferative cell therapy.

A. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with the inventive therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Genes

In yet another embodiment, the secondary treatment is a gene therapy in which a therapeutic polynucleotide is administered before, after, or at the same time as the inventive TFIIS inhibitor. A variety of proteins are encompassed within the invention, some of which include inducers of apoposis and/or inhibitors of cell proliferation, for example.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

X. Kits of the Invention

Any of the compositions described herein may be comprised in a kit. In a non-limiting example, an agent that inhibits TFIIS and/or GDOWN1 and an additional agent, including an additional anti-cancer agent, in specific embodiments, may be comprised in a kit. The kits will thus comprise its contents in suitable container means.

The kits may comprise a suitably aliquoted agent that inhibits TFIIS and/or GDOWN1, a pharmaceutical carrier, such as a lipid, and including a liposome, and/or an additional agent. Compositions of the present invention, whether labeled or unlabeled, as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the TFIIS and/or GDOWN1 inhibitor, lipid, additional agent, and any other reagent containers in close confinement for commercial sale. Such containers may include injection or blow molded plastic containers into which the desired vials are retained.

Therapeutic kits of the present invention are kits that may comprise an agent that inhibits TFIIS and/or GDOWN1, such as siRNA molecules that are directed to TFIIS and/or GDOWN1. Additional agents may include chemical compounds or pharmaceutically acceptable salts thereof, a protein, polypeptide, peptide, inhibitor, gene, polynucleotide, vector and/or other effector. Such kits may generally contain the compositions in a pharmaceutically acceptable formulation. The kit may have a single container means, and/or it may have distinct container means for each compound.

When the components of the kit are provided in one and/or more liquid solutions, the liquid solution is an aqueous solution, with a sterile aqueous solution being particularly preferred. The agent may also be formulated into a syringeable composition. In this case, the container means may itself be a syringe, pipette, and/or other such like apparatus, from which the formulation may be applied to an affected area of the body, injected into an animal, and/or even applied to and/or mixed with the other components of the kit. The formulation may be suitable for systemic or local delivery.

In some embodiments, the components of the kit may be provided as dried powder(s). When reagents and/or components are provided as a dry powder, the powder can be reconstituted by the addition of a suitable solvent. It is envisioned that the solvent may also be provided in another container means and may be sterile.

The container means will generally include at least one vial, test tube, flask, bottle, syringe and/or other container means, into which the inhibitory formulation is placed, and preferably is suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the ultimate composition within or to the body of an animal. Such an instrument may be a syringe, pipette, forceps, and/or any such medically approved delivery vehicle.

In specific embodiments, the kit comprises an additional composition for treatment of cancer, including a chemotherapeutic drug. The kit may be tailored to include chemotherapeutic drugs suitable for the type of cancer being treated. For example, kits may be formulated for individuals with breast cancer and may include in addition to the TFIIS inhibitor one or more breast cancer drugs, such as Taxol, herceptin, tamoxifen, paclitaxel, gemcitabine, and so forth.

XI. EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Determining the Effects of Transcription Factor Inhibition Employing RNAi

To determine the effects of TFIIS inhibition in cancer cells, the inventors employed RNAi (siRNA, for example). Two exemplary double stranded inhibitory RNA (dsRNA), which are provided below, were designed according to the kit manufacturer to regions of TFIIS that have no cross homology to other human genomic sequences. DNA templates were obtained from MWG Biotech (High Point, N.C.).

1. An exemplary target mRNA sequence: 5'-AAUGCUA-UUCGCAAGCAGAGU (SEQ ID NO:5)

Exemplary Templates for Target mRNA

```
antisense template:
                                    (SEQ ID NO:6)
5' - aatgctattcgcaagcagagt/cctgtctc sense template:
                                    (SEQ ID NO:7)
5' - aaactctgcttgcgaatagca/cctgtctc
```

2. An exemplary target mRNA sequence: 5'-AACAGGG-GAUGACUACAUUGC (SEQ ID NO:8)

Exemplary Templates for Target mRNA

```
antisense template:
                                    (SEQ ID NO:9)
5' - aacagggatgactacattgc/cctgtctc sense template:
                                    (SEQ ID NO:10)
5' - aagcaatgtagtcatcccctg/cctgtctc
```

Figure 2:
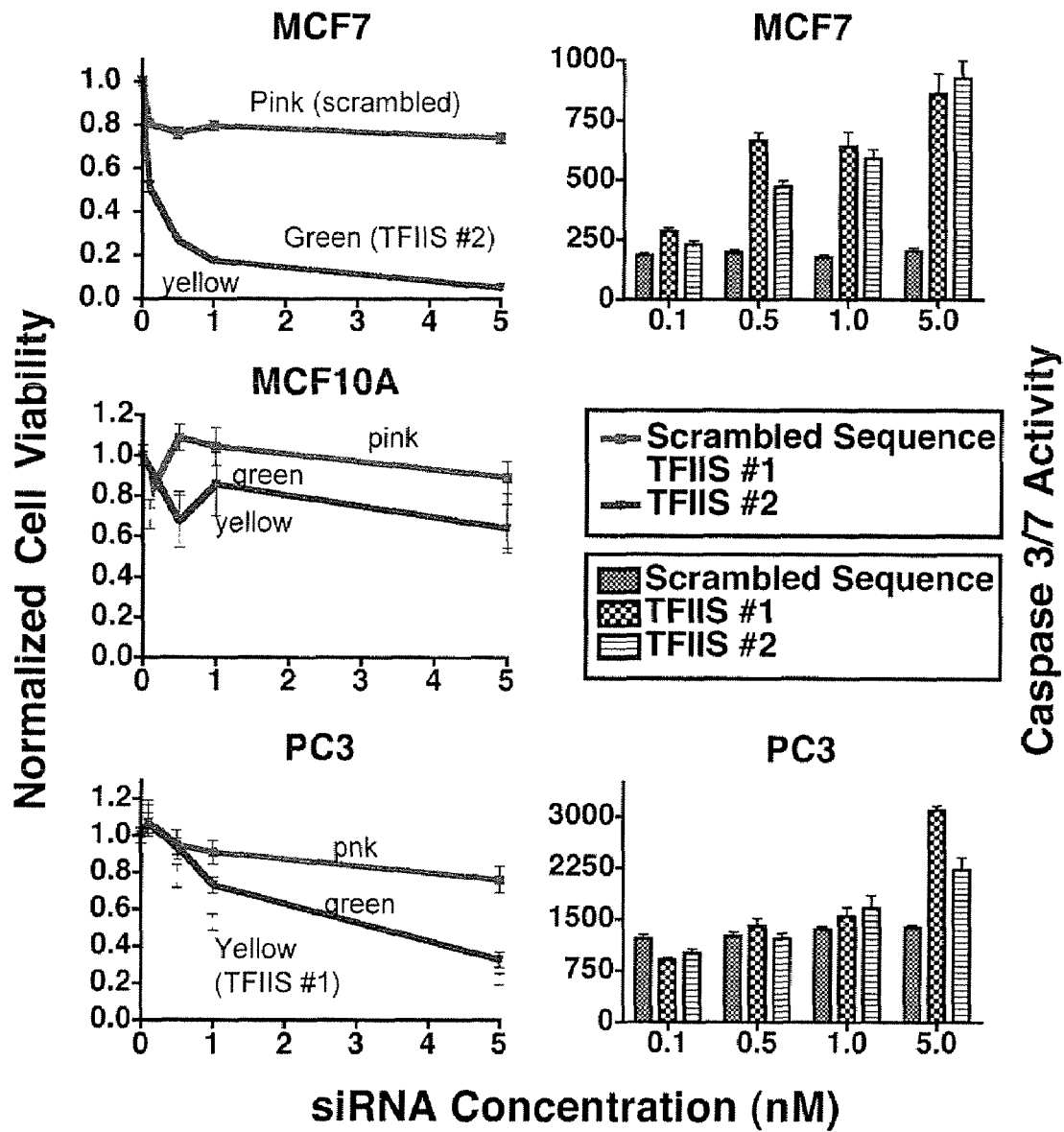
FIG. 2 shows the effect of TFIIS siRNA on cell growth. All cell lines as indicated were subjected to siRNA directed at TFIIS and are represented in the figure by yellow template 1 and Green template 2, if the figure is shown in color. Pink represents a scrambled GAPDH sequence shown to have no homology to any sequence in humans, rats, or mice as a negative control (Ambion). The normalized cell viability represents the percentage of viable cells compared to cells transfected with transfection agent alone.

Initially, both TFIIS siRNAs were tested for reduction of PC3 (prostate) and MCF7 (breast) tumor cell growth (FIG. 2). MCF10A non-cancerous breast cells were tested as well. Experiments were performed in quadruplicate with a minimum of 2 independent experiments (see Example 3). Reproducible results indicate that in breast and prostate cancer cell lines MCF7 and PC3 cell growth was severely limited (FIG. 2). Most importantly, the MCF10A non-cancerous cell line did not display significant growth inhibition. Although more cell lines will be tested, results strongly indicate that a true cancer cell specificity is attained, as exemplary non-cancerous breast cells were not affected. The negative control siRNA shows limited decrease in cell growth. Cell growth inhibition in both MCF7 and PC3 cell lines is associated with apoptosis as indicated in FIG. 2. Assessment of apoptosis in MCF10A is performed. In addition, MCF10A cells do not undergo cell death.

Real-time PCR validated the specificity of siRNA targeting of TFIIS, as antibodies were not commercially available in this particular case. siRNA directed at β-actin was employed as an internal control. Real-time PCR of mRNA from MCF7 cells collected 72 hours after treatment with 5 nM siRNA demonstrates that the TFIIS transcript is 62% down-regulated with a standard deviation of 1.41 compared to control, as calculated by the comparative delta-delta CP method (Table 1, see detailed but exemplary methods in Example 3) In specific embodiments, RT-PCR is performed on all cell lines employed.

Table 1 exhibits the relative expression of TFIIS compared to β-actin in siRNA treated MCF7 cells. The siRNA was employed at 5 nM. The control consisted of transfection agent without siRNA. Two separate experiments were performed with n=3, and the cycle threshold was determined (see exemplary methods in Example 3). The PCR efficiency for B-Actin and TFIIS was 2.042 and 2.171, respectively.

| PCR | β-actin Cycle threshold | | TFIIS Cycle threshold | | Relative ratio |
|---|---|---|---|---|---|
| Reaction | Vehicle | siRNA | Vehicle | siRNA | of expression |
| Reaction 1 | 18.2 | 16.6 | 28.2 | 27.4 | |
| | 17.9 | 16.2 | 27.5 | 27.6 | |
| | 17.7 | 16.4 | 27.8 | 27.9 | |
| Average | 17.93 | 16.4 | 27.83 | 27.63 | 39.2% |
| Reaction 2 | 19.4 | 17.4 | 28.6 | 28.1 | |
| | 18.9 | 17.9 | 28.7 | 28.9 | |
| | 19.0 | 17.3 | 28.9 | 28.7 | |
| Average | 19.1 | 17.53 | 28.73 | 28.56 | 37.2% |
| Mean | | | | | 38.2% |
| S.D. | | | | | 1.41 |

Example 2

Mechanism of Cancer Cell Death with TFIIS Inhibition

Inhibition with siRNA directed at TFIIS may be extended to additional breast and prostate cancer and noncancer cell lines to enable a stronger generalization of apoptosis in cancer cells, in certain aspects of the invention. For prostate cancer, exemplary PC3 cells (hormone-independent), LnCAP (hormone-dependent) cells, as well as one or two non-cancerous cell lines (PWR-1E and PNT1A, for example) may be utilized. For breast cancer, for example, exemplary MCF7 may be utilized, which has the estrogen receptor, in addition to MDA-MB-231 that lacks estrogen receptor, and MCF10A, which is a non-tumorigenic cell line. It is determined if inhibition of TFIIS expression causes cell death in both hormone-dependent and hormone-independent cell lines. In certain aspects of the invention, both hormone-dependent and hormone-independent cell lines will go through apoptosis, although in alternative embodiments the cell lines will only one type of cell line will go through apoptosis.

Initially, western analysis may be performed in order to test affects of siRNA targeting of TFIIS on known upregulated or downregulated proteins involved in breast and prostate cancer, for example. These include the following exemplary gene products: androgen receptor, c-myc, BCL2, c-fos, P53, Estrogen Receptor, Cyclin D1, BRCA1 and housekeeping genes, such as β-actin and tubulin as controls, for example. This would be informative regarding whether TFIIS affects expression of key but exemplary breast and prostate cancer genes. If expression of these is reduced compared to controls, it is further characterized whether the effects are directly on these genes.

In embodiments wherein downregulation of key prostate and breast cancer proteins is observed, the inventors can test for TFIIS-responsive arrest sequences employing an exemplary in vitro tailed template assay, since tailed template activity correlates with in vivo arresting of the same sequences (Keene et al., 1999; Shor et al., 1995). Tailed templates are synthesized with the androgen receptor T rich region (bases 814-830, GenBank® number gi21322251) and BCL-2, which is another prostate cancer marker that has a poly T rich tract (bases 2761-87, GenBank® number gi28144172). For breast cancer, the Estrogen receptor 1 T rich site (bases 4220-4236 of GenBank® number gi62821793) and that of Cyclin D1 (bases 3237-3250, GenBank® number gi16950654) is tested. In embodiments wherein these are valid Poly T arrest sites and TFIIS allows for readthrough, this would provide a mechanism for breast and prostate cancer cell death when treated with siRNA directed at TFIIS. In further specific embodiments of the invention, TFIIS inhibition will directly affect genes with long poly T tracks.

In other embodiments of the invention, Genechips are performed on a minimum of two different TFIIS siRNA-inhibited breast and prostate cancer cell lines: one androgen-dependent and one androgen-independent, as well as corresponding non-cancerous breast and prostate cell lines for comparison. RNA is purified from each cell line treated with vehicle alone, TFIIS siRNA, and a scrambled siRNA negative control.

In particular aspects of the invention, key breast and prostate genes are reduced in expression when cancer cells are treated with TFIIS-directed siRNA. In certain aspects of the invention, other novel EST's are identified that share upregulation or downregulation in TFIIS-inhibited breast and prostate cancer cells yet are not present in non-cancerous cell lines. The gene expression profile is useful for indicating likely mechanisms for TFIIS inhibition. In other specific embodiments, several genes with polyT tracts are identified that are downregulated because readthrough is ineffective without TFIIS. In these embodiments, poly T tracts are searched for in downregulated EST's either visually or by computer, such as with our currently copyrighted program (Txu 1-166-822).

Although there exist breast and prostate specific genechips, for example the prostate genechip HS-031 from Bioscience corporation, a larger chip array may serve needs better, as effects of TFIIS inhibition on a large part of the genome can be studied. It is determined if expression patterns of some genes from hormone-dependent and hormone-independent cancers from breast and prostate origin are shared and to what extent. In specific embodiments, therefore, one will employ the Affymatrix genearray U133 with over 40,000 different ESTs.

EST's newly identified to be upregulated or downregulated as a result of siRNA inhibition of TFIIS are targeted for siRNA inhibition themselves in breast and prostate cancer and non-cancer cells as a control. Cell viability is then determined, such as was performed for TFIIS. This will help delineate if genes downstream of TFIIS are sufficient to produce the apoptotic effect observed for TFIIS inhibition. In certain embodiments, one gene alone would suffice for the apoptotic effect, such as the clinically targeted myc, for example, which contains a TFIIS responsive arrest site. In alternative embodiments, differential regulation in several genes is responsible for the apoptotic effect. Regardless, the benefit of targeting of TFIIS is that it induces apoptosis by multiple pathways in cancer cells.

Example 3

High Throughput Assay

An exemplary high throughput assay is described, although any suitable assay may be employed alternatively or additionally.

Purification of Mammalian RNAP

In one embodiment of an assay, purified RNAP is utilized. Although in some embodiments the source may be human, the amount of pure RNAP obtainable from tissue culture is not sufficient for high throughput screens, for example. We are therefore pursuing bovine thymus RNAP which is in plenty supply, and functions with human transcription factors such as TFIIS (Yoo et al., 1991). In addition, high throughput screening requires milligram quantities of ultra pure RNAP. RNAP binds numerous transcription factors and screening of RNAP in the presence of these factors could likely invalidate or may cause irreproducible results. Previously, purification of mammalian RNAP has proven challenging resulting in either fair amounts of impure non-homogeneous material, or minor and insufficient amounts of pure material (Dahmus, 1981; Hodo and Blatti, 1977; Benson et al., 1978).

After considerable effort, the present inventors have overcome the challenges involved in mammalian RNAP purification. Calf Thymus RNAP is now purified and produced at 2.0-4.0 mg/kg of calf thymus (FIG. 3A). The present TFIIS tailed template activity assays (Gnatt et al., 1997) require 1-2 μg RNAP per assay such that sufficient quantities of ultrapure RNAP is now in hand.

Purification of Human TFIIS

The present inventors have PCR subcloned human TFIIS cDNA into the histidine encoding N-terminal tagged bacterial expression vector pET21 (Invitrogen). Human TFIIS is currently purified by Ni-NTA (Qiagen) affinity chromatography followed by a final step employing MonoS HPLC (Biorad, FIG. 3B).

Current TFIIS Inhibition Assay

Figure 5:
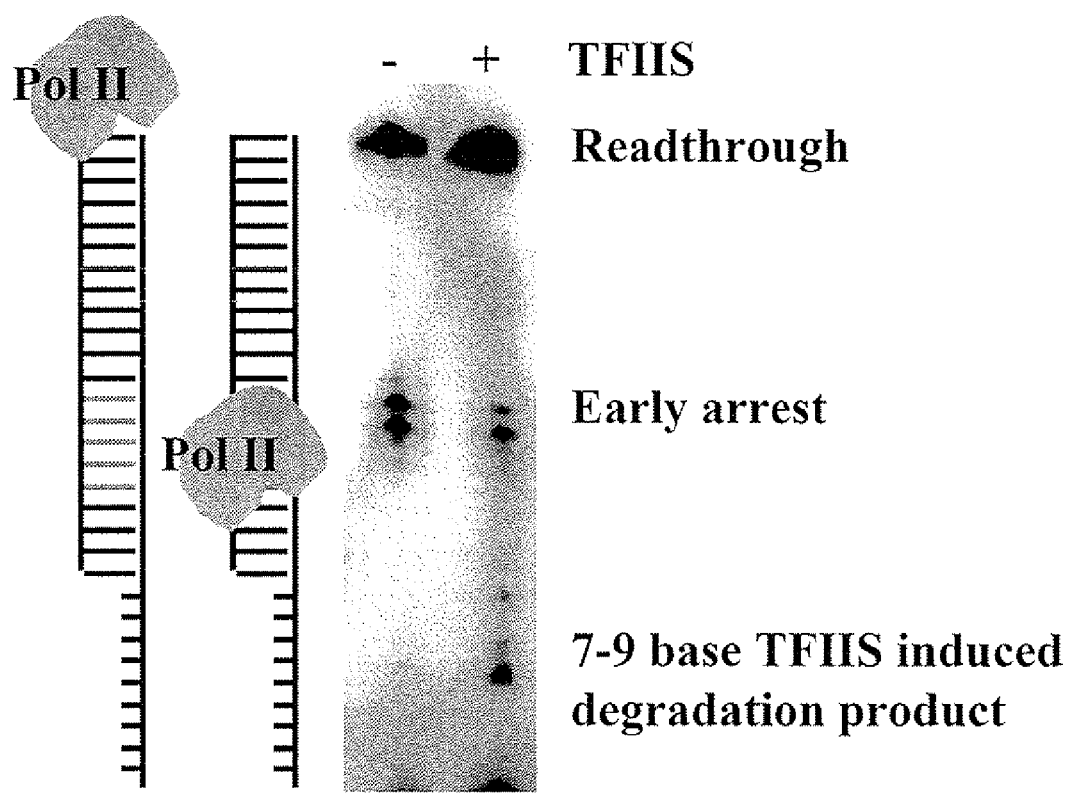
FIG. 5 demonstrates an exemplary transcription assay. RNAP is schematically depicted reading through and arresting on a tailed template. Blue represents the early arrest site in a color representation of the figure. Early arrest normally occurs with a portion of RNAP on tailed templates when the RNA length reaches 15-16 bases. The experimental assay is performed as previously described (Gnatt et al., 1997). Briefly, $P^{32}$-labeled RNA products generated from template Temp0 and RNAP with and without TFIIS were separated on a 15% polyacrylamide-Urea-TBE gel.

Employing tailed templates as listed in FIG. 4, the inventors have established a TFIIS activity assay as depicted in FIG. 5 (Gnatt et al., 1997). Data below describes certain efforts at altering the assay to allow for high throughput screening as part of this invention.

```
Temp0 (+)    AAAAAGAAGGGGCTTTGCGGAACGAGCGACCACAA-5'
             (SEQ ID NO:1)
Temp0 (-)    TTTTTCTTCCCCGAAACGCCTTGCTCGCTGGTGTTCCCC
             CCCCCCCC-3'
             (SEQ ID NO:2)

TempT5 (+)   GAAGGGGCGAGGCGGGTTTTTCGACCACAA-5'
             (SEQ ID NO:3)
TempT5 (-)   CTTCCCCGCTCCGCCCAAAAAGCTGGTGTTCCCCCCCCC
             CCC-3'
             (SEQ ID NO:4)
```

Tailed templates to date have been shown to contain an early arrest site (Gnatt et al., 1997). Approximately 30% of the RNAP molecules are unable to readthrough the early arrest site. The presence of TFIIS results in increased readthrough of the early arrest site as well as degradation products of 7-9 bases. In such an assay if TFIIS were inhibited we would not see any 7-9 base RNA products and the amount of readthrough would be reduced.

The assay as depicted is not suited for high throughput screening. First, screening thousands of small molecules can not be accomplished with polyacrylamide-TBE gels and radiolabeled RNA since it is limited to 30 samples/day. Second radiolabel detection may not be preferred for a safe high throughput system. Third, the 7-9 base TFIIS induced RNA cleavage products were not detectable via mass spectroscopy or a sequencing apparatus. Employing the template in FIG. 5, loss of readthrough product is not a reasonable indicator of TFIIS inhibition as different levels of readthrough with and without TFIIS may be only two-fold depending.

Figure 3:
FIGS. 3A-3B show calf thymus RNAP and TFIIS Coomasie-stained SDS Polyacrylamide gels.

The inventors therefore generated a template that allows for full arresting at the early arrest site and readthrough only in the presence of TFIIS. This is advantageous for devising a high throughput screen, as the longer readthrough would be easier to detect than the 7-9 base TFIIS induced products. To this aim extra T residues, known to enhance RNAPII arresting were added near or in the early arrest site resulting in template TempT5 (FIG. 3 above).

Figure 6:
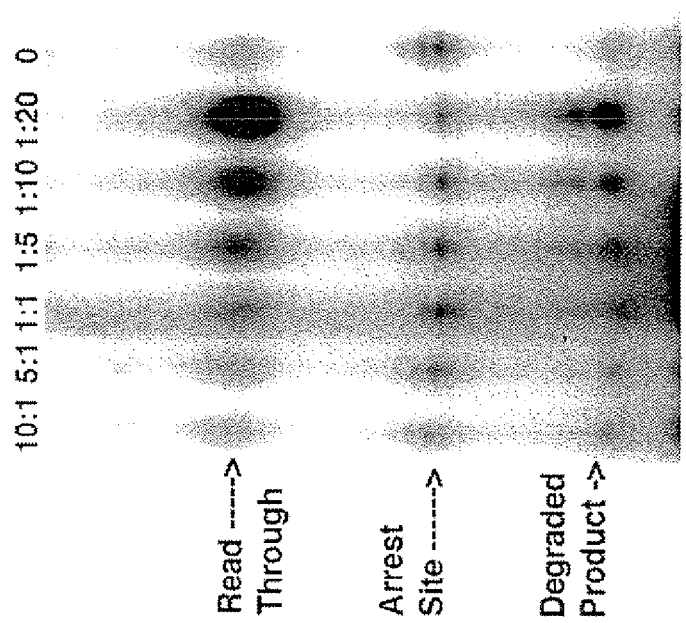
FIG. 6 shows that mammalian RNAP reads through the early arrest site in the presence of TFIIS. Assay conditions were similar to that of FIG. 5. Increasing amounts of TFIIS were employed with a constant amount of RNAP and template TempT5. The ratio between RNAP and TFIIS is indicated. Readthrough of the arrest site is observed to be TFIIS-dependent. In lane 0, no TFIIS was employed, and nearly all of the RNAP arrested.

FIG. 6 demonstrates that mammalian RNAP reads through the early arrest site in the presence of TFIIS. Assay conditions were similar to that of FIG. 5. Increasing amounts of TFIIS were employed with a constant amount of RNAP and template TempT5. The ratio between RNAP and TFIIS is indicated. Readthrough of the arrest site is observed to be TFIIS dependant. In lane 0, no TFIIS was employed and nearly all the RNAP arrested.

Figure 7:
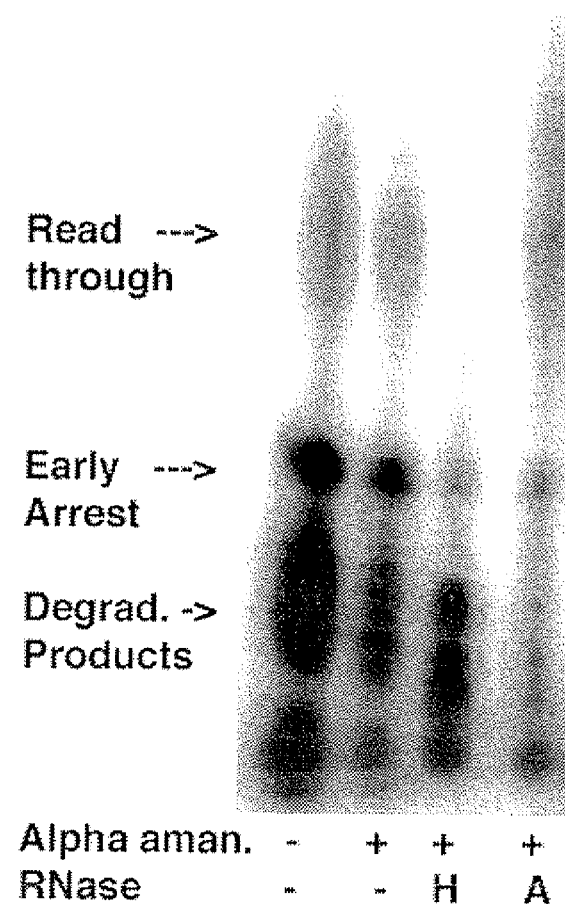
FIG. 7 demonstrates that RNA displaces non-template DNA in tailed template assays. TempT5 was employed in the tailed template assay with yeast RNAP and TFIIS. After 20 minutes, alpha amanitin was added as indicated to inhibit RNAP function followed by RNase A or H. RNase H digests RNA in an RNA/DNA hybrid. In the image, RNase H induced degradation of the readthrough product, thereby proving that the RNA is hybridized to the template DNA. RNase A, which digests single stranded RNA, has no effect on readthrough products, further proving that the RNA has displaced non-template DNA to form an RNA/DNA hybrid.

In one embodiment of the invention, a high throughput screen could employ template TempT5. Inhibition of TFIIS would result in a fully arrested product. Controls not shown are assays performed with TFIIS and without RNAP to rule out bacterial RNA Polymerases. Ruling out of contaminating RNAase activity was by the addition of alpha amanitin, which inhibits RNAP after arresting followed by the addition of TFIIS where no 7-9 base degradation products were observed (FIG. 7).

It is important to note that the RNA strand can displace the non-template DNA strand when using yeast RNAP. This information is relevant to another embodiment of assay development and detection of the readthrough using non-radioactive methodologies described elsewhere herein.

Thus, the inventors currently have a very efficient mammalian TFIIS assay employing template TempT5. TFIIS activity coincides with readthrough. Inhibition of TFIIS would result in no or little readthrough product.

Modification of Current Assay for High Throughput Screening

Figure 8:
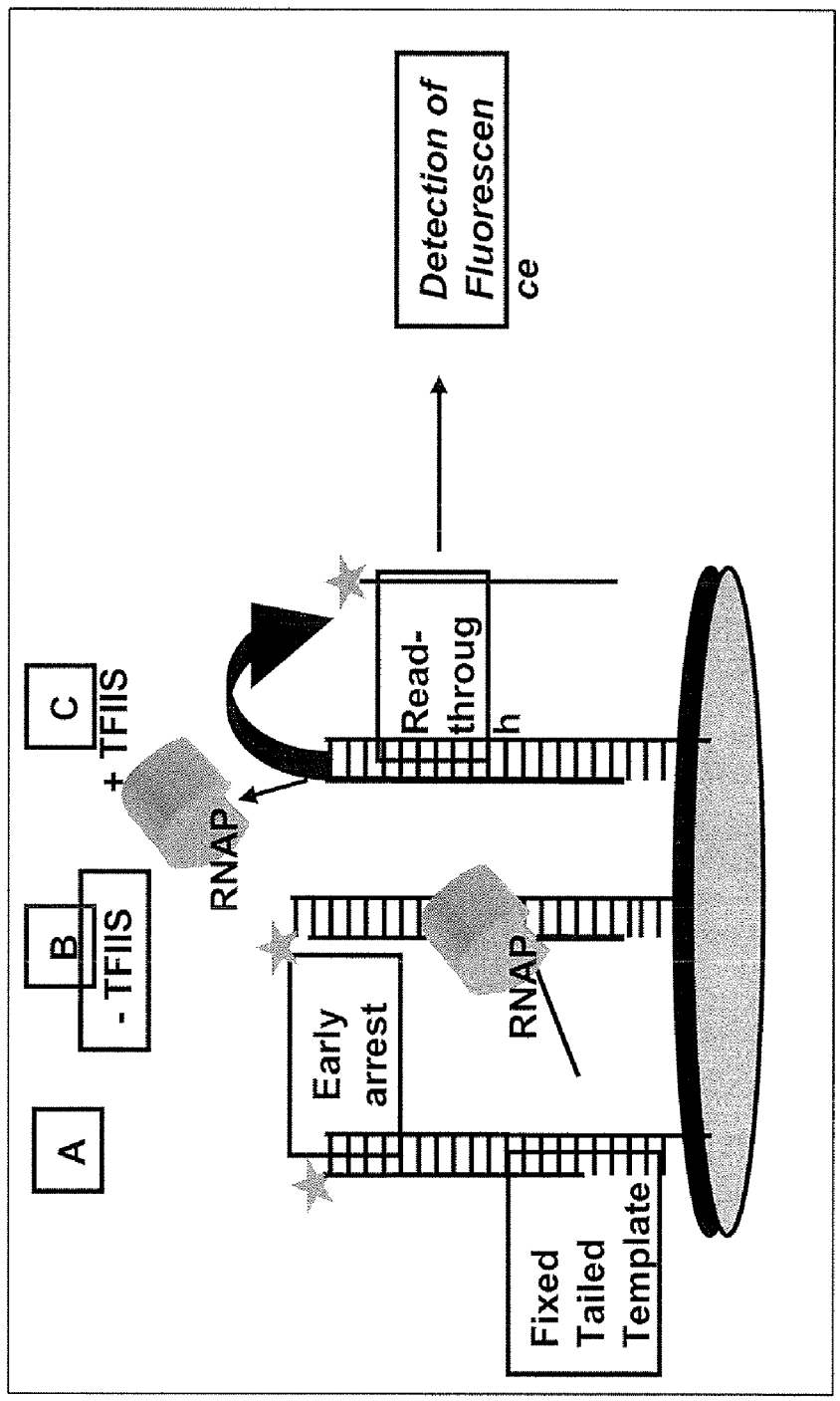
FIGS. 8A-8C provide an exemplary high throughput assay.

In another embodiment of assay development under this proposal is to employ a fluorescent-labeled non-template strand instead of radioactive RNA. As it occurs, the newly synthesized RNA remains bound to the template DNA strand, displacing the nontemplate strand when employing yeast RNAP. In our new assay design, the template strand will be bound to 96 well plates or higher. The fluorescent-labeled non-template strand will be displaced into the supernatant by the growing RNA chain (FIG. 8). The RNAase A and H sensitivity experiment may be repeated with calf thymus RNAP to verify that the non-template strand is displaced by the RNA as we assume it will be. If not a high throughput detection of the RNA can be accomplished similar to a recently published in vitro high throughput screen involving RNAP (Garcia-Martinez et al., 2002).

Figure 9:
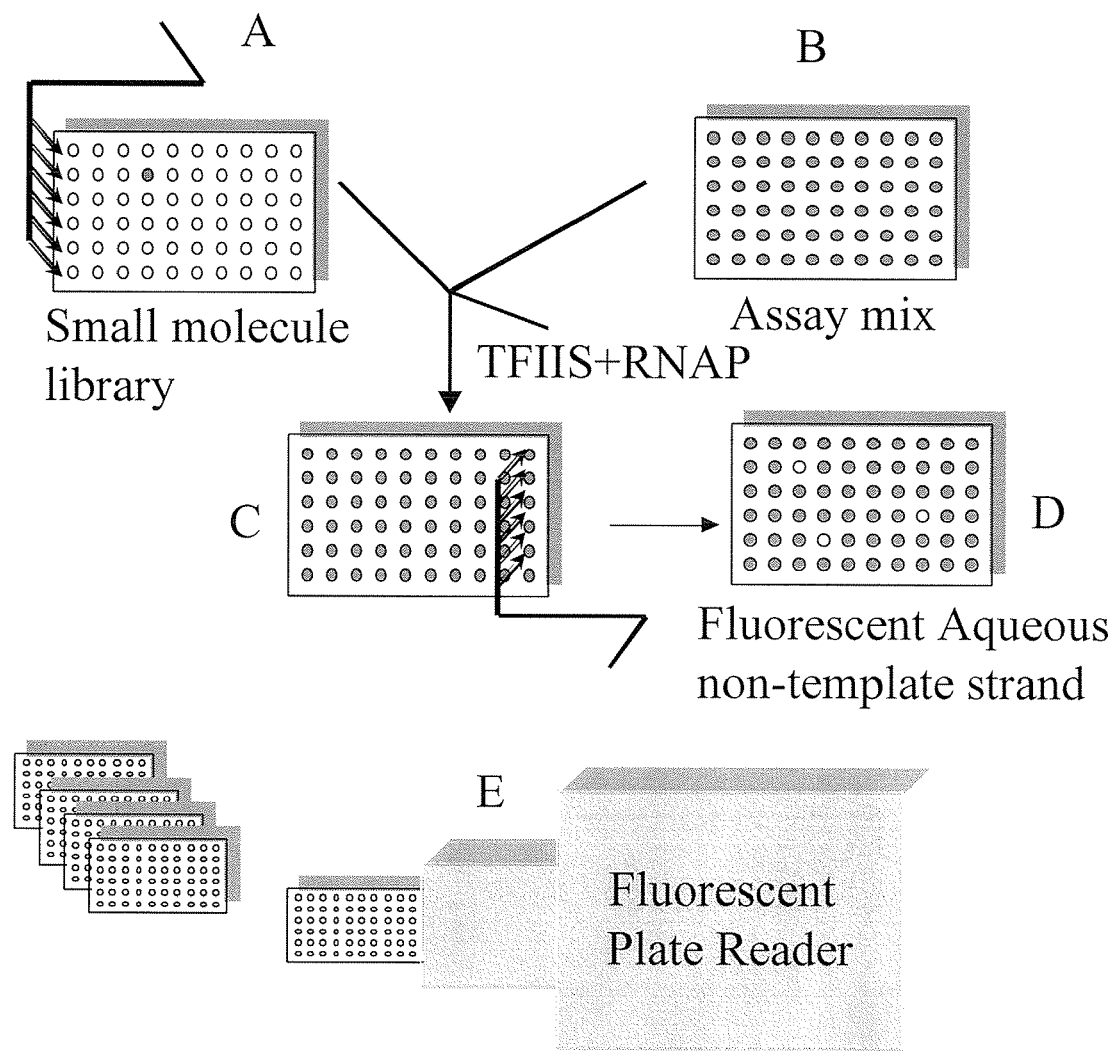
FIGS. 9A-9E demonstrate an exemplary high throughput assay.

FIG. 9 illustrates a high throughput assay in one specific embodiment of the invention. If TFIIS and RNAP are active, then the supernatant of the reaction would contain displaced fluorescent non-template strand. If TFIIS or RNAP are inactivated by a small molecule from a library no fluorescent signal would be observed. Lack of readthrough can therefore be due to inhibition of RNAP or TFIIS. To differentiate between inhibition of RNAP and TFIIS, the standard radioactive assay described elsewhere herein, for example, may be employed, which can differentiate between the two. Both RNAP and TFIIS inhibitors may be identified in such a screen, in certain aspects of the invention. Inhibitors to RNAP themselves could also be an important indirect finding for the study of transcription.

Exemplary Assay Format

Plate formats with covalently-linked template oligos and hybridized fluorescent-labeled nontemplate strand are employed in specific embodiments over beads, since they allow for effective robotic handling. However, in other embodiments the system is developed at least initially with streptavidin beads and biotynylated oligos for ease of use and to reduce expenditure before transferring the system to plates.

Detection of the Fluorescent Signal

After the reaction the supernatant is collected by a robotic system and transferred to a new plate where fluorescence is measured by a plate reader. Two robotic workstations, a Beckman Biomek 2000 and a Matrix Plate Mate, may be employed. A Wallac plate reader and/or additional plate readers may be employed, if necessary.

Chemical Libraries to be Employed in Screen

Ultimately, about 10-100,000 small molecules may be screened to disclose a few TFIIS inhibitors. More than one small molecule inhibitor may be identified by the screen. In specific embodiments of the invention, a random small molecule library is employed. However, in particular aspects the library comprises nucleotide analogues and other DNA interacting small molecules, for example, as these may have an effect on RNAP-TFIIS complex function by altering DNA structure.

In a specific embodiment of the invention, the high throughput assay employs 96-well plates with about 90 different small molecules/plate, with controls comprising RNAP alone, RNAP with alpha amanitin, which inhibits RNAP, TFIIS alone, and RNAP and TFIIS without template. Several library providers are available, for example Chemdiv and TimTech. Chembridge has a well-diversified collection of small molecules that may be better suited for our efforts at $1.25/compound (minimum 10,000 compounds) with 40,000 compounds to be screened. Mammalian RNAP is highly sensitive and gradually denatures in the presence of oxygen. Certainly, on-site screening allows for maximum effectiveness with RNAP and TFIIS activity tested daily in the current assay. Novel inhibitors can also be assayed to differentiate between RNAP and TFIIS inhibition. If a TFIIS inhibitor is not disclosed after screening the 40,000 compounds, alternative embodiments may be employed.

Employ Inhibitors in Cell Based Assay

Once inhibitors are in hand, they are further characterized in a dose-dependent manner in the radioactive assay, for example, and in the cell-based assay with cancerous and non-cancerous cells. Not only will cell viability be studied, but also apoptosis. Finally, genearrays of breast and prostate cancer cells treated with TFIIS inhibitors could also be generated and compared to those performed with siRNA inhibition of TFIIS.

Example 4

Exemplary Materials and Methods for Examples 1-3

Generation of Tailed Templates for Transcription Assays

Templates that were 3' single stranded tailed templates were synthesized by standard methods (MWG, Charlotte, N.C.). Templates were resuspended with their homologous strands in TE buffer (10 mM Tris-Cl pH 7.5 and 1 mM EDTA), heated to 90° C. for two minutes and cooled slowly to room temperature. They were stored at −20° C. until used. Exemplary template sequences are shown in Table 1.

Transcription Assays

RNA polymerase II (1-2 µg) is incubated alone or with TFIIS in a final volume of 20 µl with 20 pmoles of template DNA in 50 mM Tris, pH 7.5, 10 mM magnesium sulfate, 10% glycerol, 2 µM zinc sulfate, 10 mM DTT (dithiothreitol), and 60 mM ammonium sulfate (final concentrations). Nucleoside triphosphates (GE Healthcare) are added at a final concentration of 600 µM ATP, 600 µM CTP, 600 µM UTP, and 50 µM GTP. Labeling of RNA was achieved by the addition of 1 µl of 400 Ci/mmol [$\alpha$-$^{32}$P] GTP (GE Healthcare).

Reactions are incubated for 20 minutes at 28° C. Reactions are terminated by the addition of 0.25% SDS, 0.5 µg/µl proteinase K (final concentrations), followed by incubation of the samples for 45-60 minutes at 40° C., in a total of 150 µl. RNA is then extracted with one volume of a phenol-chloroform mix (1:1 volume ratio) followed by a half volume of chloroform. Precipitation is in the presence of 1 µg glycogen, 0.3 M sodium chloride, and 2.4 volumes of ethanol for 16 hours at −20° C. After centrifugation for 30 minutes at 4° C., samples were resuspended in 13 µl of formamide loading buffer, and 7 µl was loaded on a 6M urea, 15-19% polyacrylamide TBE gel at 50° C. The run was terminated when the bromphenol blue dye reached the bottom. The gel was exposed in a cassette to Kodak film for 6-16 hours and developed in a Kodak developer (M35A X-omat processor).

For RNase digestion experiments, upon completion of the reaction Alpha amanitin (0.05 µg/µl final concentration) was added to stop transcription, followed by RNase A or H. Samples are incubated for 2 minutes, then either RNase H (Invitrogen) 0.1U final concentration, or RNase A (Invitrogen) 10 µg/µl final concentration were added and incubated for 1 hour at 37° C.

Cell Culture

MCF7 and PL45 cell lines were grown in DMEM medium containing 10% FBS and 1% Pencillin/Streptomycin. PC-3 and A549 cell lines were grown in Ham's Medium supplemented with 10% FBS and 1% Pencillin/Streptomycin (Invitrogen).

siRNA Growth Inhibition Assay

Cell viability was determined employing the MTS assay as described by the manufacturer (Promeg; Madison, Wis.). Synthetic siRNAs were created employing the Silencer siRNA Construction Kit (Ambion; Austin, Tex.). Before transfection, all cell lines were seeded in 96-well plates at a concentration of 2000 cells/well. Plates were incubated for 24 hrs at 37° C. Cells were then transfected using their respective growth medium without the presence of antibiotic in the presence of Lipofectamine 2000 Transfection reagent (Invitrogen; Carlsbad, Calif.), and 0.1, 0.5. 1.0, and 5.0 nM siRNA (positive control), a scrambled siRNA (negative control), and each of the TFIIS siRNAs. Cells were then incubated for 72 hrs at 37° C. Vehicle containing Lipofectamine 2000 alone was applied to cells and viable cells considered 100% survival. Assays were performed in quadruplicate with a minimum of two different experiments.

To determine cell viability, media was replaced with MEM without Phenol Red, and MTS reagent was added and allowed to incubate for 2 hrs, at which time the plates were read to collect the data. It was analyzed to obtain the mean and standard error, and graphs were plotted using Prism (Graphpad Software, Inc., CA).

Apoptosis

To assay for programmed cell death, cells were treated as indicated for siRNA, with MTS being substituted by the Caspase-Glo 3/7 assay reagent and plates read as instructed by the manufacturer of the Caspase-Glo system (Promega; Madison, Wis.). Assays were performed in quadruplicate with a minimum of two different experiments. The data was analyzed to obtain the mean and standard error, and graphs were plotted using Prism (Graphpad Software, Inc., CA).

Flow Cytometric Analysis of Apoptosis and Cell Cycle Analysis Using Propidium Iodide Staining Flow cytometric analysis of cellular DNA will be performed following propidium iodide staining method. Briefly, $1\times10^5$ prostate or breast cancer cells will be incubated with vehicle and TFIIS siRNA at 5 nM for 72 hours. The trypsinized cells will be washed in 1×PBS, and then gently resuspended in 0.5 mL of a hypotonic fluorochrome solution (50 μg/mL propidium iodide in 0.1% sodium citrate plus 0.1% Triton X-100). Samples will be stored in the dark at 4° C. until flow cytometric analysis. The percentage of cells that are apoptotic will be measured as the excluding of cellular debris from analysis by raising the forward scatter threshold, and the DNA content of intact nuclei is recorded on a logarithmic scale. Apoptotic cell nuclei containing hypodiploid DNA are enumerated as a percentage of the total population. After measurement of apoptotic cells, the distribution of cells in each phase of the cell cycle is determined using the same samples by the flow cytometric analysis. A FACScan flow cytometer will be performed in the Marlene Stewart Greenbaum Cancer Center core facility, University of Maryland.

DNA Analysis by Agarose Gel Electrophoresis

Fragmented DNA is isolated and analyzed with exemplary breast and prostate cancer cells after incubation with vehicle and TFIIS siRNA. Briefly, $1.5\times10^6$ prostate or breast cancer cells will be incubated with vehicle and TFIIS siRNA at 5 nM for 72 hours, then lysed in 0.5 mL of lysis buffer (0.6% SDS and 10 mM EDTA, pH 7.0). NaCl will be added to a concentration of 1 mM/ml and mixed by inversion. The mixture will be left at 4° C. for 12 hours and then centrifuged at 12,000 g for 15 minutes at 4° C. The supernatant will be incubated with RNAase A (50 μg/ml) at 37° C. for 30 minutes. The supernatant will then be extracted with a 1:1 mixture of phenol and chloroform, precipitated with 75% ethanol, and resuspended in TE buffer (10 mM Tris-Cl, pH 7.8 and 1 mM EDTA). The sample will be subjected to electrophoresis on a 2% agarose gel containing 0.5 μg/mL ethidium bromide.

Real-Time RT-PCR $1.5\times10^6$ breast and prostate cancer cells will be transfected with TFIIS siRNA (5 nM) using Lipofectamine 2000 (Invitrogen) and incubated for 72 hrs. Total RNA is isolated using the Trizol Reagent (Invitrogen). One μg of total RNA from vehicle and siRNA treated breast and prostate cells will be reverse transcribed using the iScript cDNA synthesis kit (Bio-Rad; Hercules, Calif.). An iCycler IQ (Bio-Rad; Hercules, Calif.) is used for analysis via real-time quantitative RT-PCR. Twelve nanograms (ng) of total RNA from a given sample is reverse transcribed and amplified using the iQTM SYBR Green Supermix Kit (Bio-Rad, CA) according to the manufacture's instruction. Beta-actin is used as a standard for each sample tested. The iCycler IQ software optical system 3.1, plots relative fluorescence (measured at 490 nm) during exponential amplification (after correction for background fluorescence) as a function of PCR cycle number, and determines the crossing points (CP) for each RT-PCR reaction. β-actin forward primer are: forward, GCTATCCAGGCTGTGCTATC (SEQ ID NO:11) and reverse, TGTCACGCACGATTTCC (SEQ ID NO:12). TFIIS primers are: forward; 5'-CTTCTGCCTCCTCCTCTC (SEQ ID NO:13) and reverse 5'-CTCCATAGTCCTTGTAATCATC (SEQ ID NO:14). Relative gene expression in the sample is determined using the comparative delta-delta CP method (ΔΔCP) with β-actin as control (Pfaffl, 2001). Optimal and identical real-time amplification efficiencies of the target gene (TFIIS) and reference gene (β-actin) are calculated in the range from 1.5, 3, 6, 12 and 24 ng cDNA input (n=3) with high linearity to plot the standard curve for TFIIS and β-actin. The relative expression ratio of TFIIS is calculated based on amplification efficiency and CP deviation of TFIIS siRNA versus a vehicle treated sample, and expressed in comparison to β-actin. Experiments is repeated three independent times and standard deviation is calculated.

Genearray Analysis

Microarray analysis is to be performed in the biopolymer core facility, which is fully staffed and equipped for this effort. Microarray analysis is performed using the Affymatrix genearray U133 with over 40,000 different ESTs. Total RNA will be isolated using the Trizol Reagent (Invitrogen; Carlsbad, Calif.). Total RNA is reverse-transcribed (RT) into cDNA. The cDNA is transcribed in vitro, resulting in amplified RNA (aRNA). The aRNA is then subjected to another RT reaction in the presence of Cyanine 3 (Cy 3) or Cyanine 5 (Cy 5) label. Cy3 labeled cDNA probes are made from 3 μg of aRNA from vehicle-treated both Breast and prostate cancer and non-cancerous cells; Cy5-labeled cDNA probes are made from 6 μg of aRNA from TFIIS siRNA treated breast cancer, prostate cancer, and non-cancerous cells (to compensate for the reduced binding affinity of Cy5 relative to Cy3), as described. Three independently prepared Cy3-labeled and Cy5-labeled probes are hybridized to separate microarrays for 16 h at 65° C. The slides undergo a series of washes in decreasing ionic strength from 1×SSC to 0.05×SSC.

Fluorescent array images are simultaneously collected for both Cy3 and Cy5 at 532 and 635 nm wavelengths. respectively, via a fluorescent scanner. To normalize for the effect of non-specific fluorescence, the background intensity is subtracted from the feature intensity before ratio calculations are performed. To quantify changes in gene expression accurately, the mean, median, and standard deviation of the pixel intensities for each raw image are computed. The median of ratios is the median of the pixel-by-pixel ratios of pixel intensities that have had the median background intensity subtracted. The average of median ratios from the three independent hybridizations of gene array will be used for comparative analyses.

Example 5

RNAP Subunit Gdown1

RNA Polymerase II was known to date as the 12-subunit enzyme responsible for synthesizing pre-mRNAs in the eukaryote. The present inventors disclose herein the purification and identification of a distinct and abundant form of mammalian RNAPII with a novel 41 kD subunit, Rpb13. Rpb13 is identified as Gdown1, a protein of previously unknown function transcribed from the complex transcription unit GRINL1A. Rpb13 does not dissociate from RNAPII under any conditions tested and proved to exist in stoichiometric amounts with RNAPII. siRNA targeting Rpb13 in cancer cell lines including breast, prostate, lung and pancreatic results in extreme sensitivity and programmed cell death, primarily in breast cancer MCF7 cell line. The present inventors define Gdown1 as a core component of the transcription machinery, the thirteenth subunit of mammalian RNAPII and essential for breast cancer MCF7 cells survival.

Figure 10:
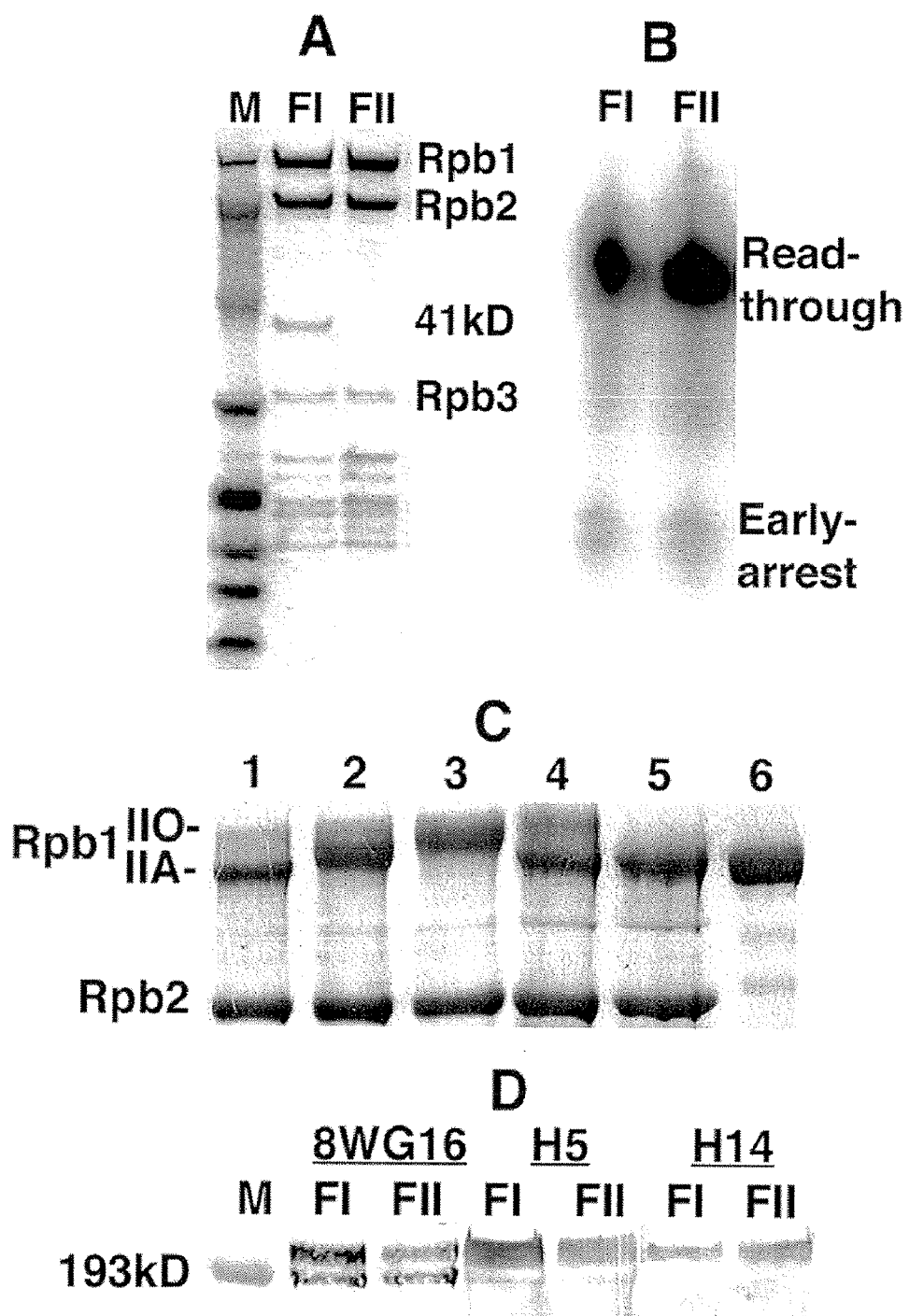

Purification of Mammalian RNAPII from Calf Thymus. By modifying the method of Thompson et al., (1990), the inventors were able to purify RNAPII to near homogeneity with fair yields (FIG. 10A). The most important change was the shortening of time required for purification by removing ammonium sulfate precipitation steps. The entire preparation can be accomplished in eight hours. Rapid purification reduces degradation of RNAPII resulting in increased yields and quality of protein. Yields were in the range of 6-8 mg of RNAPII/kg calf thymus.

A Novel and Abundant Mammalian RNAPII Form Contains an Additional Polypeptide. The most intriguing finding was the presence of an additional 41 kD subunit of mammalian RNAPII. The final step of purification consisted of a linear gradient of ammonium sulfate on an UNO-Q HPLC column and resulted in the partial separation of two forms of calf thymus RNAPII. (FIG. 10A). Both forms share the common 12-subunits, while FI contains an additional 41 kD polypeptide. FI represents approximately 30% of purified calf thymus RNAPII and 50% of pig liver RNAPII. Both RNAPII forms are active in a nonspecific transcription elongation assay that does not require general transcription factors for initiation (Gnatt et al., 1997) with no functional difference detected (FIG. 10B).

Phosphorylation State of RNAPII Forms I and II. Since phosphorylation of the RNAPII CTD on serine 2 and 5 plays a key role in transcriptional regulation, an assessment of the state of phosphorylation of FI and FII was performed. Employing a mixture of FI and FII, only small amounts of the higher molecular weight phosphorylated RNAPIIO were observed in 6% SDS-PAGE (FIG. 10C). Furthermore, the IIA form could be fully phosphorylated and the small amount of IIO could be fully dephosphorylated (FIG. 10C). From the size of the Rpb1 polypeptides, their ability to be converted into a fully phosphorylated or dephosphorylated form, it is evident that the purification procedure yields mostly RNAPIIA with minor amounts of RNAPIIO.

To positively rule in or out a correlation between the state of phosphorylation and the 41 kD polypeptide present in FI, the inventors determined the state of CTD phosphorylation of FI and FII separately. Western analysis was performed with antibodies H5 for phospho-Ser2, H14 for phospho-Ser5 and 8WG16 for both phosphorylated and unphosphorylated CTD. Since both Forms I and II are observed to share similar phosphorylation patterns, it does not appear that the state of phosphorylation is correlated with the presence or absence of the 41 kD polypeptide (FIG. 10D).

The 41 kD Polypeptide Present in FI RNAPII is Gdown1. The additional 41 kD polypeptide was positively identified by Edman degradation as Gdown1 (Roginski et al., 2004) and further corroborated by peptide fingerprinting with inferred peptides determined by tandem MS-MS (supplemental data S1 and S2). Edman degradation of peptides from the 41 kD polypeptide resulted in two peptide sequences, peptide A, AAIAEREEVRGRSELFYPVS (SEQ ID NO:29) and peptide B, (MYA)QXYNPEGE (SEQ ID NO:30), where ( ) represents a pool of possible amino acids and X representing an unidentified amino acid. Based on its sequence, PSORT predicts Gdown1 to be a nuclear protein with a 73.9% probability (Nakai and Horton, 1999).

Gdown1 is one of many polypeptide products of the GRINL1A Complex Transcription Unit (CTU) (Roginski et al., 2004). Identification of the 41 kD polypeptide as Gdown1, as opposed to other GRINL1A CTU products, is evident from a sequence alignment of Edman degradation polypeptides with other GRINL1A products, since Gdown1 alone possesses both peptide sequences (FIG. 11A). Peptide sequencing verifies the origin of the Gdown1 as bovine since only calf thymus Gdown1 and not human, orangutan, mouse, frog, or rat contain the tyrosine residue which appears in peptide A (FIG. 11B).

Gdown1 is a Novel Thirteenth RNAPII Subunit. Different forms of RNAPII with an altered affinity to the UNO-Q column is explained by the presence of Gdown1, particularly if it was stoichiometric in FI RNAPII, in specific embodiments of the invention. An assessment of the abundance of Gdown1 relative to subunits Rpb3 and 5 in FI RNAPII was performed by quantification of seven Coomassie stained SDS-PAGE gel bands. This included a gel containing a reconstituted FI generated by adding rhGdown1 to a mixture of FI and FII. The average molar ratio of Gdown1 to Rpb5 was 1.00 with a standard error of 0.07 and the average molar ratio of Rpb3 to Rpb5 was 0.91, with a standard error of 0.1. This indicates a stoichiometric amount of Gdown1 in Form I RNAPII. The presence of Gdown1 is, therefore, directly correlated with FI and can explain the existence of the two Forms.

If Gdown1 is a subunit of RNAPII, its binding to RNAPII should be equivalent to that of other RNAPII subunits. Some indication of the strength of the Gdown1-RNAPII interaction is evident from the RNAPII purification method, requiring routine high salt washes of 500 mM ammonium sulfate without dislodging the 41 kD polypeptide. In S. cerevisiae, RNAPII subunits four and seven dissociate from the core enzyme in the presence of 2.0M urea (Edwards et al., 1991). A mixture of FI and FII was therefore subjected to urea on UNO-Q HPLC. No dissociation from Form I RNAPII was observed in the presence of 2.5M urea and higher concentrations of urea caused elution of all the RNAPII from the column.

To preclude co-elution of RNAPII and Gdown1 in urea from the UNO-Q column as a result of similar elution properties, it was necessary to subject FI to a sizing column in the presence of 2M urea. If Gdown1 was tightly bound to RNAPII they would co-elute in a stoichiometric fashion and if not they would elute separately as RNAPII is more than ten-fold larger than Gdown1. Also tested was the ability to reconstitute a urea stable FT RNAPII by adding rhGdown1 to IIO to rule out a possible connection between the presence of Gdown1 and the state of CTD phosphorylation.

Figure 12:
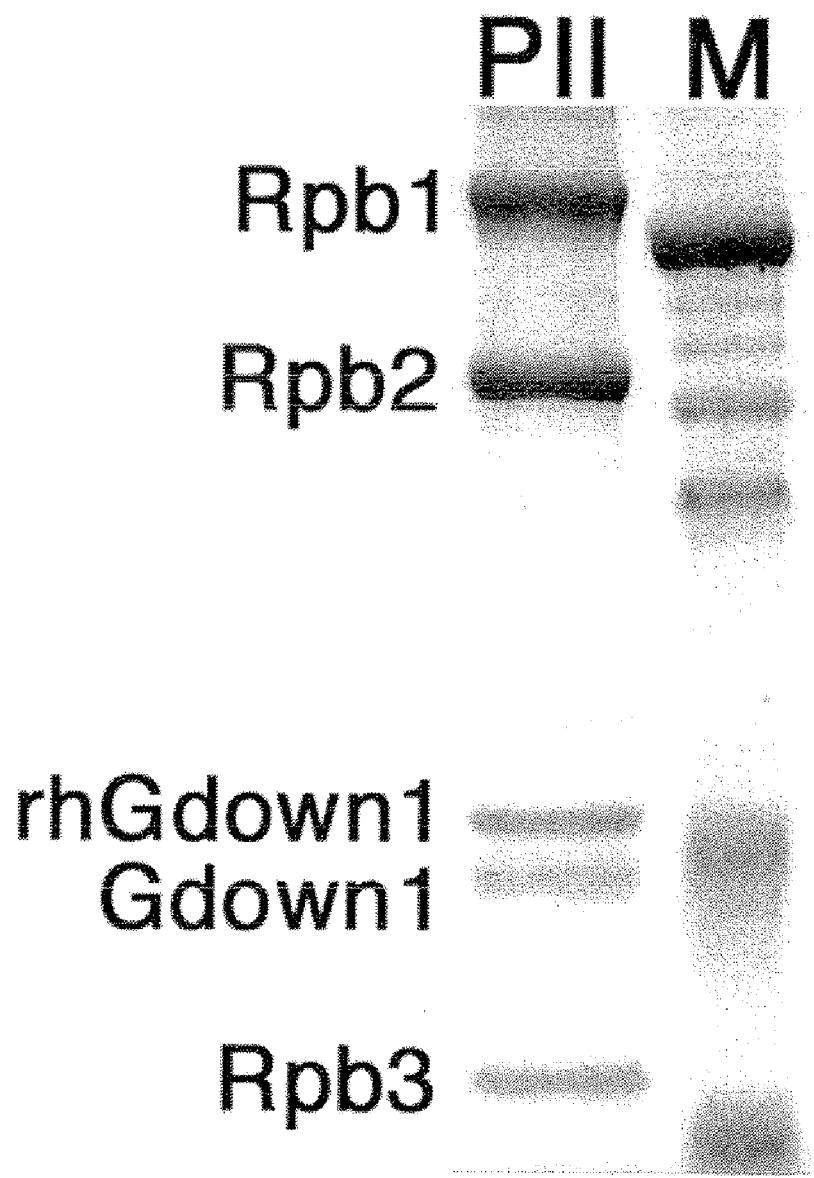
FIG. 12 demonstrates that reconstituted FI RNAPII migrates as a single entity on size exclusion columns in the presence of 2.0 M urea. A phosphorylated mixture of FI and FII RNAPII, (PII) was subjected to size exclusion chromatography in the presence of 2.0 M urea, separated by SDS-PAGE and stained with Coomassie. M represents markers of sizes 193, 103, 60, 42 and 28 kD. Rpb1-3, native calf thymus Gdown1 and rhGdown1 are listed as well.

Histidine tagged rhGdown1 was therefore added to a mixture of FT and FIT containing mostly hyperphosphorylated CTD (IIO). rhGdown1 is slightly heavier than the native calf thymus Rpb13 due to the additional tag and both recombinant and native polypeptides were observed to co-elute with RNAPII from size exclusion columns in the presence of 2.0M urea (FIG. 12). The IIO form, which contains mostly hyperphosphorylated CTD bound and co-eluted with rhRpb13 in the presence of 2.0M urea. This indicates that FT can be reconstituted from FII RNAPII and rhGdown1 to generate a urea stable FI. Taken together these results indicate that Gdown1 is a thirteenth RNAPII subunit. To facilitate further discussion regarding the thirteenth RNAPII subunit, Gdown1 and Rpb13 are herein employed interchangeably depending on the context.

Figure 13:
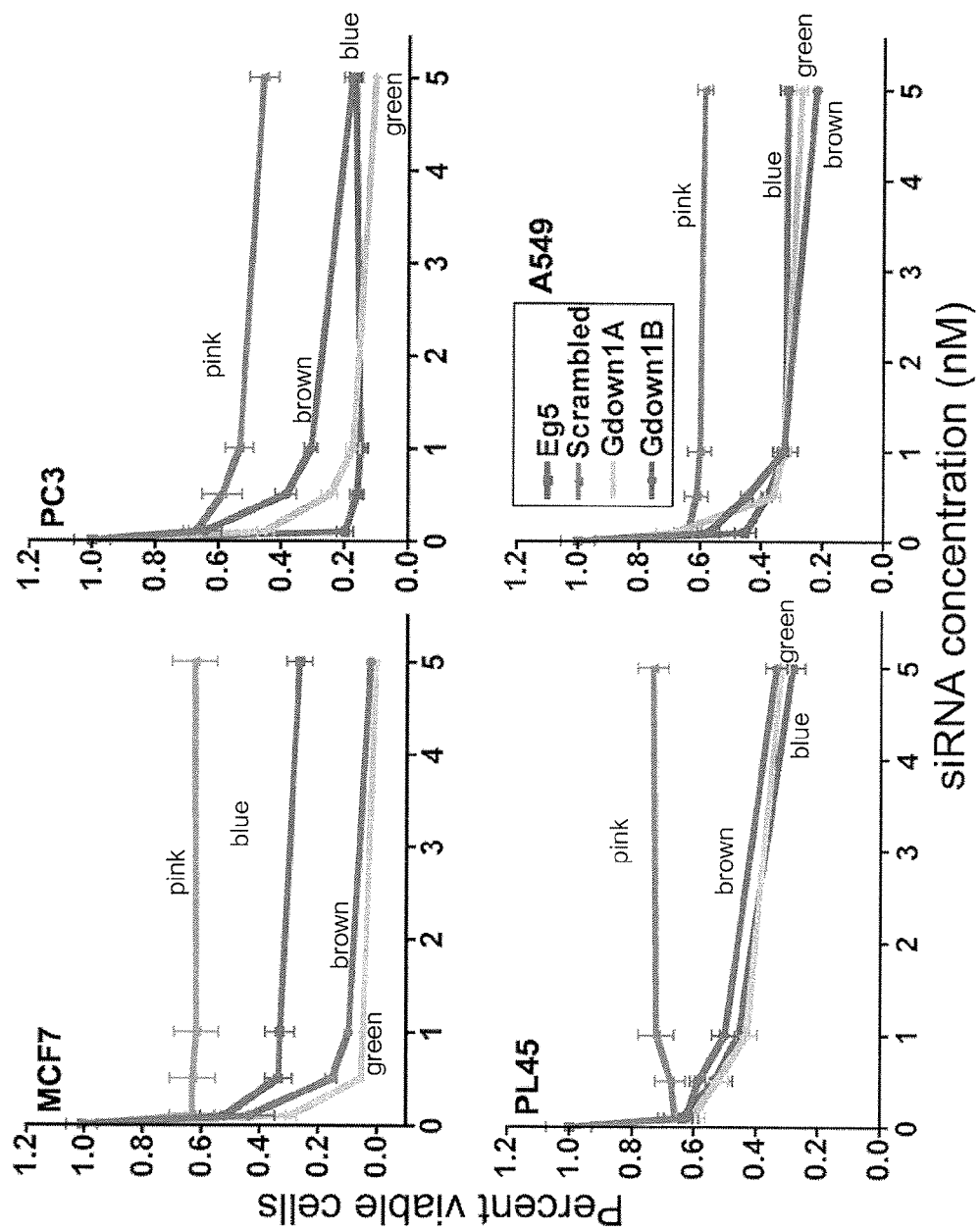
FIG. 13 shows siRNA targeting of Rpb13. The y-axis represents percent viable cells with vehicle-treated cells representing 100% viability, and the x-axis represents siRNA concentration in nM. The four cancer cell lines tested and their associated cancer type were MCF7 for breast, PC3 for prostate, PL45 for pancreatic and A549 for lung. A scrambled GAPDH siRNA, Eg5 positive control, and the Gdown1A and Gdown1B siRNAs are indicated in the figure.

Rpb13 is Necessary for Breast Cancer MCF7 Cell Survival. To gain insight into the importance of Rpb13 as a core RNAPII subunit, siRNA was employed to reduce its expression in exemplary breast, prostate, pancreatic and lung cancer cell lines (FIG. 13). Two different regions of Rpb13 mRNA were targeted with similar results. siRNA targeting Eg5, a member of the kinesin superfamily, was employed as a positive control. Eg5 plays a key role in mitosis, is required for the formation of a bipolar spindle and is a possible cancer target (DeBonis et al., 2004). Inhibiting Eg5 would result in prolonged mitotic arrest, leading to apoptosis in certain cell lines (Weil et al., 2002). A scrambled GAPDH sequence was employed as a negative control.

A significant degree of growth inhibition was observed when employing siRNA directed at Rpb13, for prostate, pancreatic and lung cancer cell lines, clustering with Eg5 growth inhibition (FIG. 13). Unlike the other cancer cell lines, MCF7 cells targeted with Rpb13 siRNA did not cluster with Eg5 siRNA inhibition (FIG. 13). In breast cancer MCF7 cells, siRNA targeted Rpb13 resulted in a significant and nearly complete growth inhibition. The increased dramatic sensitivity observed for MCF7 cells to Rpb13 siRNA, compared to other cell lines indicates a differential requirement for Rpb13 in MCF7 cells. In PC3 cells alone, Eg5 siRNA inhibition was markedly more effective at lower doses than that of Gdown1 siRNA.

Figure 14:
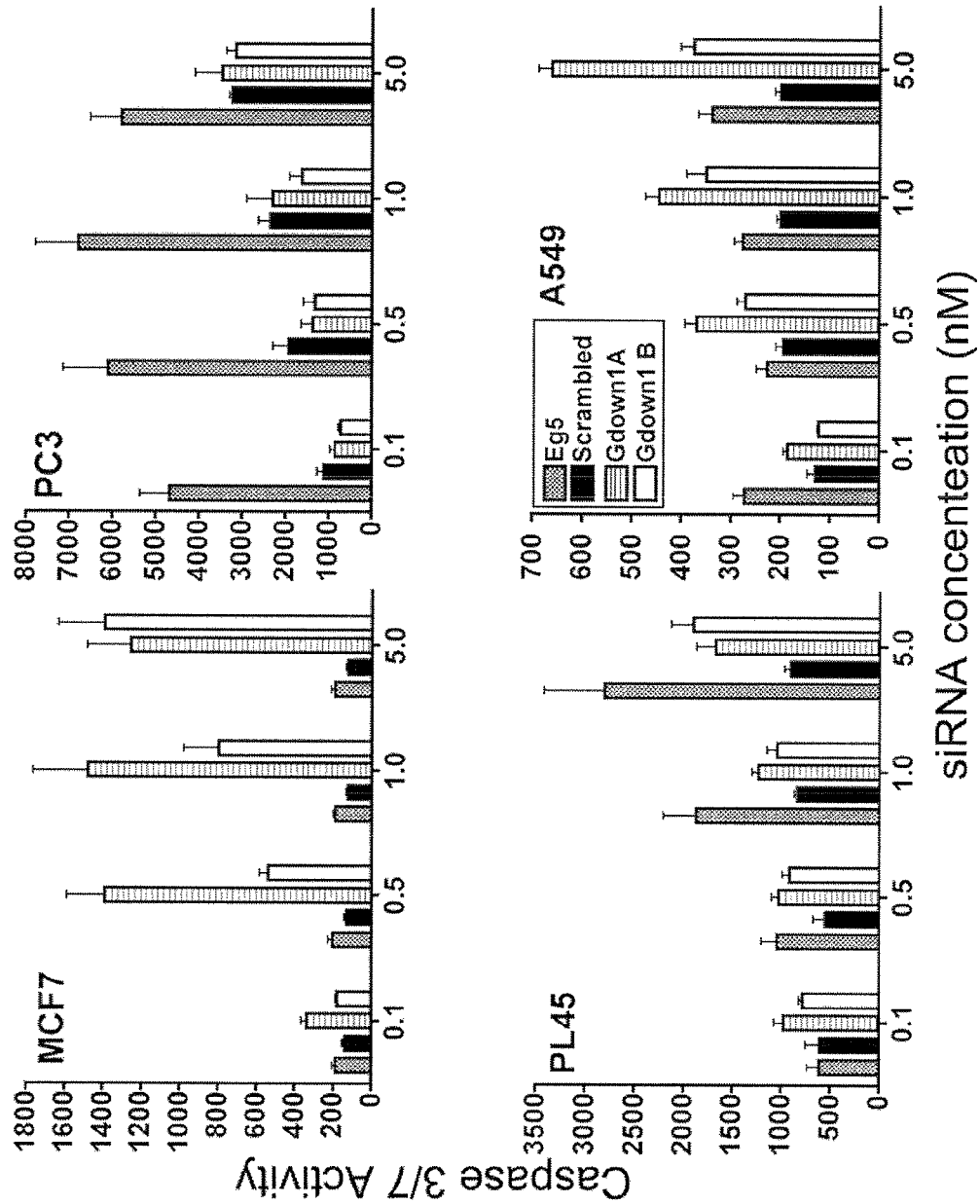
FIG. 14 demonstrates programmed cell death in Rpb13 siRNA treated and untreated cells. Caspase 3 and 7 activity measured by relative florescence are normalized to cell viability as determined by the MTS assay. Exemplary siRNAs employed to target Gdown1 are Gdown1A and Gdown1B listed in Example 5.

Real-time PCR was used to validate the specificity of siRNA targeting of Rpb13, as antibodies to Gdown1 are not available. siRNA directed at β-actin was employed as an internal control. Real-time PCR of mRNA from MCF7 cells collected 48 hours after being treated with 5 nM siRNA demonstrates that the Rpb13 transcript is 47% down regulated with a standard deviation of 6.2 compared to control. Raw data is supplied in FIG. 17.

siRNA Rpb13-Targeted MCF7 Breast Cancer Cell Death is the Result of Apoptosis. In order to assess if cell growth inhibition was the result of growth arrest, necrosis or programmed cell death, siRNA targeted cancer cell lines were assayed for Caspase 3 and 7 activity and normalized for cell viability. The findings indicate a dramatic and significant ten-fold increase in apoptosis occurring in MCF7 cells above scrambled siRNA inhibition even at the lower dose of 0.5 nM siRNA (FIG. 14). It further showed apoptosis at low siRNA concentrations by Eg5 siRNA in PC3 cells. These findings correlate well with the dramatic growth inhibition observed in Rpb13/Gdown1 siRNA treated MCF7 cells and the low-dose sensitivity of PC3 cells to Eg5 siRNA. To a lesser degree, up to 4-fold apoptosis is also observed in the pancreatic cancer PL45 cell line by Eg5 siRNA and in Lung A495 cancer cells by Rpb13. This indicates that both growth arrest and some degree of apoptosis are at play in these cells.

A Novel RNAPII Subunit. Gdown1 does not dissociate from RNAPII in the presence of urea or high salt, separates with RNAPII as a distinct form on UNO-Q HPLC, co-migrates with RNAPII on a sizing column and is present in stoichiometric amounts in both purified FI and reconstituted RNAPII/Gdown1 complexes. Taken together with FI abundance of over 30% in calf thymus and over 50% in pig liver, evidence in hand defines Gdown1 as the thirteenth subunit of RNAPII, Rpb13.

The high cellular proportion of FI is intriguing, since others have achieved purification of RNAPII yet the identification of a thirteenth subunit was not reported. However, upon close scrutiny of published reports of mammalian RNAPII purification, a 41-44 kD polypeptide co-purifies with RNAPII and is clearly visible on SDS PAGE gels (Tsai et al., 1984; Yeo et al., 2003; Dahmus, 1981; Schwartz and Roeder, 1975; Benson et al., 1978). For example, Hodo and Blatti reported a 44 kD polypeptide but suggested that it is a contaminant, since it was not stoichiometric and could be removed by a sizing column (Hodo, 1977). In that case though, when comparing the intensity of RNAPII subunits 1 and 2 before and after size exclusion chromatography, it appears that insufficient amounts of calf thymus RNAPII were loaded after the sizing column (Hodo, 1977). Sub-stoichiometric quantities of Rpb13 are reasonable, since RNAPII FI and FII were not separated and FI represents 30% of all the RNAPII after separation.

Various GRINL1A Polypeptide Products May Associate with RNAPII. Gdown1 is a product of the GRINL1A Complex Transcription Unit (CTU), a gene with two promoters and multiple introns and exons (Roginski et al., 2004). mRNA generation from the upstream and downstream promoters predicts Gup and Gdown proteins respectively. In addition, there exist transcripts termed Gcom for Gcombined that initiate from the upstream promoter and contain encoded protein from both up and down transcription sites. Upstream promoter cDNAs share homology with NMDA receptors though downstream promoter products such as Gdown1 do not. For example, Gcom1 is an NMDA receptor like protein, yet it shares a common C-terminal domain with Rpb13. This may not have functional significance since different cellular locations for Gcom1 and Rpb13 may exist. Rpb13 is integral to RNAPII and predicted to be a nuclear protein. Preliminary data by Roginsky et al., indicates that Gcom1 co-localizes with the mouse NR1NMDA receptor subunit in the plasma membrane of transfected cells and rat hippocampal neurons (Roginski et al., 2004).

Domain identity amongst various GRINL1A transcripts suggests that more than one GRINL1A polypeptide may bind RNAPII. Human Gdown2 has a predicted molecular weight of 40.6 kD and bovine Gdown1 a predicted molecular weight of 41.4 kD. It is not clear if the mobility of Gdown1 and Gdown2 in SDS PAGE would allow for differentiation between the two though peptide sequences A and B (FIG. 11) from Edman degradation are consistent with Gdown1. Evidence in hand may however be insufficient to preclude the existence of different forms of RNAPII with other GRINL1A polypeptide products. The inventors estimate the total RNAPII at 12-14 mg/kg calf thymus by assaying in a Western dot blot using 8WG16. The yield represents a maximum of 8 mg/kg totaling 60% of all detectable RNAPII. It is possible that other RNAPII forms containing different GRINL1A polypeptides exist in the 40% of RNAPII that we have not observed. Finally, expression of different GRINL1A polypeptides could be tissue specific and/or developmentally related. Indeed Gdown6 which shares N and C-terminal domains with Gdown1 does not appear to be expressed in mouse embryonic tissue though it is expressed in mouse extra-embryonic tissue (Ko et al., 1998).

Rpb13 Function. It is evident that Rpb13 is a novel core subunit of Form I mammalian RNAPII and therefore is a transcription-related polypeptide. Its importance is indicated from the high level of conservation across species with 71% identity between frog and man. It is possible that Rpb13 has evolutionary and developmental importance as Gdown1 has homologues in mammals, fish and *C. elegans*, though the inventors were unable to detect homologues in lower eukaryotes such as yeast.

Rpb13 may play a role similar to other RNAPII subunits. Rpb1 and Rpb2 alone contain the RNAPII active site, and other subunits can have non-catalytic roles. For example, Rpb5 and 9 comprising most of the "jaw" domain contact downstream DNA and help with its alignment. Non-catalytic RNAPII subunits may also play key roles in the regulation of transcription. For example, Rpb3 and 11 functionally interact with other polypeptides that regulate transcription (DeAngelis et al., 2003; Corbi et al., 2002; Fanciulli et al., 1998; Fanciulli et al., 1998; Pillai et al., 2001). Another example is Rpb4, which is a non-essential *S. cerevisiae* RNAPII subunit which is important for activated transcription of a subset of genes (Pillai et al., 2001). Subunits may also be involved in transcript processing, such as Rpb7, that interacts with an RNA-binding protein involved in the processing of transcripts (Mitsuzawa et al., 2003).

In specific aspects of the invention, Rpb13 is a regulatory component of higher eukaryotic expression at the level of pre-elongation. First, Gdown6 that comprises N-and C-terminal domains identical to Rpb13 is not expressed in embryonic tissue but is expressed in extra-embryonic tissue, suggesting a developmentally-regulated expression (Ko et al., 1998). Second, the MCF7 breast cancer sensitivity to Rpb13 siRNA inhibition compared to the lung, pancreatic and prostate cancer cell lines indicates a greater dependence on Rpb13 for cell survival. Indeed, MCF7 cells alone underwent dramatic apoptosis indicating that Rpb13 must either be inhibiting apoptosis or be essential for activating rapid cell growth in MCF7 cells. Interestingly, since Eg5 is a candidate target for cancer therapy (Weil et al., 2002; Marcus et al., 2005; Haque et al., 2004), Rpb13 may be a valid target as well. Although the connection between cancer and the newfound RNAP subunit requires further study, antibodies to a GRINL1A gene product exist in human leukemia patients (Guinn et al., 2005). Third, the absence of lower eukaryotic homologues suggests a possible role in non-basal transcription. Fourth, FI RNAPII containing Rpb13 represented 30% of all purified RNAPII in calf thymus whereas in liver it represented 50% or more, suggesting a tissue specific difference. Finally, RNAPII and Rpb13 were part of a mediator complex involved in global gene regulation, in which the complex was isolated by affinity purification of a FLAG tagged mediator component, CRSP70/MED26 (Sato et al., 2004).

In specific embodiments of the invention, various GRINL1A-derived polypeptides incorporate into RNAPII and thereby exert an alternate regulatory effect. In further specific embodiments, this parallels the finding in humans of alternate subunit 11 transcripts encoding proteins with common domains (Grandemange et al., 2001).

Example 6

Figure 18:
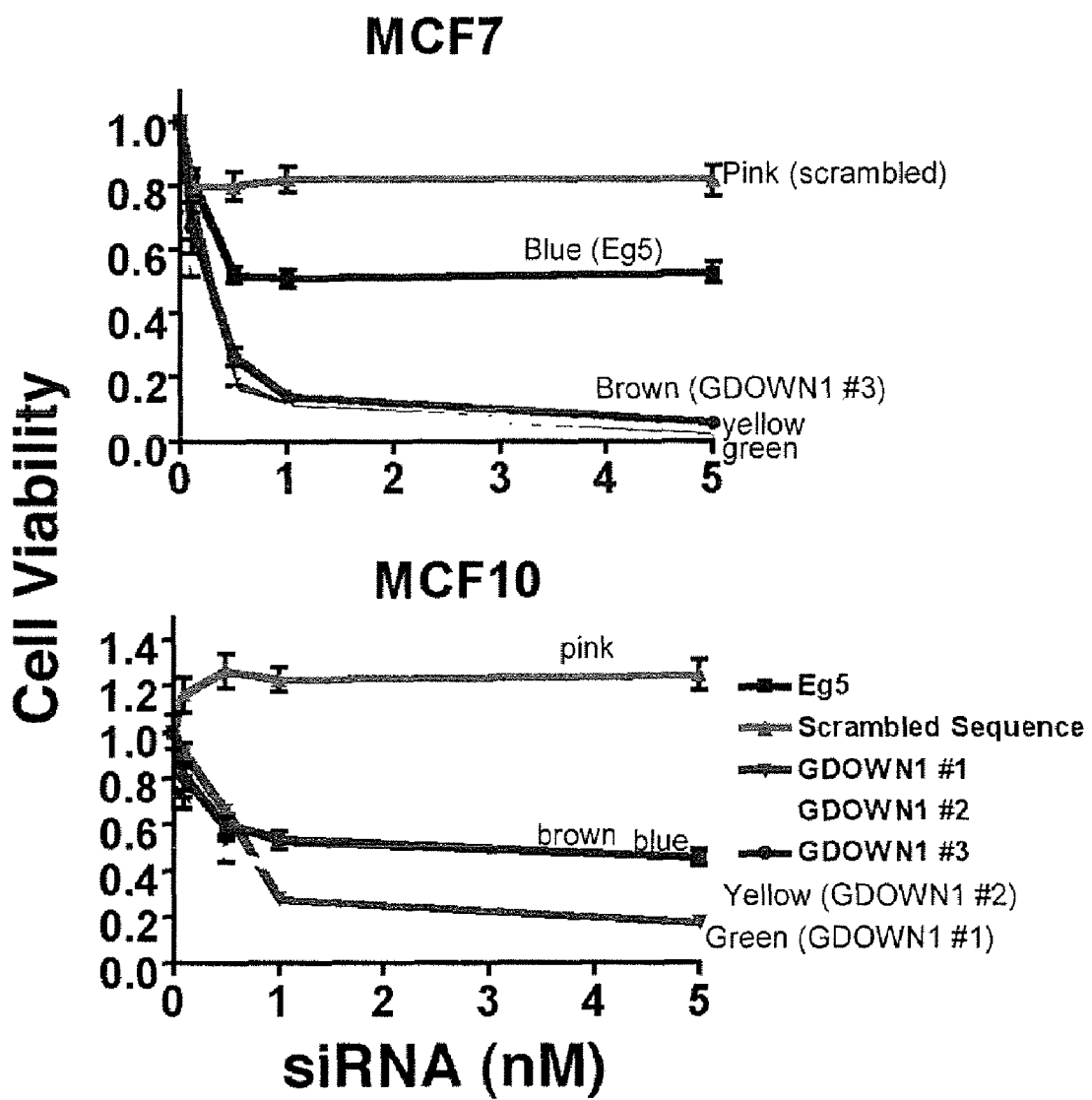
FIG. 18 illustrates Gdown1 siRNA inhibition utilizing exemplary GDown1 siRNAs.

Gdown1 siRNA Inhibition siRNA inhibition of Gdown1 employing three different siRNAs was performed as was done for TFIIS inhibition and is illustrated in FIG. 18. Exemplary targeted siRNA regions of human Gdown1 were as follows:

```
                                         (SEQ ID NO:31)
GDOWN1 #1: 5'-AACGAAAAAUUCAUUUGCAAA-3';

(SEQ ID NO:32)
GDOWN1 #2: 5'-AAGUUAGAAGAAAAAGUGAAC-3';

(SEQ ID NO:33)
GDOWN1 #3: 5'-AAGUCAUCUCAAACCUCACAA-3'.
```

EG5 is a kinesin motor protein that causes cell death and is a new target for cancer treatment; herein it is employed as a positive control. Note that MCF7 breast cancer cell death is nearly 100% complete and is dramatic at 1 nM siRNA. In non-cancerous MCF10 breast cells, although cell survival is dramatically better than in MCF7 tumor cells, there is displayed a pattern similar to that of EG5. In summary, in MCF7 cells, TFIIS inhibition is lethal to all cells and in MCF10, cell survival is observed.

Example 7

Materials and Methods for Example 5

The present example provides exemplary materials and methods used in the invention.

Purification of RNA Polymerase II. Calf thymus and pig liver were from Pel Freeze Inc. (Rogers, Ark.). RNAPII was purified as described with minor modifications (Thompson et al., 1990). Changes in purification included the following: 1) omission of the ammonium sulfate precipitation replaced by a PEI precipitation; 2) a chromatography column with Macro-Prep High Q Support (Bio-Rad, Inc.; Hercules, Calif.) instead of the original batch chromatography with DEAE Sepharose CL-6; and 3) a final separation on a Bio-Rad Duo-Flow HPLC System using an UNO Q-1 column (Bio-Rad, Inc.; Hercules, Calif.) eluted with a linear gradient of ammonium sulfate from 100 mM to 500 mM. Two RNAPII peaks were observed. The first was termed Form I (FI) and the second was termed Form II (FII) based on their order of elution. FI contained RNAPII with an additional 41 kD polypeptide. The maximum RNAPII yield was 8 mg/kg calf thymus.

Analysis of RNAPII Phosphorylation State. The phosphorylation state of a mixture of purified FI and FII was observed on a 6% acrylamide gel. Briefly, 0, 5 or 10 µg of human p42 MAPK2 (Supplied by J. Fu, Cornell) was added to 25 µl of 0.58 mg/ml purified FII in buffer A containing 10 mM $MgCl_2$, 350 mM $(NH_4)_2SO_4$, 50 mM Tris pH 7.5, 1 mM EDTA, 10 µM $ZnCl_2$, 10% glycerol and 10 mM DTT. The reaction was performed for 16 hours at 4° C. Dephosphorylation of RNAPII was accomplished with 20 µl of 0.58 mg/ml purified RNAPII from UNO-Q HPLC in buffer A. Three µl of 10×-reaction buffer with 1 unit of calf intestinal phosphatase were added for 1 hr at room temperature (New England Biolabs; Ipswich, Mass.). Samples before and after the reaction were subjected to SDS-PAGE and Coomassie stained.

Polypeptide Identification. Direct sequencing of the 41 kD polypeptide was achieved by Edman degradation employing a modified porcine Trypsin (Promega; Madison, Wis.). The SDS-PAGE separated 41 kD band was excised and digested similar to that previously described (Katayama et al., 2004; Havlis et al., 2003). Peptides were fractionated by RP-HPLC on a 0.3×100 mm Clipeus C18 column (The Nest Group). The amino acid sequences of these peptides were determined by automated Edman degradation with a model 494 Procise sequencer (Applied Biosystems; Foster City, Calif.). Confirmation of additional peptides was by standard mass spectral analysis of the 41 kD protein employing calf thymus RNAPII Rpb3 as a positive control and was performed in the Proteomics Resource Center of the Rockefeller Institute. The 41 kD polypeptide was identified as Gdown1, a product of the GRINL1A complex transcription unit (Roginski et al., 2004). Alignment of sequences employed the GeneBee program (Brodskii et al., 1995)

Expression of Recombinant Human Gdown1 (rhGdown1). A human Gdown1 homologue (Lib 969, RZPD, Germany) was cloned into pET 100/D-TOPO vector using the forward and reverse primers 5'-CACCATGTGCTCGCTGC-CCCGCGGCTTCGAGC-3' (SEQ ID NO:17) and 5'-TCA-GAATTCATCAGAGGACCAATCGTCATC-3' (SEQ ID NO:18), respectively, and was expressed in BL21 cells (Invitrogen). The protein induced by IPTG was purified using a nickel-NTA column as described by the manufacturer. (Qiagen, Inc.; Valencia, Calif.).

Reconstitution of Form I RNAPII with rhGdown1. Purified rhGdown1 was added to a mixture of FI and FII at a molar ratio of 3:1, respectively. The solution was incubated for 10 min at 4° C. and subjected to an UNO Q-1 column as described for the last stage of RNAPII purification. Protein fractions were $(NH_4)_2SO_4$ precipitated in preparation for a sizing column.

Dissociation and Co-migration of Gdown1 the 41 kD polypeptide and RNAPII. 150 µg reconstituted FI from the above step was resuspended to 50 µg in 2 M urea, 50 mM $(NH_4)_2SO_4$, 10% Glycerol, 50 mM Tris, 1 mM DTT. The solution was incubated for 20 min at 4° C. and applied to a Bio-Silect SEC 250-50 sizing column (Bio-Rad, Inc.; Hercules, Calif.) equilibrated in the same buffer and was developed with the same buffer. Fractions were collected, TCA precipitated and subjected to SDS-PAGE analysis followed by Coomassie staining.

Western Blot Analysis and Quantification of Coomassie Stained Bands. Western blot analysis of RNAPII employed monoclonal antibodies 8WG16, H5, and H14 (COVANCE, #MPY-127R). For quantification of Coomassie-stained bands, purified or reconstituted FI RNAPII samples (10 μg) were subjected to 10% SDS-PAGE and gels scanned with a Perfection 1640SU scanner (EPSON). Quantification was performed by the ImageQuant™ TL V2003.02 (Amersham Biosciences Ltd; Buckinghamshire, UK) with data from seven independent gel lanes, and standard deviation was determined. The molar ratio of the 41 kD polypeptide was calculated relative to Rpb5. The molar ratio of subunit Rpb3 was also calculated as a control. In the case of reconstituted RNAPII, values for both rhGdown1 and bovine Gdown I polypeptides were summed together.

Nonspecific Transcription Assay. Transcription assays employed single stranded polydC tailed templates and purified mammalian RNAPII as previously described (Gnatt et al., 1997). The template and non-template strands are 5'-TTTTTCTTCCCCGAAACGCCT-TGCTCGCTGGTGTTCCCCCCCCCCC-3' (SEQ ID NO:19) and 5-AACACCAGCGAGCAAGGCGTTTCGGG-GAAGAAAAA-3' (SEQ ID NO:20), respectively. RNA generated by RNAPII was subjected to 15% denaturing urea polyacrylamide gel. Alpha-amanitin was employed as a control.

Cell Culture. MCF7 and PL45 cell lines were grown in DMEM medium containing 10% FBS and 1% Pencillin/Streptomycin. PC-3 and A549 cell lines were grown in Ham's Medium supplemented with 10% FBS and 1% Pencillin/Streptomycin (Invitrogen; Carlsbad, Calif.).

siRNA Gdown1 Growth Inhibition Assay. siRNAs were created employing the Silencer siRNA Construction Kit (Ambion). Targeted regions were as follows: Gdown1A: 5'-AAGUCAUCUCAAACCUCACAA-3' (SEQ ID NO:21) and Gdown1B: 5'-AAUUAUGAGGAGAUGCAAGCA-3' (SEQ ID NO:22). All cell lines were seeded at 2000 cells/well in 96-well plates, and then transfected with 0.1, 0.5. 1.0, and 5.0 nM each of Eg5 (positive control), a scrambled GAPDH negative control (sequence as per Ambion Kit), and each of Rpb13 siRNAs using Lipofectamine 2000 (Invitrogen, Inc.; Carlsbad, Calif.); they were incubated for 72 hrs. Vehicle containing Lipofectamine 2000 alone was applied to cells and viable cells considered 100% survival. Assays were performed in quadruplicate with a minimum of 2 different experiments. Cell viability was determined employing the MTS assay as described by the manufacturer (Promega; Madison, Wis.).

Real Time RT-PCR. To quantify mRNA expression from 5 nM siRNA Gdown1-treated MCF7 cells and vehicle-treated cells, total RNA was isolated using the Trizol Reagent (Invitrogen, Inc.; Carslbad, Calif.). Total RNA was reverse transcribed using the iScript cDNA synthesis kit (Bio-Rad, Inc.; Hercules, Calif.). Real time RT-PCR was performed using the iQ™ SYBR Green Supermix Kit in a iCycler iQ (Bio-Rad, Inc.; Hercules, Calif.). β-actin was used as a standard for each sample tested. Exemplary Gdown1 primers included the forward primer, 5'-CATTGCGGACCAAGGTGAACAACA (SEQ ID NO:23) and the reverse primer, 5'-AGAC-CCACTCTTCTGGCAATGACT (SEQ ID NO:24). Exemplary β-actin primers included the forward primer, 5'-GC-TATCCAGGCTGTGCTATC (SEQ ID NO:25), and the reverse primer, 5'-TGTCACGCACGATTTCC (SEQ ID NO:26). Three independent experiments were performed, with mean and standard error calculated. Relative gene expression in the sample was determined using the comparative delta-delta CT method with β-actin as control (Pfaffl, 2001).

Apoptosis. To assay for programmed cell death, cells were treated as indicated for siRNAs, with MTS being substituted by the Caspase-Glo 3/7 assay reagent and plates read as instructed by the manufacturer of the Caspase-Glo system (Promega, Inc.; Madison, Wis.). Assays were performed in quadruplicate with a minimum of two different experiments. The data was analyzed to obtain the mean and standard error, and graphs were plotted using Prism (Graphpad Software, Inc.; San Diego, Calif.).

REFERENCES

All patents and publications mentioned in the specification are indicative of the levels of those skilled in the art to which the invention pertains. All patents and publications are herein incorporated by reference to the same extent as if each individual publication was specifically and individually indicated to be incorporated by reference.

PATENTS AND PATENT APPLICATIONS

WO 98/41648
WO 01/72777
WO 02/22660

PUBLICATIONS

Aklilu, M., et al., Phase II study of flavopiridol in patients with advanced colorectal cancer. Ann Oncol, 2003. 14(8): p. 1270-3.

Albright, S. R. & Tjian, R. (2000) Gene 242, 1-13.

Astrom, A. K., et al., Conserved mechanism of PLAG1 activation in salivary gland tumors with and without chromosome 8q12 abnormalities: identification of SII as a new fusion partner gene. Cancer Res, 1999. 59(4): p. 918-23.

Bains, M. A., I. Giles, and D. H. Wright, Distribution and configuration of c-myc RNA during transcriptional attenuation in differentiating cells in-situ. Histochem Cell Biol, 1997. 107(3): p. 259-63.

Belotserkovskaya, R., et al., Transcription through chromatin: understanding a complex FACT. Biochim Biophys Acta, 2004. 1677(1-3): p. 87-99.

Benson, R. H., Spindler, S. R., Hodo, H. G. & Blatti, S. P. (1978) Biochemistry 17, 1387-96.

Benson, R. H., et al., DNA-dependent RNA polymerase II stimulatory factors from calf thymus: purification and structural studies. Biochemistry, 1978. 17(8): p. 1387-96.

Bernard, D., et al., Myc confers androgen-independent prostate cancer cell growth. J Clin Invest, 2003. 112(11): p. 1724-31.

Blancato, J., et al., Correlation of amplification and overexpression of the c-myc oncogene in high-grade breast cancer: FISH, in situ hybridisation and immunohistochemical analyses. Br J Cancer, 2004. 90(8): p. 1612-9.

Brodskii, L. I., Ivanov, V. V., Kalaidzidis Ia, L., Leontovich, A. M., Nikolaev, V. K., Feranchuk, S. I. & Drachev, V. A. (1995) Biokhimiia 60, 1221-30.

Chrzan, P., et al., Amplification of c-myc gene and overexpression of c-Myc protein in breast cancer and adjacent nonneoplastic tissue. Clin Biochem, 2001. 34(7): p. 557-62.

Conaway, J. W., Shilatifard, A., Dvir, A. & Conaway, R. C. (2000) Trends Biochem Sci 25, 375-80.

Corbi, N., Di Padova, M., De Angelis, R., Bruno, T., Libri, V., Iezzi, S., Floridi, A., Fanciulli, M. & Passananti, C. (2002) Faseb J 16, 1639-41.

Cramer, P., Bushnell, D. A. & Kornberg, R. D. (2001) Science 292, 1863-76.

Dahmus, M. E. (1981) J Biol Chem 256, 3332-9.

Dahmus, M. E., Phosphorylation of eukaryotic DNA-dependent RNA polymerase. Identification of calf thymus RNA polymerase subunits phosphorylated by two purified protein kinases, correlation with in vivo sites of phosphorylation in HeLa cell RNA polymerase II. J Biol Chem, 1981. 256(7): p. 3332-9.

De Angelis, R., Iezzi, S., Bruno, T., Corbi, N., Di Padova, M., Floridi, A., Fanciulli, M. & Passananti, C. (2003) FEBS Lett 547, 15-9.

DeBonis, S., Skoufias, D. A., Lebeau, L., Lopez, R., Robin, G., Margolis, R. L., Wade, R. H. & Kozielski, F. (2004) Mol Cancer Ther 3, 1079-90.

Edwards, A. M., Kane, C. M., Young, R. A. & Kornberg, R. D. (1991) J Biol Chem 266, 71-5.

Ellwood-Yen, K., et al., Myc-driven murine prostate cancer shares molecular features with human prostate tumors. Cancer Cell, 2003. 4(3): p. 223-38.

Emery, J. G., E. H. Ohlstein, and M. Jaye, Therapeutic modulation of transcription factor activity. Trends Pharmacol Sci, 2001. 22(5): p. 233-40.

Fanciulli, M., Bruno, T., Di Padova, M., De Angelis, R., Iezzi, S., Iacobini, C., Floridi, A. & Passananti, C. (2000) Faseb J 14, 904-12.

Fanciulli, M., Bruno, T., Di Padova, M., De Angelis, R., Lovari, S., Floridi, A. & Passananti, C. (1998) FEBS Lett 427, 236-40.

Fluiter, K., et al., In vivo tumor growth inhibition and biodistribution studies of locked nucleic acid (LNA) antisense oligonucleotides. Nucleic Acids Res, 2003. 31(3): P. 953-62.

Garcia-Martinez, L. F., et al., In vitro high-throughput screening assay for modulators of transcription. Anal Biochem, 2002. 301(1): p. 103-10.

Gelmann, E. P. and O. J. Semmes, Expression of genes and proteins specific for prostate cancer. J Urol, 2004. 172(5 Pt 2): p. S23-6; discussion S26-7.

Gnatt, A., Fu, J. & Kornberg, R. D. (1997) J Biol Chem 272, 30799-805.

Gnatt, A., J. Fu, and R. D. Kornberg, Formation and crystallization of yeast RNA polymerase II elongation complexes. J Biol Chem, 1997. 272(49): p. 30799-805.

Grad, J. M., et al., Multiple androgen response elements and a Myc consensus site in the androgen receptor (AR) coding region are involved in androgen-mediated up-regulation of AR messenger RNA. Mol Endocrinol, 1999. 13(11): p. 1896-911.

Grandemange, S., Schaller, S., Yamano, S., Du Manoir, S., Shpakovski, G. V., Mattei, M. G., Kedinger, C. & Vigneron, M. (2001) BMC Mol Biol 2, 14.

Guinn, B. A., Bland, E. A., Lodi, U., Liggins, A. P., Tobal, K., Petters, S., Wells, J. W., Banhiam, A. H. & Mufti, G. J. (2005) Biochem Biophys Res Commun.

Haque, S. A., Hasaka, T. P., Brooks, A. D., Lobanov, P. V. & Baas, P. W. (2004) Cell Motil Cytoskeleton 58, 10-6.

Havlis, J., Thomas, H., Sebela, M. & Shevchenko, A. (2003) Anal Chem 75, 1300-6.

Hengartner, C. J., Myer, V. E., Liao, S. M., Wilson, C. J., Koh, S. S. & Young, R. A. (1998) Mol Cell 2, 43-53.

Hodo, H. G., 3rd & Blatti, S. P. (1977) Biochemistry 16, 2334-43.

Hodo, H. G., 3rd and S. P. Blatti, Purification using polyethylenimine precipitation and low molecular weight subunit analyses of calf thymus and wheat germ DNA-dependent RNA polymerase II. Biochemistry, 1977. 16(11): p. 2334-43.

Iversen, P. L., et al., Efficacy of antisense morpholino oligomer targeted to c-myc in prostate cancer xenograft murine model and a Phase I safety study in humans. Clin Cancer Res, 2003. 9(7): p. 2510-9.

Jain, M., et al., Sustained loss of a neoplastic phenotype by brief inactivation of MYC. Science, 2002. 297(5578): p. 102-4.

Jenkins, R. B., et al., Detection of c-myc oncogene amplification and chromosomal anomalies in metastatic prostatic carcinoma by fluorescence in situ hybridization. Cancer Res, 1997. 57(3): p. 524-31.

Katayama, H., Tabata, T., Ishihama, Y., Sato, T., Oda, Y. & Nagasu, T. (2004) Rapid Commun Mass Spectrom 18, 2388-94.

Keene, R. G., et al., Transcriptional pause, arrest and termination sites for RNA polymerase II in mammalian N- and c-myc genes. Nucleic Acids Res, 1999. 27(15): p. 3173-82.

Kelly, W. K., O. A. O'Connor, and P. A. Marks, Histone deacetylase inhibitors: from target to clinical trials. Expert Opin Investig Drugs, 2002. 11(12): p. 1695-713.

Kerppola, T. K. and C. M. Kane, Analysis of the signals for transcription termination by purified RNA polymerase II. Biochemistry, 1990. 29(1): p. 269-78.

Kerppola, T. K. and C. M. Kane, Intrinsic sites of transcription termination and pausing in the c-myc gene. Mol Cell Biol, 1988. 8(10): p. 4389-94.

Khazak, V., Estojak, J., Cho, H., Majors, J., Sonoda, G., Testa, J. R. & Golemis, E. A. (1998) Mol Cell Biol 18, 1935-45.

Khorasanizadeh, S., The nucleosome: from genomic organization to genomic regulation. Cell, 2004. 116(2): p. 259-72.

Kim, W. Y. & Dahmus, M. E. (1988) J Biol Chem 263, 18880-5.

Ko, M. S., Threat, T. A., Wang, X., Horton, J. H., Cui, Y., Pryor, E., Paris, J., Wells-Smith, J., Kitchen, J. R., Rowe, L. B., Eppig, J., Satoh, T., Brant, L., Fujiwara, H., Yotsumoto, S. & Nakashima, H. (1998) Hum Mol Genet 7, 1967-78.

Kobor, M. S. & Greenblatt, J. (2002) Biochim Biophys Acta 1577, 261-275.

Kornberg, R. D. (2001) Biol Chem 382, 1103-7.

Kornblihtt, A. R., de la Mata, M., Fededa, J. P., Munoz, M. J. & Nogues, G. (2004) Rna 10, 1489-98.

Larkin, R. M. & Guilfoyle, T. J. (1998) J Biol Chem 273, 5631-7.

Latil, A., et al., htert expression correlates with MYC overexpression in human prostate cancer. Int J Cancer, 2000. 89(2): p. 172-6.

Leone, G., et al., Inhibitors of DNA methylation in the treatment of hematological malignancies and MDS. Clin Immunol, 2003. 109(1): p. 89-102.

Lewis, B. A. & Reinberg, D. (2003) J Cell Sci 116, 3667-75.

Lin, P. S., Marshall, N. F. & Dahmus, M. E. (2002) Prog Nucleic Acid Res Mol Biol 72, 333-65.

Lu, C., et al., cFos is critical for MCF-7 breast cancer cell growth. Oncogene, 2005.

Luo, Y., et al., Transcription factor Fos-related antigen 1 is an effective target for a breast cancer vaccine. Proc Natl Acad Sci USA, 2003. 100(15): p. 8850-5.

Marcus, A. I., Peters, U., Thomas, S. L., Garrett, S., Zelnak, A., Kapoor, T. M. & Giannakakou, P. (2005) J Biol Chem 280, 11569-77.

Marshall, N. F., Peng, J., Xie, Z. & Price, D. H. (1996) J Biol Chem 271, 27176-83.

Mitsuzawa, H., Kanda, E. & Ishihama, A. (2003) Nucleic Acids Res 31, 4696-701.

Nakai, K. & Horton, P. (1999) Trends Biochem Sci 24, 34-6.

Nakanishi, T., et al., Structure-function relationship of yeast S-II in terms of stimulation of RNA polymerase II, arrest relief, and suppression of 6-azauracil sensitivity. J Biol Chem, 1995. 270(15): p. 8991-5.

Pfaffl, M. W. (2001) Nucleic Acids Res 29, e45.

Pfaffl, M. W., A new mathematical model for relative quantification in real-time RT-PCR. Nucleic Acids Res, 2001. 29(9): p. e45.

Pillai, B., Sampath, V., Sharma, N. & Sadhale, P. (2001) J Biol Chem 276, 30641-7.

Plet, A., D. Eick, and J. M. Blanchard, Elongation and premature termination of transcripts initiated from c-fos and c-myc promoters show dissimilar patterns. Oncogene, 1995. 10(2): p. 319-28.

Powell, W., Bartholomew, B. & Reines, D. (1996) J Biol Chem 271, 22301-4.

Proudfoot, N. J., Furger, A. & Dye, M. J. (2002) Cell 108, 501-12.

Reyes, J. C., C. Muchardt, and M. Yaniv, Components of the human SWI/SNF complex are enriched in active chromatin and are associated with the nuclear matrix. J Cell Biol, 1997. 137(2): p. 263-74.

Roginski, R. S., Mohan Raj, B. K., Birditt, B. & Rowen, L. (2004) Genomics 84, 265-76.

Sakurai, H., Mitsuzawa, H., Kimura, M. & Ishihama, A. (1999) Mol Cell Biol 19, 7511-8.

Sato, S., Tomomori-Sato, C., Parmely, T. J., Florens, L., Zybailov, B., Swanson, S. K., Banks, C. A., Jin, J., Cai, Y., Washburn, M. P., Conaway, J. W. & Conaway, R. C. (2004) Mol Cell 14, 685-91.

Schwartz, L. B. & Roeder, R. G. (1975) J Biol Chem 250, 3221-8.

Shilatifard, A. (2004) Biochim Biophys Acta 1677, 79-86.

Shor, J., E. Ben-Asher, and Y. Aloni, Transcription elongation of the murine ornithine decarboxylase (ODC) gene is regulated in vitro at two downstream elements by different attenuation mechanisms. Oncogene, 1995. 10(8): p. 1587-96.

Steiner, M. S., et al., Antisense c-myc retroviral vector suppresses established human prostate cancer. Hum Gene Ther, 1998. 9(5): p. 747-55.

Thompson, N. E., Aronson, D. B. & Burgess, R. R. (1990) J Biol Chem 265, 7069-77.

Thompson, N. E., D. B. Aronson, and R. R. Burgess, Purification of eukaryotic RNA polymerase II by immunoaffinity chromatography. Elution of active enzyme with protein stabilizing agents from a polyol-responsive monoclonal antibody. J Biol Chem, 1990. 265(12): p. 7069-77.

Tsai, S. Y., Dicker, P., Fang, P., Tsai, M. J. & O'Malley, B. W. (1984) J Biol Chem 259, 11587-93.

Vigushin, D. M. and R. C. Coombes, Histone deacetylase inhibitors in cancer treatment. Anticancer Drugs, 2002. 13(1): p. 1-13.

Weil, D., Garcon, L., Harper, M., Dumenil, D., Dautry, F. & Kress, M. (2002) Biotechniques 33, 1244-8.

Weir, H. K., et al., Annual report to the nation on the status of cancer, 1975-2000, featuring the uses of surveillance data for cancer prevention and control. J Natl Cancer Inst, 2003. 95(17): p. 1276-99.

Yeo, M., Lin, P. S., Dahmus, M. E. & Gill, G. N. (2003) J Biol Chem 278, 26078-85.

Yoo, O. J., et al., Cloning, expression and characterization of the human transcription elongation factor, TFIIS. Nucleic Acids Res, 1991. 19(5): p. 1073-9.

Yoshida, M., T. Shimazu, and A. Matsuyama, Protein deacetylases: enzymes with functional diversity as novel therapeutic targets. Prog Cell Cycle Res, 2003. 5: p. 269-78.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of inhibiting proliferation of at least one breast cancer cell in an individual, the method comprising delivering to the cell an effective amount of a composition comprising a siRNA that is 18-40 nucleotides in length that inhibits TFIIS (SEQ ID NO: 15), wherein the delivery is by direct delivery and wherein the breast cancer cell proliferation is differentially inhibited compared to non-cancerous cell proliferation.

2. The method of claim 1, wherein the siRNA comprises SEQ ID NO:7.

3. The method of claim 1, wherein the individual is further provided one or more additional anti-cancer therapies.

4. The method of claim 3, wherein the additional anti-cancer therapy comprises chemotherapy.

5. A method of treating an individual with breast cancer, the method comprising delivering to the individual an effective amount of a composition comprising a siRNA that is 18-40 nucleotides in length that inhibits TFIIS (SEQ ID NO: 15), wherein the delivery is by direct delivery and wherein the breast cancer proliferation is differentially inhibited compared to non-cancerous cell proliferation.

* * * * *